US012358981B2

(12) United States Patent
Zhang

(10) Patent No.: US 12,358,981 B2
(45) Date of Patent: *Jul. 15, 2025

(54) ANTI-CONNEXIN ANTIBODY FORMULATIONS

(71) Applicant: AlaMab Therapeutics, Inc., Princeton, NJ (US)

(72) Inventor: Yanfeng Zhang, Princeton, NJ (US)

(73) Assignee: ALAMAB THERAPEUTICS, INC., Princeton, NJ (US)

( * ) Notice: Subject to any disclaimer, the term of this patent is extended or adjusted under 35 U.S.C. 154(b) by 1239 days.

This patent is subject to a terminal disclaimer.

(21) Appl. No.: 17/061,918

(22) Filed: Oct. 2, 2020

(65) Prior Publication Data

US 2021/0101974 A1    Apr. 8, 2021

Related U.S. Application Data

(60) Provisional application No. 62/909,267, filed on Oct. 2, 2019.

(51) Int. Cl.

| | |
|---|---|
| C07K 16/28 | (2006.01) |
| A61K 9/08 | (2006.01) |
| A61K 39/395 | (2006.01) |
| A61K 47/18 | (2017.01) |
| A61K 47/22 | (2006.01) |
| A61K 47/26 | (2006.01) |
| A61K 39/00 | (2006.01) |

(52) U.S. Cl.
CPC ............... *C07K 16/28* (2013.01); *A61K 9/08* (2013.01); *A61K 39/3955* (2013.01); *A61K 47/183* (2013.01); *A61K 47/22* (2013.01); *A61K 47/26* (2013.01); *A61K 2039/505* (2013.01); *C07K 2317/34* (2013.01); *C07K 2317/56* (2013.01); *C07K 2317/565* (2013.01); *C07K 2317/94* (2013.01)

(58) Field of Classification Search
CPC .... C07K 16/18; C07K 16/28; C07K 2317/34; C07K 2317/56; C07K 2317/565; C07K 2317/94; A61K 9/08; A61K 39/3955; A61K 47/183; A61K 47/22; A61K 47/26; A61K 2039/505

See application file for complete search history.

(56) References Cited

U.S. PATENT DOCUMENTS

| | | | |
|---|---|---|---|
| 2005/0171339 | A1 | 8/2005 | Sugo et al. |
| 2006/0040883 | A1 | 2/2006 | You et al. |
| 2009/0324602 | A1* | 12/2009 | Garber .................... A61P 15/00 424/139.1 |
| 2012/0020961 | A1 | 1/2012 | Houhou et al. |
| 2016/0177298 | A1 | 6/2016 | Green et al. |
| 2017/0106090 | A1 | 4/2017 | Gadgil et al. |
| 2019/0040137 | A1 | 2/2019 | Hu et al. |
| 2019/0300615 | A1* | 10/2019 | Yang ....................... A61P 37/00 |

FOREIGN PATENT DOCUMENTS

| | | | |
|---|---|---|---|
| RU | 2408728 C1 | 1/2011 | |
| RU | 2457862 C1 | 8/2012 | |
| WO | WO 2005/059106 A2 | 6/2005 | |
| WO | WO 2009/140177 A2 | 11/2009 | |
| WO | WO 2015/027120 A1 | 2/2015 | |
| WO | 2017147561 A1 | 8/2017 | |
| WO | WO 2018/187057 A1 | 10/2018 | |
| WO | WO-2018204368 A1 * | 11/2018 | ......... A61K 39/3955 |
| WO | 2019195273 A1 | 10/2019 | |

OTHER PUBLICATIONS

Lloyd et al. Protein Eng. Design & Select, 2009, 22(3):159-168. (Year: 2009).*
Edwards et al. J. Mol. Biol. 2003, 334:103-118. (Year: 2003).*
Phillips et al. Anal. Chem. 2017, 89:2361-2368. (Year: 2017).*
Lin et al., "Connexin 43 enhances the adhesivity and mediates the invasion of malignant glioma cells," *J. Neurosci.*, 22(11):4302-4311 (2002).
Riquelme et al., "Antibodies targeting extracellular domain of connexins for studies of hemichannels," *Neuropharmacology*, 75:525-532 (2013).
International Search Report and Written Opinion in International Application No. PCT/US2020/054036 mailed Feb. 10, 2021.
Avis et al., "Pharmaceutical Dosage Forms: Parenteral Medications," Marcel Dekker (1991), vol. 1, Second Edition (Textbook).
Avis et al., "Pharmaceutical Dosage Forms: Parenteral Medications," Marcel Dekker (1993), Second Edition (Textbook).
Berge et al., "Pharmaceutical Salts," Journal Pharmaceutical Sciences, 1977, vol. 66, No. 1, pp. 1-19.
Gennaro et al., "Remington: The Science and Practice of Pharmacy," Lippincott, Williams, and Wilkins (2000), Twentieth Edition (Textbook).
Grachev et al., "WHO Requirements for the Use of Animal Cells as in Vitro Substrates for the Production of Biologicals (Requirements for Biological Substances No. 50)," Biologicals, vol. 26, Issue 3, Sep. 1998, pp. 175-193.
Hardman et al., "Goodman and Gilman's The Pharmacological Basis of Therapeutics," McGraw-Hill (2001), vol. 1, Eleventh Edition (Textbook).
Hunt, Andrew, "Dictionary of Chemistry," Routledge (1999), First Edition (Textbook).
Kabat et al., "Sequences of Proteins of Immunological Interest," Public Health Service—National Institutes of Health (1991) (Textbook).

(Continued)

*Primary Examiner* — Kimberly Ballard
(74) *Attorney, Agent, or Firm* — GREENBERG TRAURIG, LLP

(57) ABSTRACT

The present disclosure relates to pharmaceutical compositions and methods for treating a disease or condition associated with insufficient opening of Cx43 hemichannels in osteocytes, optionally for treating cancer, cancer metastasis, osteosarcoma, osteoporosis, or osteopenia.

20 Claims, 16 Drawing Sheets

Specification includes a Sequence Listing.

(56) References Cited

OTHER PUBLICATIONS

Kumar et al., "Dictionary of Organic Chemistry," Anmol Publications Pvt. Ltd. (2002) (Textbook).
Kumar et al., "Encyclopedic Dictionary of Chemistry," Anmol Publications Pvt. Ltd. (2002) (Textbook).
Lieberman et al., "Pharmaceutical Dosage Forms: Disperse Systems," Marcel Dekker (1990), vol. 3, Second Edition (Textbook).
Lieberman et al., "Pharmaceutical Dosage Forms: Tablets," Marcel Dekker (1990), vol. 1, Second Edition (Textbook).
Martin et al., "A Dictionary of Biology—Oxford Paperback Reference," Oxford University Press (2000), Fourth Edition (Textbook).
Morris, Christopher, "Academic Press Dictionary of Science and Technology," Academic Press (1992), First Edition (Textbook).
Nahler, Gerhard, "Dictionary of Pharmaceutical Medicine," Springer Verlag (1994), First Edition (Textbook).
Remington et al., "Remington's Pharmaceutical Sciences," Mack Publishing Company (1984), Seventeenth Edition (Textbook).
Singleton et al., "Dictionary of Microbiology and Molecular Biology," John Wiley & Sons (2002), Third Edition (Textbook).
Smith et al., "Oxford Dictionary of Biochemistry and Molecular Biology," Oxford University Press (2000), Second Edition (Textbook).
Stahl et al., "Pharmaceutical Salts: Properties, Selection, and Use," Wiley-VCH (2008), Second Edition (Textbook).
Wang, Wei, "Instability, Stabilization, and Formulation of Liquid Protein Pharmaceuticals," International Journal of Pharmaceutics, 1999, vol. 185, pp. 129-188.
Wang, Wei, "Lyophilization and development of solid protein pharmaceuticals," International Journal of Pharmaceutics, Aug. 2000, vol. 203, Issues 1-2, pp. 1-60.
Weiner et al., "Excipient Toxicity and Safety," CRC Press (2000), First Edition, pp. 1-87.

\* cited by examiner

ANTI-CONNEXIN ANTIBODY FORMULATIONS

CROSS REFERENCE TO RELATED APPLICATIONS

This application claims priority to and the benefit of U.S. Provisional Patent Application No. 62/909,267 filed Oct. 2, 2019, the disclosure of which is incorporated herein by reference in its entirety.

SEQUENCE LISTING

The ASCII text file submitted herewith via EFS-Web, entitled "172628_020502_sequence.txt" created on Oct. 2, 2020, having a size of 43,784 bytes, is hereby incorporated by reference in its entirety.

FIELD

The present disclosure generally relates to stable aqueous pharmaceutical compositions comprising anti-connexin (Cx) 43 antibodies.

BACKGROUND

Antibodies have been used in the treatment of various diseases and conditions due to their specificity of target recognition, thereby generating highly selective outcomes following systemic administration. In order for antibodies to remain effective, they must maintain their biological activity during their production, purification, transport and storage. New production and purification techniques have been developed to provide for large amounts of highly purified monoclonal antibodies to be produced. However, challenges still exist to stabilize these antibodies for transport and storage, and yet even more challenges exist to provide the antibodies in a dosage form suitable for administration.

Denaturation, aggregation, contamination, and particle formation can be significant obstacles in the formulation and storage of antibodies. Due to the wide variety of antibodies, there are no universal formulations or conditions suitable for storage of all antibodies. Optimal formulations and conditions suitable for storage of one antibody are often specific to that antibody. Thus, antibody storage formulations and methods are often a significant part of the research and development process for a commercial antibody.

Various methods have been proposed to overcome the challenges associated with antibody stability. For example, in some instances, the antibody is often lyophilized, and then reconstituted shortly before administration. However, reconstitution is generally not ideal, since it adds an additional step to the administration process, and could introduce contaminants to the formulation. Additionally, even reconstituted antibodies can suffer from aggregation and particle formation. Thus, a need exists to provide stable, aqueous antibody formulations, in particular anti-Cx43 antibody formulations that can overcome the challenges associated with transport and storage.

SUMMARY

The present disclosure provides, in one aspect, a pharmaceutical formulation comprising:
an anti-Cx43 antibody or antigen binding fragment thereof,
a buffer;
a surfactant; and
a stabilizer;
wherein the pharmaceutical formulation has a pH of between about 5 and about 6;
wherein the anti-Cx43 antibody or antigen binding fragment thereof comprises:
a first, second and third heavy chain complementarity determining region (CDR) sequence having the amino acid sequence of SEQ ID NOs: 1, 2, and 3, respectively; and
a first, second and third light chain CDR sequence having the amino acid sequence of SEQ ID NOs: 4, 5, and 6, respectively.

In some embodiments, the anti-Cx43 antibody or antigen binding fragment thereof comprises a heavy chain variable domain having the amino acid sequence of SEQ ID NO: 7, and a light chain variable domain having the amino acid sequence of SEQ ID NO: 8.

In certain embodiments, the anti-Cx43 antibody or antigen binding fragment thereof comprises a heavy chain having an amino acid sequence selected from the group consisting of SEQ ID NOs: 9-17, and a light chain having the amino acid sequence of SEQ ID NO: 18.

In certain embodiments, the anti-Cx43 antibody or antigen binding fragment thereof binds to an epitope located within the amino acid sequence of FLSRPTEKTI (SEQ ID NO: 19). In some embodiments, the epitope can comprise one or more amino acids selected from the group consisting of F1, S3, R4, P5, T6, E7, K8, T9 and I10 of SEQ ID NO: 19. In one embodiment, the epitope consists of F1, S3, R4, P5, T6, E7, K8, T9 and I10 of SEQ ID NO: 19. In some embodiments, the epitope can include all ten amino acids of SEQ ID NO: 19. In certain embodiments, the epitope consists of all ten amino acids of SEQ ID NO: 19.

In some embodiments, the anti-Cx43 antibody or antigen binding fragment thereof is present at a concentration of between about 5 and about 50 mg/mL, optionally between 10 and 40, or from about 15 to 30 mg/mL.

In some certain embodiments, the buffer is selected from acetate/sodium acetate, histidine/aspartic acid, citric acid/sodium citrate, dibasic sodium phosphate/sodium dihydrogen phosphate, and histidine/histidine hydrochloride. In certain embodiments, the buffer is histidine/aspartic acid or histidine/histidine hydrochloride. In certain embodiments, the buffer is histidine/histidine hydrochloride.

In some embodiments, the surfactant is polysorbate 80 (PS80).

In certain embodiments, the stabilizer is selected from ethylenediaminetetraacetic acid (EDTA), sodium chloride, sorbitol, glycine, and sucrose. In certain embodiments, the stabilizer is sucrose.

In certain embodiments, the pH of the formulation is between about 5.4 to about 5.6.

In some embodiments, the formulation is an aqueous formulation. In some embodiments, the formulation is a stable aqueous formulation.

Another aspect relates to a pharmaceutical formulation comprising:
about 10-50 mg/mL, or about 25 mg/mL of an anti-Cx43 antibody or antigen binding fragment thereof;
about 10-40 mM, or about 20 mM histidine/histidine hydrochloride buffer;
about 0.005%-0.05%, or about 0.02% w/v Polysorbate 80; and
about 1%-20% w/v, or about 8% w/v sucrose;
wherein the formulation has a pH of between about 5 to about 6, or between about 5.4 to about 5.6, or about 5.5.

A further aspect relates to a pharmaceutical formulation comprising:
- about 25 mg/mL an anti-Cx43 antibody or antigen binding fragment thereof, comprising a heavy chain having an amino acid sequence selected from the group consisting of SEQ ID NOs: 9-17, and comprising a light chain having the amino acid sequence of SEQ ID NO: 18;
- about 20 mM histidine/aspartic acid buffer;
- about 0.02% w/v Polysorbate 80; and
- about 8% w/v sucrose,
- wherein the formulation has a pH of between about 5.4 to about 5.6, or about 5.5.

Also provided herein is use of the pharmaceutical formulations disclosed herein, for promoting opening of Cx43 hemichannels in osteocytes, such as for the treatment of cancer, cancer metastasis, osteosarcoma, osteoporosis, or osteopenia. Methods and kits for the treatment of diseases affected by opening (or lack thereof) of Cx43 hemichannels in osteocytes are also provided. Such methods can include administering to a subject in need thereof a therapeutically effective amount of any one the pharmaceutical formulations disclosed herein.

BRIEF DESCRIPTION OF THE DRAWINGS

(FIG. 2A) and 40±2° C. (FIG. 2B) from the pH/buffer screening study.

(FIG. 3A) and 40±2° C. (FIG. 3B) from the pH/buffer screening study.

(FIG. 4A) and 40±2° C. (FIG. 4B).

(FIG. 5A) and 40±2° C. (FIG. 5B).

(FIG. 12A), 25±2° C. (FIG. 12B) and 40±2° C. (FIG. 12C).

(FIG. 13A), 25±2° C. (FIG. 13B) and 40±2° C. (FIG. 13C).

(FIG. 14A), 25±2° C. (FIG. 14B) and 40±2° C. (FIG. 14C).

FIG. 15: Reduced SDS-Caliper purity % comparison at 2-8° C.

DETAILED DESCRIPTION

Figure 1:
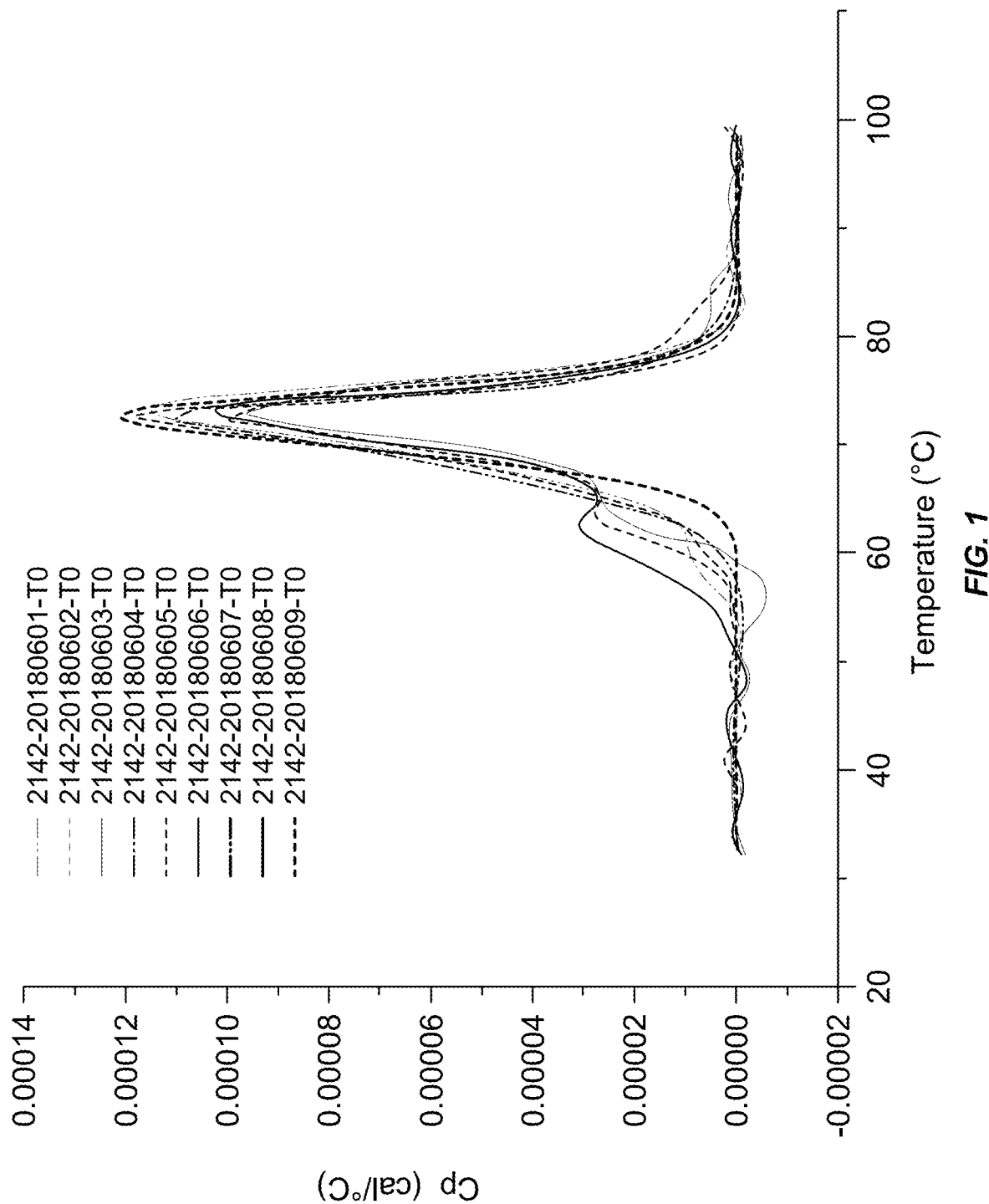
FIG. 1: MicroCal DSC thermogram overlay from the anti-Cx43 Ab pH/Buffer screening study.

Disclosed herein, in some embodiments, is a stable, aqueous pharmaceutical formulation of anti-Cx43 antibodies. Such formulation can include: an anti-Cx43 antibody or antigen binding fragment thereof, a buffer, a surfactant, and a stabilizer. The pharmaceutical formulation can have a pH of between about 5 and about 6, or about 5.4-5.6, or about 5.5.

In some embodiments, the anti-Cx43 antibody or antigen binding fragment thereof can have a first, second and third heavy chain complementarity determining region (CDR) sequence having the amino acid sequence of SEQ ID NOs: 1, 2, and 3, respectively; and/or a first, second and third light chain CDR sequence having the amino acid sequence of SEQ ID NOs: 4, 5, and 6, respectively.

In some embodiments, the anti-Cx43 antibody or antigen binding fragment thereof can have a heavy chain variable domain having the amino acid sequence of SEQ ID NO: 7, and a light chain variable domain having the amino acid sequence of SEQ ID NO: 8.

In certain embodiments, the anti-Cx43 antibody or antigen binding fragment thereof comprises a heavy chain having an amino acid sequence selected from the group consisting of SEQ ID NOs: 9-17, and a light chain having the amino acid sequence of SEQ ID NO: 18.

In certain embodiments, the anti-Cx43 antibody or antigen binding fragment thereof binds to an epitope located within the amino acid sequence of FLSRPTEKTI (SEQ ID NO: 19).

In various embodiments, the formulations disclosed herein can have improved stability, such that they display no significant changes (such as appearance, antibody concentration, pH, antibody aggregation, and antibody purity) observed at a predetermined temperature (e.g., −20° C. or refrigerated temperature of 2-8° C.) for a period of time, e.g., at least 3 months, at least 6 months, at least 1 year, or up to 2 years.

Definitions

Unless defined otherwise, all technical and scientific terms used herein have the same meaning as commonly understood by those of ordinary skill in the art to which this disclosure pertains. The following references provide one of skill with a general definition of many of the terms used in this disclosure: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press ($4^{th}$ ed., 2000). Further clarifications of some of these terms as they apply specifically to this disclosure are provided herein.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

An "anti-Cx43 antibody" is an antibody that immunospecifically binds to Cx43 (e.g., its extracellular domain). The antibody may be an isolated antibody. Such binding to Cx43 exhibits a $K_D$ with a value of, e.g., no greater than 1 µM, no greater than 100 nM or no greater than 50 nM. $K_D$ can be measured by any methods known to one skilled in the art, such as a surface plasmon resonance assay or a cell binding assay. An anti-Cx43 antibody may be a monoclonal antibody, or antigen-binding fragments thereof. In some embodiments, the antibody can be those disclosed in International Application No. PCT/US2019/025363, incorporated herein by reference in its entirety.

An "antibody," as used herein is a protein comprising binding domains that bind to a target epitope. The term antibody includes monoclonal antibodies comprising immunoglobulin heavy and light chain molecules, single heavy chain variable domain antibodies, and variants and derivatives thereof, including chimeric variants of monoclonal and single heavy chain variable domain antibodies. Binding domains are substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. For most vertebrate organisms, including humans and murine species, the typical immunoglobulin structural unit comprises a tetramer that is composed of two identical pairs of polypeptide chains, each pair having one "light" (about 25 kD) and one "heavy" chain (about 50-70 kD). "$V_L$" and "$V_H$" refer to the variable domains of these light and heavy chains respectively. "$C_L$" and "$C_H$" refer to the constant domains of the light and heavy chains. Loops of β-strands, three each on the $V_L$ and $V_H$ are responsible for binding to the antigen, and are referred to as the "complementarity determining regions" or "CDRs". The "Fab" (fragment, antigen-binding) region includes one constant and one variable domain from each heavy and light chain of the antibody, i.e., $V_L$, $C_L$, $V_H$ and $C_H 1$.

Antibodies include intact immunoglobulins as well as antigen-binding fragments thereof. The term "antigen-binding fragment" refers to a polypeptide fragment of an antibody which binds antigen or competes with intact antibody (i.e., with the intact antibody from which they were derived) for antigen binding (i.e., specific binding). Antigen binding fragments can be produced by recombinant or biochemical methods that are well known in the art. Exemplary antigen-binding fragments include Fv, Fab, Fab', (Fab')$_2$, CDR, paratope and single chain Fv antibodies (scFv) in which a $V_H$ and a $V_L$ chain are joined together (directly or through a peptide linker) to form a continuous polypeptide.

Antibodies also include variants, chimeric antibodies and humanized antibodies. The term "antibody variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

As described herein, the amino acid residues of an antibody can be numbered according to the general numbering of Kabat (Kabat, et al. (1991) Sequences of Proteins of Immunological Interest, 5th edition. Public Health Service, NIH, Bethesda, MD).

The term "binding" as used herein in the context of binding between an antibody and an epitope of Cx43 as a target, refers to the process of a non-covalent interaction between molecules. Preferably, said binding is specific. The specificity of an antibody can be determined based on affinity. A specific antibody can have a binding affinity or dissociation constant $K_D$ for its epitope of less than $10^{-7}$ M, preferably less than $10^{-8}$ M.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. In one embodiment, an epitope is a region of an antigen that is bound by an antibody. In certain embodiments, an antibody is said to specifically bind an antigen when it preferentially recognizes its target antigen in a complex mixture of proteins and/or macromolecules. Methods for epitope mapping are well known in the art, such as X-ray co-crystallography, array-based oligo-peptide scanning, site-directed mutagenesis, high throughput mutagenesis mapping and hydrogen-deuterium exchange. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

The term "subject" or "patient" includes a human or other mammalian animal that receives either prophylactic or therapeutic treatment.

The terms "treat," "treating," and "treatment," as used herein, refer to therapeutic or preventative measures such as those described herein. The methods of "treatment" employ administration to a patient a Cx43 ligand provided herein, for example, a patient having a cancer, in order to prevent, cure, delay, reduce the severity of, or ameliorate one or more symptoms of the cancer or recurring cancer, or in order to prolong the survival of a patient beyond that expected in the absence of such treatment. The methods of "treatment" also employ administration to a patient a Cx43 ligand provided herein (e.g., an antibody) to provide cancer therapy in a patient beyond that expected in the absence of such treatment.

The term "cancer" broadly refers to an uncontrolled, abnormal growth of a host's own cells leading to invasion of surrounding tissue and potentially tissue distal to the initial site of abnormal cell growth in the host. Major classes include carcinomas which are cancers of the epithelial tissue (e.g., skin, squamous cells); sarcomas which are cancers of the connective tissue (e.g., bone, cartilage, fat, muscle, blood vessels, etc.); leukemias which are cancers of blood forming tissue (e.g., bone marrow tissue); lymphomas and myelomas which are cancers of immune cells; and central nervous system cancers which include cancers from brain and spinal tissue. "Cancer(s)," "neoplasm(s)," and "tumor(s)" are used herein interchangeably. As used herein, "cancer" refers to all types of cancer or neoplasm or malignant tumors including leukemias, carcinomas and sarcomas, whether new or recurring. Specific examples of cancers are: carcinomas, sarcomas, myelomas, leukemias, lymphomas and mixed type tumors. Non-limiting examples of cancers are new or recurring cancers of the brain, melanoma, bladder, breast, cervix, colon, head and neck, kidney, lung, non-small cell lung, mesothelioma, ovary, prostate, sarcoma, stomach, uterus and medulloblastoma.

The term "effective amount" as used herein, refers to that amount of an agent, such as a Cx43 ligand, for example an anti-Cx43 antibody, which is sufficient to effect treatment, prognosis or diagnosis of a cancer, when administered to a patient. A therapeutically effective amount will vary depending upon the patient and disease condition being treated, the weight and age of the patient, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 Vg to about 2,000, about 400 kg to about 1,175 mg, about 500 kg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 tug, of an antibody or antigen binding portion thereof, as provided herein. Dosing may be, e.g., every week, every 2 weeks, every three weeks, every 4 weeks, every 5 weeks or every 6 weeks. Dosage regimens may be adjusted to provide the optimum therapeutic response. An effective amount is also one in which any toxic or detrimental effects (side effects) of the agent are minimized and/or outweighed by the beneficial effects. Administration may be intravenous at exactly or about 6 mg/kg or 12 mg/kg weekly, or 12 mg/kg or 24 mg/kg biweekly. Additional dosing regimens are described below.

As used herein, "formulation" is a composition of a pharmaceutically active drug, such as a biologically active protein (e.g., antibody), that is suitable for parenteral administration (including but not limited to intravenous, intramuscular, or subcutaneous) to a patient in need thereof and includes only pharmaceutically acceptable excipients, diluents, and other additives deemed safe by the Federal Drug Administration or other foreign national authorities.

As used herein the phrases "liquid formulation" and "aqueous formulation" are used interchangeably to refer to a solution or liquid preparation that contains a biopharmaceutical in combination with one or more excipients (e.g., chemical additives)—dissolved in a suitable solvent.

A "stable" formulation is a pharmaceutical formulation with no significant changes observed at a predetermined temperature (e.g., −20° C. or refrigerated temperature of 2-8° C.) for a period of time, e.g., at least 3 months, at least 6 months, at least 1 year, or up to 2 years. Stability of the formulations disclosed herein can be evaluated using one or more of the following criteria: 1) the aqueous formulation is colorless, or clear to slightly opalescent by visual analysis; 2) the protein content is maintained within +/−5 mg/mL from initial concentration; 3) the pH is maintained within +/−0.2 pH units from target pH, 4) the percent of monomer by SEC is ≥95%; 5) the purity as measured by CE-SDS is ≥90% and the relative potency based on ELISA is within 50-150%.

As used herein the term "excipient" is intended to mean a therapeutically inactive substance. Excipients are included in a formulation for a wide variety of purposes, for example, as a buffer, stabilizer, tonicity agent, surfactant, anti-oxidant, cryoprotectant or diluent.

Suitable excipients include, but are not limited to polyols (also known as sugar alcohols) such as mannitol or sorbitol, sugars such as sucrose, lactose or dextrose, salts such as NaCl, KCl or calcium phosphate, amino acids, for example, histidine, lysine, aspartic acid, or glutamic acid, surfactants, as well as water. The purity of the excipient should meet compendial standards (e.g., USP, EP, JP) and be of sufficient purity for subcutaneous, intramuscular, or intravenous injection into humans.

The term "buffer" or "buffering agent", as used herein, refers to a pharmaceutically acceptable excipient, which stabilizes the pH of a pharmaceutical preparation. Suitable buffers are well known in the art and can be found in the literature. For example, citrate salts, acetate salts, histidine salts, succinate salts, malate salts, phosphate salts or lactate salts, and/or the respective free acids or bases thereof, as well as mixtures of the various salts and/or acids and bases thereof can be employed. In a particular embodiment, pharmaceutically acceptable buffers comprise but are not limited to histidine buffers, citrate buffers, succinate buffers, acetate buffers and phosphate buffers. In a particular embodiment, buffers are acetate buffers, for example, sodium acetate buffer. Other particular buffers are histidine buffers, i.e. buffers having histidine, generally L-histidine, as buffering agent. A particular buffer is L-histidine/HCl buffer, comprising L-histidine or mixtures of L-histidine and L-histidine hydrochloride and pH adjustment achieved with hydrochloric acid. Unless otherwise indicated, the term "L-histidine" when used herein to describe a buffering agent, refers to L-histidine/HCl buffer. L-histidine/HCl buffer can be prepared by dissolving suitable amounts of L-histidine and L-histidine hydrochloride in water, or by dissolving a suitable amount of L-histidine in water and adjusting the pH to the desired value by addition of hydrochloric acid. The abovementioned buffers are generally used at a concentration of about 1 mM to about 100 mM, about 10 mM to about 50 mM, about 15 to 30 mM or 20 mM. Regardless of the buffer used, the pH can be adjusted to a value in the range from about 4.0 to about 7.0, about 5.0 to about 6.0, about 5.4 to about 5.6, or about 5.5, with an acid or a base known in the art, e.g., hydrochloric acid, acetic acid, phosphoric acid, sulfuric acid and citric acid, sodium hydroxide and potassium hydroxide.

The term "surfactant" as used herein denotes a pharmaceutically acceptable, surface-active agent. In a particular embodiment, a non-ionic surfactant is used. Examples of pharmaceutically acceptable surfactants include, but are not limited to, polyoxyethylen-sorbitan fatty acid esters (Tween), polyoxyethylene alkyl ethers (Brij), alkylphenylpolyoxyethylene ethers (Triton X), polyoxyethylene-polyoxypropylene copolymers (Poloxamer, Pluronic), and sodium dodecyl sulphate (SDS). In a particular embodiment, polyoxyethylene-sorbitan fatty acid esters are polysorbate 20 (polyoxyethylene sorbitan monolaureate, sold under the trademark Tween 20™) and polysorbate 80 (polyoxyethylene sorbitan monooleate, sold under the trademark Tween 80™). In a particular embodiment, polyethylene-polypropylene copolymers are those sold under the names Pluronic® F68 or Poloxamer 188™ In a particular embodiment, polyoxyethylene alkyl ethers are those sold under the trademark Brij™ In a particular embodiment, alkylphenylpolyoxyethylene ethers are sold under the tradename Triton X, for example, p-tert-octylphenoxy polyethoxyethanol (sold under the tradename Triton X-100™). When polysorbate 20 (Tween 20™) and polysorbate 80 (Tween 80™) are used, they are generally used at a concentration range of about 0.001 to about 1%, about 0.01 to about 0.01% or about 0.02% to about 0.05%. In the formulation of the disclosure, the concentration of the surfactant is described as a percentage, expressed in weight/volume (w/v).

The term "stabilizer" as used herein denotes a pharmaceutically acceptable excipient, which protects the active pharmaceutical ingredient and/or the formulation from chemical and/or physical degradation during manufacturing, storage and application. Stabilizers include but are not limited to saccharides, amino acids, polyols, e.g. mannitol, sorbitol, xylitol, dextran, glycerol, arabitol, propylene glycol, polyethylene glycol, cyclodextrines, e.g. hydroxypropyl-β-cyclodextrine, sulfobutylethyl-1-cyclodextrine, β-cyclodextrine, polyethylenglycols, e.g. PEG 3000, PEG 3350, PEG 4000, PEG 6000, albumines, e.g. human serum albumin (HSA), bovine serum albumin (BSA), salts, e.g. sodium chloride, magnesium chloride, calcium chloride, chelators, e.g. EDTA as hereafter defined. As mentioned hereinabove, stabilizers can be present in the formulation in an amount of about 1 to about 500 mM, in an amount of about 10 to about 300 mM or in an amount of about 120 mM to about 300 mM. More than one stabilizer, selected from the same or from different groups, can be present in the formulation.

The term "saccharide" as used herein includes monosaccharides and oligosaccharides. A monosaccharide is a monomeric carbohydrate which is not hydrolysable by acids, including simple sugars and their derivatives, e.g. amino-sugars. Saccharides are usually in their D conformation. Examples of monosaccharides include glucose, fructose, galactose, mannose, sorbose, ribose, deoxyribose, neuraminic acid. An oligosaccharide is a carbohydrate consisting of more than one monomeric saccharide unit connected via glycosidic bond(s) either branched or in a linear chain. The monomeric saccharide units within an oligosaccharide can be identical or different. Depending on the number of monomeric saccharide units the oligosaccharide is a di-, tri-, tetra- penta- and so forth saccharide. In contrast to polysaccharides the monosaccharides and oligosaccharides are water soluble. Examples of oligosaccharides include sucrose, trehalose, lactose, maltose and raffinose. In a particular embodiment, saccharides are sucrose and trehalose (i.e. α,α-D-trehalose), for example, sucrose. Trehalose is available as trehalose dihydrate. Saccharides can be present in the formulation in an amount of about 100 to about 500 mM, in an amount of about 200 to about 300 mM or in an amount of about 240 mM.

A subgroup within the stabilizers are lyoprotectants. The term "lyoprotectant" denotes pharmaceutically acceptable excipients, which protect the labile active ingredient (e.g. a protein) against destabilizing conditions during the lyophilisation process, subsequent storage and reconstitution. Lyoprotectants comprise but are not limited to the group consisting of saccharides, polyols (such as e.g. sugar alcohols) and amino acids. In a particular embodiment, lyoprotectants can be selected from the group consisting of saccharides such as sucrose, trehalose, lactose, glucose, mannose, maltose, galactose, fructose, sorbose, raffinose, neuraminic acid, amino sugars such as glucosamine, galactosamine, N-methylglucosamine ("Meglumine"), polyols such as mannitol and sorbitol, and amino acids such as arginine and glycine or mixtures thereof. Lyoprotectants are generally used in an amount of about 10 to 500 mM, in an amount of about 10 to about 300 mM or in an amount of about 100 to about 300 mM.

Another subgroup within the stabilizers are antioxidants. The term "antioxidant" denotes pharmaceutically acceptable excipients, which prevent oxidation of the active pharmaceutical ingredient. Antioxidants comprise but are not limited to ascorbic acid, gluthathione, cysteine, methionine, citric acid, EDTA. Antioxidants can be used in an amount of about 0.01 to about 100 mM, in an amount of about 5 to about 50 mM or in an amount of about 5 to about 25 mM.

The formulations according to the disclosure may also comprise one or more tonicity agents. The term "tonicity agents" denotes pharmaceutically acceptable excipients used to modulate the tonicity of the formulation. The formulation can be hypotonic, isotonic or hypertonic. Isotonicity in general relates to the osmotic pressure of a solution, usually relative to that of human blood serum (around 250-350 mOsmol/kg) The formulation according to the disclosure can be hypotonic, isotonic or hypertonic. In a particular embodiment, the formulation is isotonic. An isotonic formulation is liquid or liquid reconstituted from a solid form, e.g. from a lyophilized form, and denotes a solution having the same tonicity as some other solution with which it is compared, such as physiologic salt solution and the blood serum. Suitable tonicity agents comprise but are not limited to sodium chloride, potassium chloride, glycerine and any component from the group of amino acids or sugars, in particular glucose. Tonicity agents are generally used in an amount of about 5 mM to about 500 mM.

Within the stabilizers and tonicity agents there is a group of compounds which can function in both ways, i.e. they can at the same time be a stabilizer and a tonicity agent. Examples thereof can be found in the group of sugars, amino acids, polyols, cyclodextrines, polyethyleneglycols and salts. An example for a sugar which can at the same time be a stabilizer and a tonicity agent is trehalose.

The "isoelectric point" or "pI" of a protein is the pH at which the protein has a net overall charge equal to zero, i.e., the pH at which the protein has an equal number of positive and negative charges. Determination of the pI for any given protein can be done according to well-established techniques, such as, e.g., by isoelectric focusing. Isoelectric focusing is a technique for separating different molecules by differences in their isoelectric point (pI). It is a type of zone electrophoresis, usually performed on proteins in a gel that takes advantage of the fact that overall charge on the molecule of interest is a function of the pH of its surroundings.

Various aspects of the disclosure are described in further detail below. Additional definitions are set out throughout the specification.

Pharmaceutical Formulations

In some embodiments, the present disclosure provides a pharmaceutical composition comprising an anti-Cx43 antibody, or antigen binding fragment thereof, as described herein. The anti-Cx43 antibody, or antigen binding fragment thereof, can have a first, second and third heavy chain complementarity determining region (CDR) sequence having the amino acid sequence of SEQ ID NOs: 1, 2, and 3, respectively; and a first, second and third light chain CDR sequence having the amino acid sequence of SEQ ID NOs: 4, 5, and 6, respectively.

In some embodiments, the anti-Cx43 antibody or antigen binding fragment thereof can include a heavy chain variable domain having the amino acid sequence of SEQ ID NO: 7, and a light chain variable domain having the amino acid sequence of SEQ ID NO: 8.

In certain embodiments, the anti-Cx43 antibody or antigen binding fragment thereof comprises a heavy chain having an amino acid sequence selected from the group consisting of SEQ ID NOs: 9-17, and a light chain having the amino acid sequence of SEQ ID NO: 18.

In certain embodiments, the anti-Cx43 antibody or antigen binding fragment thereof binds to an epitope located within the amino acid sequence of FLSRPTEKTI (SEQ ID NO: 19).

In some embodiments, the anti-Cx43 antibody or antigen binding fragment thereof can be present at a concentration of between about 5 and about 50 mg/mL, or between 10 and 40, or from about 15 to 30 mg/mL.

In various embodiments, the anti-Cx43 antibody or antigen binding fragment thereof can be formulated in pharmaceutically acceptable amounts and in pharmaceutically acceptable compositions. As used herein, "pharmaceutically acceptable" shall refer to that which is useful in preparing a pharmaceutical composition that is generally safe, non-toxic, and neither biologically nor otherwise undesirable and includes that which is acceptable for veterinary use as well as human pharmaceutical use. Examples of "pharmaceutically acceptable liquid carriers" include water and organic solvents. Preferred pharmaceutically acceptable aqueous liquids include PBS, saline, and dextrose solutions etc.

As used herein, the term "pharmaceutically acceptable salt" means any pharmaceutically acceptable salt of the compounds disclosed herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

Various literature references are available to facilitate selection of pharmaceutically acceptable carriers or excipients. See, e.g., Remington's Pharmaceutical Sciences and U.S. Pharmacopeia: National Formulary, Mack Publishing Company, Easton, Pa. (1984); Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY;

Lieberman et al. (eds.) (1990) Pharmaceutical Dosage Forms: Disperse Systems, Marcel Dekker, NY; Weiner, Wang, W., Int. J. Pharm. 185:129-188 (1999) and Wang, W., Int. J. Pharm. 203:1-60 (2000), and Kotkoskie (2000) Excipient Toxicity and Safety, Marcel Dekker, Inc., New York, N.Y.

In some embodiments, the antibody formulation can comprise a buffer (e.g., histidine, acetate, phosphate or citrate buffer), a surfactant (e.g., poly sorbate), and/or a stabilizer agent (e.g., sucrose), etc.

Buffers are used to control the pH in a range which optimizes the therapeutic effectiveness, especially if stability is pH dependent. Buffers can be present at concentrations ranging from about 50 mM to about 250 mM. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

In certain embodiments, the buffer can be selected from acetate/sodium acetate, histidine/aspartic acid, citric acid/sodium citrate, dibasic sodium phosphate/sodium dihydrogen phosphate, and histidine/histidine hydrochloride. The "/" as used herein when referring to buffer composition "A/B" means that component A and component B (e.g., a salt of component A) are both present. In certain embodiments, the buffer is histidine/aspartic acid or histidine/histidine hydrochloride. In certain embodiments, the buffer is histidine/histidine hydrochloride.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, or about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride. In some embodiments, the surfactant is polysorbate 80 (PS80).

In certain embodiments, the stabilizer is selected from ethylenediaminetetraacetic acid (EDTA), sodium chloride, sorbitol, glycine, and sucrose. In certain embodiments, the stabilizer is sucrose.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinositose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

In some embodiments, the antibody formulation can comprise pharmaceutically acceptable carriers, including, e.g., ion exchangers, alumina, aluminum stearate, lecithin, serum proteins, such as human serum albumin, buffer substances such as phosphates, sucrose, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol. In some embodiments, the antibody formulation further comprises a surfactant. In some embodiments, the surfactant is selected from the group consisting of polysorbate, sodium dodecyl sulfate, and nonionic surfactant.

The formulation according to the disclosure can be in a liquid form, in a lyophilized form or in a liquid form reconstituted from a lyophilized form. In certain embodiments, the formulation is in a liquid form. The term "liquid" as used herein in connection with the formulation according to the disclosure denotes a formulation which is liquid at a temperature of at least about 2 to about 8° C. under atmospheric pressure. The term "lyophilized" as used herein in connection with the formulation according to the disclosure denotes a formulation which is manufactured by freeze-drying methods known in the art per se. The solvent (e.g., water) is removed by freezing followed by sublimation of the ice under vacuum and desorption of residual water at elevated temperature. The lyophiliizate usually has a residual moisture of about 0.1 to 5% (w/w) and is present as a powder or a physically stable cake. The lyophilizate is characterized by a fast dissolution after addition of a reconstitution medium.

The term "reconstituted form" as used herein in connection with the formulation according to the disclosure denotes a formulation which is lyophilized and re-dissolved by addition of reconstitution medium. Suitable reconstitution media comprise but are not limited to water for injection (WFI), bacteriostatic water for injection (BWFI), sodium chloride solutions (e.g. 0.9% (w/v) NaCl), glucose solutions (e.g. 5% glucose), surfactant-containing solutions (e.g. 0.02% polysorbate 80), pH-buffered solutions (eg. phosphate-buffered solutions).

The formulation according to the disclosure is physiologically well tolerated, can be prepared easily, can be dispensed precisely and is stable with respect to decomposition products and aggregates over the duration of storage, during repeated freezing and thawing cycles and mechanical stress. It is stable at storage temperatures (e.g., −20° C. or 2-8° C.) over a period of more than 1 year.

The antibody formulations of the present disclosure can be an aqueous solution. In some embodiments, the antibody formulation has not been subjected to freezing temperatures, and/or have not been frozen, i.e., they have remained in a liquid state. In some embodiments, the antibody in the antibody formulation has not been subjected to lyophilization.

In some embodiments, the antibody formulations disclosed herein have improved stability compared to other formulations. As used herein, the term "stability" generally is related to maintaining the integrity or to minimizing the degradation, denaturation, aggregation or unfolding of a biologically active agent such as a protein, peptide or another bioactive macromolecule. As used herein, "improved stability" generally means that, under conditions known to result in degradation, denaturation, aggregation or unfolding, the protein (e.g., antibody such as anti-Cx43 Ab), peptide or another bioactive macromolecule of interest maintains greater stability compared to a control protein, peptide or another bioactive macromolecule.

In some embodiments, stability refers to an antibody formulation having low to undetectable levels of particle formation. The phrase "low to undetectable levels of particle formation" as used herein refers to samples containing less than 30 particles/mL, less than 20 particles/ml, less than 20 particles/ml, less than 15 particles/ml, less than 10 particles/ml, less than 5 particles/ml, less than 2 particles/ml or less than 1 particle/ml as determined by HIAC analysis or visual analysis. In some embodiments, no particles in the antibody formulation are detected, either by HM-IAC analysis or visual analysis.

In some embodiments, stability refers to reduced fragmentation of the antibody. The term "low to undetectable levels of fragmentation" as used herein refers to samples containing equal to or more than 80%, 85%, 90%, 95%, 98% or 99% of the total protein, for example, in a single peak as determined by HPSEC, or in two peaks (e.g., heavy- and light-chains) (or as many peaks as there are subunits) by reduced Capillary Gel Electrophoresis (rCGE), representing the non-degraded antibody or a non-degraded fragment thereof, and containing no other single peaks having more than 5%, more than 4%, more than 3%, more than 2%, more than 1%, or more than 0.5% of the total protein in each. The term "reduced Capillary Gel Electrophoresis" as used herein refers to capillary gel electrophoresis under reducing conditions sufficient to reduce disulfide bonds in an antibody.

One of skill in the art will appreciate that stability of a protein is dependent on other features in addition to the composition of the formulation. For example, stability can be affected by temperature, pressure, humidity, pH, and external forms of radiation. Thus, unless otherwise specified, stability referred to herein is considered to be measured at −20° C., one atmosphere pressure, 50% relative humidity, pH of 5.5, and normal background levels of radiation. Stability of the antibody in the antibody formulation can be determined by various means. In some embodiments, the antibody stability is determined by size exclusion chromatography (SEC). SEC separates analytes (e.g., macromolecules such as proteins and antibodies) on the basis of a combination of their hydrodynamic size, diffusion coefficient, and surface properties. Thus, for example, SEC can separate antibodies in their natural three-dimensional conformation from antibodies in various states of denaturation, and/or antibodies that have been degraded. In SEC, the stationary phase is generally composed of inert particles packed into a dense three-dimensional matrix within a glass or steel column. The mobile phase can be pure water, an aqueous buffer, an organic solvent, mixtures of these, or other solvents. The stationary-phase particles have small pores and/or channels which will only allow species below a certain size to enter. Large particles are therefore excluded from these pores and channels, but the smaller particles are removed from the flowing mobile phase. The time particles spend immobilized in the stationary-phase pores depends, in part, on how far into the pores they can penetrate. Their removal from the mobile phase flow causes them to take longer to elute from the column and results in a separation between the particles based on differences in their size.

In some embodiments, SEC is combined with an identification technique to identify or characterize proteins, or fragments thereof. Protein identification and characterization can be accomplished by various techniques, including but not limited chromatographic techniques, e.g., high-performance liquid chromatography (HPLC), immunoassays, electrophoresis, ultra-violet/visible/infrared spectroscopy, raman spectroscopy, surface enhanced raman spectroscopy, mass spectroscopy, gas chromatography, static light scattering (SLS), Fourier Transform Infrared Spectroscopy (FTIR), circular dichroism (CD), urea-induced protein unfolding techniques, intrinsic tryptophan fluorescence, differential scanning calorimetry, and/or ANS protein binding.

In some embodiments, protein identification is achieved by high-pressure liquid chromatography. Various instruments, and apparatuses are known to those of skill in the art to perform HPLC. Generally, HPLC involves loading a liquid solvent containing the protein of interest onto a separation column, in winch the separation occurs. The HPLC separation column is filled with solid particles (e.g. silica, polymers, or sorbents), and the sample mixture is separated into compounds as it interacts with the column particles. HPLC separation is influenced by the liquid solvent's condition (e.g. pressure, temperature), chemical interactions between the sample mixture and the liquid solvent (e.g. hydrophobicity, protonation, etc.), and chemical interactions between the sample mixture and the solid particles packed inside of the separation column (e.g. ligand affinity, ion exchange, etc.).

In some embodiments, the SEC and protein identification occurs within the same apparatus, or simultaneously. For example, SEC and HPLC can be combined, often referred to as SE-HPLC.

Stability of the antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have solubility in water (at 20° C.) of at least about 20 mg/ml, alternatively at least about 100 mg/ml, alternatively at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated C2-9 carboxylic acids (e.g., aliphatic mono-, di- and tri-carboxylic acids). For example, exemplary monocarboxylic acids within this definition include the saturated C2-9 monocarboxylic acids acetic, proprionic, butyric, valeric, caproic, enanthic, caprylic pelargonic and capryonic, and the unsaturated C2-9 monocarboxylic acids acrylic, propriolic methacrylic, crotonic and isocrotonic acids. Exemplary dicarboxylic acids include the saturated C2-9 dicarboxylic acids malonic, succinic, glutaric, adipic and pimelic, while unsaturated C2-9 dicarboxylic acids include maleic, fumaric, citraconic and mesaconic acids. Exemplary tricarboxylic acids include the saturated C2-9 tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this disclosure include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

In some embodiments, the aqueous formulation comprises about 2 mg/ml to about 100 mg/ml antibody wherein the antibody comprises a heavy chain variable region and a light chain variable region, wherein the heavy chain variable region comprises the Kabat-defined CDR1, CDR2, and CDR3 sequences of SEQ ID NOs: 1-3, and wherein the light chain variable region comprises the Kabat-defined CDR1, CDR2, and CDR3 sequences of SEQ ID NOs: 4-6, wherein said formulation is stable upon storage at about 40° C. for at least 1 month. In some embodiments, the formulation is stable upon storage at about 25° C. for at least 3 months. In some embodiments, the formulation is stable upon storage at about 5° C. for at least 6 months. In some embodiments, the formulation is stable upon storage at about 5° C. for at least 12 months. In some embodiments, the formulation is stable upon storage at about 5° C. for at least 18 months. In some embodiments, the formulation is stable upon storage at about 5° C. for at least 24 months, or 36 months.

The term "stable" can be relative and not absolute. Thus, in some embodiments the antibody is stable if less than 20%, less than 15%, less than 10%, less than 5% or less than 2% of the antibody is degraded, denatured, aggregated or unfolded as determined by SEC HPLC when the antibody is stored −20° C. for 6 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at −20° C. for 12 months. In some embodiments, the antibody in the antibody formulation is stable if less than 20%, less than 15%, less than 10%, less than 5% or less than 2% of the antibody is degraded, denatured, aggregated or unfolded as determined by SEC HPLC when the antibody is stored at −20° C. for 18 months. In some embodiments, the antibody in the antibody formulation is stable if less than 20%, less than 15%, less than 10%, less than 5% or less than 2% of the antibody is degraded, denatured, aggregated or unfolded as determined by SEC HPLC when the antibody is stored at −20° C. for 24 months.

In some embodiments, the antibody is stable if less than 20%, less than 15%, less than 10%, less than 5% or less than. 2% of the antibody is degraded, denatured, aggregated or unfolded as determined by SEC HPLC when the antibody is stored at 23° C. to 27° C. for 3 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 6 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 12 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23' C to 27° C. for 24 months.

In some embodiments the antibody is stable if less than 6%, less than 4%, less than 3%, less than 2% or less than 1% of the antibody is degraded, denatured, aggregated or unfolded per month as determined by SEC HPLC when the antibody is stored at 40° C. In some embodiments the antibody is stable if less than 6%, less than 4%, less than 3%, less than 2% or less than 1% of the antibody is degraded, denatured, aggregated or unfolded per month as determined by SEC HPLC when the antibody is stored at 5° C.

In some embodiments, the antibody formulations of the present disclosure can be considered stable if the antibody exhibits very little to no loss of the binding activity of the antibody (including antibody fragments thereof) of the formulation compared to a reference antibody as measured by antibody binding assays know to those in the art, such as, e.g., ELISAs, etc., over a period of 8 weeks, 4 months, 6 months, 9 months, 12 months or 24 months. In some embodiments, the antibody stored at about 40° C. for at least 1 month retains at least 60%, at least 80%, at least about 85%, at least about 90%, at least about 95%, at least about 98%, or at least about 99% of binding ability to Cx43 compared to a reference antibody which has not been stored. In some embodiments, the antibody stored at about 5° C. for at least 6 months retains at least 80%, at least about 85%, at least about 90%, at least about 95%, at least about 98%, or at least about 99% of binding ability to Cx43 compared to a reference antibody which has not been stored. In some embodiments, the antibody stored at about 40° C. for at least 1 month retains at least 95% of binding ability to Cx43 compared to a reference antibody which has not been stored. In some embodiments, the antibody stored at about 5° C. for at least 6 months retains at least 95% of binding ability to Cx43 compared to a reference antibody which has not been stored.

The antibody formulations can provide low to undetectable levels of aggregation of the antibody. The phrase "low to undetectable levels of aggregation" as used herein refers to samples containing no more than about 5%, no more than about 4%, no more than about 3%, no more than about 2%, no more than about 1% and no more than about 0.5% aggregation by weight of protein as measured by high performance size exclusion chromatography (HPSEC) or static light scattering (SLS) techniques. In some embodiments, less than 2% of the antibody forms an aggregate upon storage at about 40° C. for at least 4 weeks as determined by as determined by HPSEC. In some embodiments, less than 2% of the antibody forms an aggregate upon storage at about 5° for at least 3 months, at least 6 months, at least 9 months, at least 12 months, at least 15 months, at least 18 months, at least 24 months, or at least 36 months as determined by IPSEC.

It has been discovered herein the antibody formulations provided herein result in greatly reduced particle formation as determined by visual inspection, micro-flowing imaging (MF), or size-exclusion chromatography (SEC). In some embodiments, the formulation is substantially free of particles upon storage at about 40° C. for at least 1 month as determined by visual inspection. In some embodiments, the formulation is substantially free from particles upon storage at about 5° C. for at least 6 months, at least 9 months, at least 12 months, at least 15 months, at least 18 months, at least 24 months, or at least 36 months as determined by visual inspection.

The formulations may also contain adjuvants such as preservatives, wetting agents, emulsifying agents and dispersing agents. Prevention of presence of microorganisms may be ensured both by sterilization procedures, and by the inclusion of various antibacterial and antifungal agents, e.g. paraben, chlorobutanol, phenol, sorbic acid, and the like. Preservatives are generally used in an amount of about 0.001 to about 2% (w/v). Preservatives comprise but are not limited to ethanol, benzyl alcohol, phenol, m-cresol, p-chlorm-cresol, methyl or propyl parabens, benzalkonium chloride.

The antibody formulations described herein can have various viscosities. Methods of measuring viscosity of antibody formulations are known to those in the art, and can include, e.g., a rheometer (e.g., Anton Paar MCR301 Rheometer with either a 50 mm, 40 mm or 20 mm plate accessory). In some embodiments of the present disclosure, the viscosities were reported at a high shear limit of 1000 per second shear rate. In some embodiments, the antibody formulation has a viscosity of less than 20 centipoise (cP), less than 18 cP, less than 15 cP, less than 13 cP, or less than 11 cP. In some embodiments, the antibody formulation has a viscosity of less than 13 cP. One of skill in the art will appreciate that viscosity is dependent on temperature, thus, unless otherwise specified, the viscosities provided herein are measured at 25° C. unless otherwise specified.

The antibody formulations can have different osmolarity concentrations. Methods of measuring osmolarity of antibody formulations are known to those in the art, and can include, e.g., an osmometer (e.g., an Advanced Instrument Inc 2020 freezing point depression osmometer). In some embodiments, the formulation has an osmolarity of between 200 and 600 mosm/kg, between 260 and 500 mosm/kg, or between 300 and 450 mosm/kg.

The antibody formulation of the present disclosure can have various pH levels. In some embodiments, the pH of the antibody formulation is between 4 and 7, between 4.5 and 6.5, between 5 and 6, or between 5.4 to 5.6. In some embodiments, the pH of the antibody formulation is 5.5. In some embodiments, the pH of the antibody formulation is 6.0. In some embodiments, the pH of the antibody formulation is ≥7.0. Various means may be utilized in achieving the desired pH level, including, but not limited to the addition of the appropriate buffer.

In some embodiments, the antibody formulation can include: about 10-50 mg/mL, or about 25 mg/mL of an anti-Cx43 antibody or antigen binding fragment thereof; about 10-40 mM, or about 20 mM histidine/histidine hydrochloride buffer; about 0.005%-0.05%, or about 0.02% w/v Polysorbate 80; and about 1%-20% w/v, or about 8% w/v sucrose; wherein the formulation has a pH of between about 5.4 to about 5.6, or about 5.5.

In some embodiments, the antibody formulation can include: about 25 mg/mL an anti-Cx43 antibody or antigen binding fragment thereof, comprising a heavy chain having an amino acid sequence selected from the group consisting of SEQ ID NOs: 9-17, and comprising a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 9 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 10 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 11 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 12 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 13 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 14 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 14 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 15 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 16 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In one embodiment, the antibody formulation can include: about 25 mg/mL an anti-Cx43 antibody or antigen binding fragment thereof, comprising a heavy chain having an amino acid sequence of SEQ ID NO: 17 and a light chain having the amino acid sequence of SEQ ID NO: 18; about 20 mM histidine/aspartic acid buffer; about 0.02% w/v Polysorbate 80; and about 8% w/v sucrose, wherein the formulation has a pH of between about 5.4 to about 5.6, or about 5.5.

In some embodiments, the disclosure provides a kit comprising any of the antibody formulations described herein, the containers described herein, the unit dosage forms described herein, or the pre-filled syringe described herein.

Therapeutic Uses

In some embodiments, the antibody formulation of the present disclosure can be used for pharmaceutical purposes. Antibodies used in pharmaceutical applications generally must have a high level of purity, especially in regard to contaminants from the cell culture, including cellular protein contaminants, cellular DNA contaminants, viruses and other transmissible agents. See "WHO Requirements for the use of animal cells as in vitro substrates for the production of biologicals: Requirements for Biological Substances No. 50." No. 878. Annex 1, 1998. In response to concerns about contaminants, The World Health Organization (WHO) established limits on the levels of various contaminants. For example, the WHO recommended a DNA limit of less than 10 ng per dose for protein products. Likewise, the United States Food and Drug Administration (FDA) set a DNA limit of less than or equal to 0.5 pg/mg protein. Thus, in some embodiments, the present disclosure is directed to antibody formulations meeting or exceeding contaminant limits as defined by one or more governmental organizations, e.g., the United States Food and Drug Administration and/or the World Health Organization.

The antibody formulation of the present disclosure can be administered to a subject through various means. In some embodiments, the antibody formulation is suitable for parenteral administration, e.g., via inhalation (e.g., powder or aerosol spray), transmucosal, intravenous, subcutaneous, or intramuscular administration. In some embodiments, the formulation is an injectable formulation. In some embodiments, the disclosure is directed to a sealed container comprising any of the antibody formulations as described herein.

In some aspects, the present disclosure is directed to various pharmaceutical dosage forms. Various dosage forms could be applicable to the formulations provided herein. See, e.g., Pharmaceutical Dosage Form: Parenteral Medications, Volume 1, $2^{nd}$ Edition. In one embodiment, a pharmaceutical unit dosage of the disclosure comprises the antibody formulation in a suitable container, e.g. a vial or syringe. In one embodiment, a pharmaceutical unit dosage of the disclosure comprises an intravenously, subcutaneously, or intramuscularly delivered antibody formulation. In another embodiment, a pharmaceutical unit dosage of the disclosure comprises aerosol delivered antibody formulation. In a specific embodiment, a pharmaceutical unit dosage of the disclosure comprises a subcutaneously delivered antibody formulation. In another embodiment, a pharmaceutical unit dosage of the disclosure comprises an aerosol delivered antibody formulation. In a further embodiment, a pharmaceutical unit dosage of the disclosure comprises an intranasally administered antibody formulation.

A composition of the present disclosure can be administered by a variety of methods known in the art. As will be appreciated by the skilled artisan, the route and/or mode of administration will vary depending upon the desired results.

To administer a composition of the disclosure by certain routes of administration, it may be necessary to dilute the composition in a diluent. Pharmaceutically acceptable diluents include saline, glucose, Ringer and aqueous buffer solutions.

In a particular embodiment, the formulation according to the disclosure is administered by intravenous (i.v.), subcutaneous (s.c.) or any other parental administration means such as those known in the pharmaceutical art.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. The composition must be sterile and fluid to the extent that the composition is deliverable by syringe or an infusion system. In addition to water, the carrier can be an isotonic buffered saline solution, ethanol, polyol (e.g., glycerol, propylene glycol, and liquid polyethylene glycol, and the like), and suitable mixtures thereof.

The formulation according to the disclosure can be prepared by methods known in the art, e.g., ultrafiltration-diafiltration, dialysis, addition and mixing, lyophilisation, reconstitution, and combinations thereof. Examples of preparations of formulations according to the disclosure can be found hereinafter.

The pharmaceutical composition as described herein may be used in treatment of cancer, cancer metastasis, osteosarcoma, osteoporosis, or osteopenia.

Cancer metastasis occurs when a cancer spreads from the part of the body where it originated (e.g., breast or prostate) to other parts of the body (e.g., liver or bone) and establishes a secondary tumor. The bone is one of the most common sites of cancer metastasis. Cancers that metastasize to bone include, but are not limited to breast cancer, prostate cancer, lung cancer, and skin cancers (e.g., melanoma). Bone metastasis can be identified in up to 75% of patients with advanced breast and prostate cancers. Bone metastasis are associated with many significant clinical and quality of life consequences, such as, but not limited to intractable pain, pathological fractures, spinal cord and nerve compression, bone marrow infiltration, and impaired motility. In many cases the systemic presence of a cancer can also make the cancer incurable.

Osteosarcoma is the most common primary bone malignancy and accounts for 60% of all malignant childhood bone tumors. Before multi-agent chemotherapy, amputation provided a long-term survival rate of only about 20%. Since the 1970s, combination chemotherapy along with limb-sparing surgery has been the main treatment for osteosarcoma. Currently, the 5-year survival for patients with osteosarcoma has been reported to be 50% to 80%. However, this survival rate has not improved over the last 10 years, and fully 40% of osteosarcoma patients die of their disease.

Osteoporosis is a systemic skeletal disease characterized by low bone mass and microarchitectural deterioration of bone tissue, with a consequent increase in bone fragility and susceptibility to fracture. Any bone can be affected by osteoporosis, although the hip, spine, and wrist are common bones that are broken or fractured in subjects suffering from or at risk for osteoporosis.

Osteoporosis in postmenopausal Caucasian women is defined as a value for bone mineral density (BMD) of >2.5 SD below the young average value, i.e. a T-score of 2.5 SD. Severe osteoporosis (established osteoporosis) uses the same threshold, but with one or more prior fragility fractures. The preferred site for diagnostic purposes are BMD measurements made at the hip, either at the total hip or the femoral neck. For men, the same threshold as utilized for women is appropriate, since for any given BM D, the age adjusted fracture risk is more or less the same.

Osteopenia is a pre-osteoporosis condition characterized as a mild thinning of bone mass which is not as severe as osteoporosis. Osteopenia results when the formation of bone is not enough to offset normal bone loss. Osteopenia is generally considered the first step towards osteoporosis. Diminished bone calcification can also be referred to as osteopenia, whether or not osteoporosis is present.

EXAMPLES

The following examples are presented so as to provide those of ordinary skill in the art with a complete disclosure and description of how to make and use the compositions and methods and are not intended to limit the scope of what the inventors regard as their invention.

Example 1: Materials and Methods

Abbreviations

| Abbreviation | Full name |
|---|---|
| Caliper_NR | Non-Reduced CE-SDS Caliper |
| Caliper_R | Reduced CE-SDS Caliper |
| cIEF | Capillary Isoelectric Focusing |
| DS | Drug substance |
| DP | Drug product |
| FT | Freeze/Thaw |
| HIAC | Particle matter |
| HMW | High Molecular Weight |
| LMW | Low Molecular Weight |
| MFI | Micro Flowing Imaging/Microfluidic Imaging |
| mM | Millimoles/Liter |
| MW | Molecular Weight |
| NA | Not Applicable |
| ND | Not Detected |
| Ph.Eur. | European Pharmacopoeia |
| pI | Isoelectric Point |
| PS80 | Polysorbate 80 |
| rpm | Round Per Minute/Revolution Per Minute |
| RT | Room Temperature |
| SDS-Caliper | Caliper-Sodium Dodecyl Sulfate |
| SDS-CE-R | Reduced Capillary Electrophoresis-Sodium Dodecyl Sulfate |
| SDS-CE-NR | Non-Reduced Capillary Electrophoresis-Sodium Dodecyl Sulfate |
| SEC-HPLC | Size Exclusion High Performance Liquid Chromatography |
| USP | United States Pharmacopoeia |
| w/v | Weight/Volume |
| A | Agitation |
| C | Cycle |
| D | Day |
| M | Month |
| T0 | Time 0 |
| W | Week |

Equipment

| Description | Vendor | Model |
|---|---|---|
| Agilent HPLC | Agilent Technologies Singapore (Sales)Pt | 1260 series (1260/1290) |
| Centrifuge | Eppendorf | Centrifuge 5804R |
| Clarity Detector | Tianda Tianfa | YB-2 |
| Drug Storage Box | Haier | HYC-940 |
| Electronic Balance | Mettler Toledo | MS6002S/0/MS1003S/01/XS205 |
| MFI | ProteinSimple | 5200 |
| Modulated Differential Scanning Calorimetry | TA Instruments-Waters LLC | DSC Q2000 |
| Osmometer | Advanced Instruments. INC | Advanced 2020 |
| pH Meter | Mettler Toledo | S40 |
| Refrigerator | Haier | HYC-940/DW-40L508 |
| Refrigerator | Eppendorf | U725 |
| Safety Hood | Shanghai Shangjing | BSC-II-A2 |
| Safety Hood | Sujing Sutai | BSC-II-A2 |
| Thermostat Shaker | Shanghai Tiancheng | TS-200B |
| Stability Chamber | MMM | Climacell 707 |
| Ultra-low Temperature Freezer | Eppendorf | U725 |
| UV spectrophotometer | Thermo Scientific | NanoDrop 2000 |

Reagents

| Reagent | Grade | Vendor | Catalog # | Lot # |
| --- | --- | --- | --- | --- |
| L-Histidine | Multi-Compendial | J. T. Baker | 2080-06 | 0000090914 |
| L-Histidine-monohydrochloride | Multi-Compendial | J. T. Baker | 2081-06 | 0000179922 |
| Aspartic acid | ph Eur/USP | AppliChem | A1701, 1000 | 6T012474 |
| Sodium dihydrogen phosphate dihydrate | ph Eur/BP/USP/JPE/E339 | Merck | 1.06345.9026 | K93518945 |
| Di-sodium hydrogen phosphate dihydrate | ph Eur/BP/USP | Merck | 1.06576.9029 | K45710476 |
| Citric Acid Monohydrate | ph Eur/BP/JP/USP/E330 | Merck | 1.00242.5000 | K48745442711 |
| Tri-Sodium Citrate Dihydrate | ph Eur/BP/JP/USP/E331 | Merck | 1.06432.5000 | K93697932 |
| Acetic Acid | EP/BP/JP/USP | J. T. Baker | 9526-03 | 0000084970 |
| Sodium Acetate, Trihydrate | bio ph Eur/BP/JP/USP | Merck | 1.37012.9029 | AM1027312 |
| EDTA | USP | J. T. Baker | 8995-01 | 0000172864 |
| NaCl | EP/BP/USP/JP | Merck | 1.16224.5000 | K47447424 |
| Polysorbate 80 | Multi-Compendial | NOF | NA | 704352A |
| Sucrose | Multi-Compendial | Pfanstiehl | S-124-1-MC | 36920A |
| Glycine | CHP | Tianjin Tianyao | NA | AGLY160124 |
| Sorbitol | USP | Merck | 1.11597.2500 | M852697705 |

| Description | Vendor | Catalog # | Lot # |
| --- | --- | --- | --- |
| 20 mL Ultrafiltration centrifuge tube | Sartorius Stedim | VS2022 | 1709032VS/1802014VS |
| 2 R Vial | Schott (Suzhou) | V002711080D | 6104481548 |
| 6 R Vial | Schott (Suzhou) | V006111112C/1142196 | 6104358817 |
| 13 mm Rubber Stopper | West (U.S.) | 1970-0004 | D000063205 |
| 20 mm Rubber Stopper | West (Singapore) | 7002-2354 | 3172022309 |
| 13 mm Plastic-aluminum cap | West (U.S.) | 5413-0921 | 0000928228 |
| 20 mm Plastic-aluminum cap | West (India) | 5420-3627 | 00001235077 |

These anti-Cx43 Ab formulation development studies were aimed to develop feasible and stable liquid formulations that support long-term storage of the anti-Cx43 Ab drug product. The studies included pH/Buffer screening, excipients and PS80 strength screening. The impact of buffer system, pH, excipients and PS80 on product stability was evaluated through freeze/thaw, agitation and accelerated stability studies.

The pH/Buffer screening study indicated that the anti-Cx43 Ab was more stable in 20 mM histidine/histidine hydrochloride buffer at pH 5.5 and in 20 mM histidine/aspartic acid buffer at pH 5.5 versus other buffer candidates studied.

The excipients and PS80 strength screening studies showed that the anti-Cx43 Ab in histidine buffer with sucrose was relatively more stable than that with sodium chloride, sorbitol or glycine. The addition of PS80 significantly improved the stability of the anti-Cx43 Ab at an optimal concentration of 0.02%, while the addition of EDTA showed insignificant improvement on the stability of anti-Cx43 Ab.

25 mg/mL anti-Cx43 Ab in 20 mM histidine/histidine hydrochloride at pH 5.5 with 8% sucrose and 0.02% (w/v) PS80 was selected for the formulation confirmation study.

Sample Number Management Rules

Sample Number: PPP-YYYYMIMNN-X-CC-TT

PPP represents the numerical part of the project name (this project is 2142). YYYY, MM and NN represent the year, the month and the serial number of sample preparation in this month, respectively.

X represents the testing condition. For example, FT and A represent freeze-thaw and agitation, respectively.

CC represents the testing temperature. For example, 05, 25 and 40 represent 2~8° C., 25° C. and 40° C., respectively.

TT represents the testing time. For example, T0, 7D, 4W and 1M represent the start time, 7 days, 4 weeks and 1 months, respectively.

F represents the formulation number. For example, F1 and F2 represent formulation 1 and formulation 2, respectively.

For instance: 2142-20180601-25-4W represented the first sample of project anti-Cx43 Ab prepared in June 2018. The sample was stored upright at 25° C. for 4 weeks.

Analytical Methods

Appearance

The appearance of samples, including clarity, color, and visible particles, was examined against a black and white background using a YB-2 light box.

pH

The pH was measured using a Mettler Toledo S40 pH Meter. The pH meter was calibrated prior to use.

Osmolality

Osmolality was measured using an Advanced 2020 Multi-Sample Osmometer using 20 μL of sample. The testing accuracy of the osmometer was confirmed with a 290 mOsmol/kg reference.

MFI

A Microflow Imaging (MFI) system was used for sub-visible particle analysis. According to the user's manual, the MFI test was performed with more than 1.3 mL samples. The MFI data was analyzed with the MVAS software. The final data was reported as the total particle number at different size ranges.

Particulate Matter

A HACH Particulate Analyzer was utilized to measure the sub-visible particle size and counts under a laminar flow cabinet. To avoid introducing air bubbles and interference during examination, all samples were held in the cabinet for at least 0.5 hr before testing. Each sample was tested for four consecutive runs, 1 mL each. The results were presented as average number of particles of ≥10 μm and ≥25 μm per mL (method conforms to USP <788> Particulate matter in injections).

Protein Concentration

Protein concentration was determined by a Thermo UV spectrophotometer. According to the Lambert-Beer law, the relationship of the absorbance value (A) of the protein solution at a particular ultraviolet wavelength, the protein concentration (c), optical path (b) and extinction coefficient (ε) is in accord with the following formula: $A=\varepsilon*b*c$ (A is the absorbance value, ε is the absorbance coefficient, b is the optical path and c is the concentration). The extinction coefficient of anti-Cx43 Ab is 1.531 $AU*mL*mg^{-1}*cm^{-1}$. UV absorption at 280 nm was measured using a Nanodrop 2000 spectrophotometer.

DSC

Differential scanning calorimetry (DSC) was utilized to measure the thermal stability of proteins by detecting the heat capacity of sample in heat flow. Specifically, DSC was used to measure the thermal transition midpoint (Tm) and onset of melting (Tmonset), which are indicators of the relative stability of the protein in solution. Samples were diluted to 1 mg/mL with a reference buffer. An aliquot of 400 μL of reference buffer was added into each odd-numbered well of a 96-well plate while an aliquot of 400 μL of each sample was added into the corresponding even-numbered well. The scanning temperature ranged from 20° C. to 100° C. with a scan rate of 200° C./hr. Data analysis was performed using MicroCal VP Capillary DSC Automated data analysis software 2.0.

mDSC

Modulated Differential Scanning Calorimetry (mDSC) is performed for instance by using a DSC-Q2000 system (TA instruments-Waters LLC). Tzero aluminum crucibles and Tzero aluminum lid, all from TA instruments, were used to contain the sample to be measured and to seal the crucible by means of a Tzero press. An empty Tzero crucible was similarly prepared and used as a reference. Approximately 10 μL DS was added, pressed flat and transferred in a Tzero crucible sealed with a Tzero lid by means of a Tzero press. The calibration scanning program was equilibrated at −60.00° C. for 5 min, then was run at a constant temperature rate of 5.00° C./min to 10.00° C. Data acquisition and processing were performed with the help of Universal Analysis Software package.

cIEF

The method of Imaged Capillary Isoelectric focusing (iCIEF) separates proteins based on their charge differences in a pH gradient. Under an external electric field, the charge variants of monoclonal antibodies migrate along a continuous pH gradient formed by ampholyte additives. The charge variant will stop at where the pH equals to its pI. The pI value and relative abundance of the resolved peaks can be identified and quantified with software. The master mix was prepared with the following proportion (for one sample amount): 0.5 μL pI 7.05 marker; 0.5 μL pI 9.22 marker; 4 μL Pharmalyte 3-10; 35 μL 1% Methylcellulose; 40 μL $H_2O$. The solution for one sample injection was composed of 20 μL of 1.0 mg/mL diluted sample and 80 μL of master mix.

SDS-Caliper (Reduced and Non-Reduced)

SDS-Caliper is a high throughput chip based method which separates proteins mainly by their molecular size. Before each sample was tested, pretreatment, such as incubation with sample buffer, SDS and N-ethylmaleimide (for non-reduced) or dithiothreitol (for reduced) at 70° C. for 10 min was necessary. The loading mix with a minimum volume of 42 μL (final protein concentration of 0.045 mg/mL) was then tested by LabChip GXII Touch at excitation/emission wavelengths of 635 and 700 nm. The final results were analyzed by Empower software.

Cation Exchange Chromatography (CEX)

CEX measures the charge heterogeneity of a monoclonal antibody solution by separating proteins according to differences in their net charge number in a buffered solution. Samples in low salt buffer, at a pH below the isoelectric point will have a net positive charge and will adsorb on the chromatographic resin which is negatively charged. A pH gradient is used to elute the different protein species off based on charge heterogeneity, with the most positively charged species binding the strongest and therefore requiring the higher pH. The different eluted charged species are detected by ultraviolet absorbance at 280 nm. The percentage of main peak, acid peak and basic peak of the samples are determined by the method of peak area normalization. CEX was performed on an Agilent 1260 series Infinity system and a propac WCX-10 column. The mobile phase A used here was 16 mM 2-Methylpiperazine, 16 mM Imidazole, 16 mM Tris, pH 5.0±0.1. The mobile phase B was 16 mM 2-Methylpiperazine, 16 mM Imidazole, 16 mM Tris, 80 mM NaCl, pH=10.9±0.1. And the flow rate was set as 1 mL/min. Samples were diluted to 1 mg/mL with mobile phase A and 100 μL of samples were eluted by gradient increasing the amount of mobile phase B. Detection wavelength was set at 280 nm. The running time was 60 minutes.

CE-SDS (Reduced and Non-Reduced)

Non-reduced Capillary Electrophoresis-Sodium Dodecyl Sulfate (CE-SDS) is a purity analysis method that separates proteins based on their electrophoretic mobility, where proteins of smaller sizes move faster and larger sizes move slower. In this method, the diluted protein sample is first alkylated by N-ethylmaleimide (NEM) to prevent thermally induced fragmentation, then denatured with SDS before being injected into an uncoated capillary filled with a viscous SDS gel solution. Components of different molecule sizes in the protein samples are detected as they pass through the capillary with PDA detector at 220 nm.

Briefly, non-reduced CE-SDS was performed using a Beckman Coulter PA800 Enhanced or a PA800 Plus instrument equipped with a photodiode array detector. Samples were diluted to 4 mg/mL by Dilution Solution (PB-CA), and then heated in the presence of 75 μL SDS sample buffer and 5 μL 100 mM NEM at 60° C. for 10 min for non-reduced CE-SDS. Samples were injected using −5 kV for 20 s followed by separation at −15 kV for 35 min. Detection was performed at 220 nm.

Reduced Capillary Electrophoresis-Sodium Dodecyl Sulfate (CE-SDS) is a purity analysis method that separates proteins based on their electrophoretic mobility, where proteins of smaller sizes move faster and larger sizes move slower. In this method, the diluted protein sample is first denatured with SDS then reduced with β-Mercaptoethanol (BME) before being injected into an uncoated capillary filled with a viscous SDS gel solution. Components of different molecule sizes in the protein samples are detected as they pass through the capillary with PDA detector at 220 nm.

Briefly, reduced CE-SDS was performed using a Beckman Coulter PA800 Enhanced or PA800 Plus instrument equipped with a photodiode array detector. Samples were diluted to 4 mg/mL by Dilution Solution (PB-CA), and then heated in the presence of 75 μL SDS sample buffer and 5 μL 2-mercaptoethanol at 70° C. for 10 min for reduced CE- SDS. Samples were injected using −5 kV for 20 s followed by separation at −15 kV for 35 min. Detection was performed at 220 nm.

SEC-HPLC

Size exclusion chromatography (SEC) is a purity analysis method that separates proteins based on their size. Following separation, the relative percentages of HMW species, monomer and LMW species are quantified via UV detection. SEC was performed as follows: If the sample was above 10 mg/mL, it was diluted to 10 mg/mL with mobile phase before SEC analysis. 100 μg of sample was injected into an Agilent 1260 HPLC system equipped with a TSKgel G3000SWXL column (7.8×300 mm, 5 μm particle size) and a UV detector (detection wavelength: 280 nm). The mobile phase was 50 mM phosphate buffer with 300 mM Sodium Chloride (pH 6.8±0.1). An isocratic gradient was applied for 20 min at a flow rate of 1 mL/min.

Example 2: pH/Buffer Screening

The pH/Buffer screening study was to determine the optimal pH/buffer systems for the anti-Cx43 Ab drug product formulation. The goal of this study was to select one pH/buffer system with maximum stabilizing capability for the anti-Cx43 Ab drug product for further formulation development studies.

Nine pH/buffer systems were designed based on the molecule pI and the application of buffer systems. anti-Cx43 Ab DS (Lot: 2142S180507Y) formulated in 20 mM histidine/histidine hydrochloride buffer at pH 5.5 was generated from 50 L pool. The DS was then exchanged into 9 prepared buffers by ultra-filtration centrifugation, respectively. The anti-Cx43 Ab concentration in this study was 25 mg/mL. Samples were stored at 25±2° C. and 40±2° C. for up to 4 weeks. Samples were retrieved timely at each time point and kept at 2~8° C. before analysis. Testing items including appearance, pH, Conc_UV280, SEC-HPLC, cIEF, SDS-Caliper (R&NR), DSC were performed in this study. The sampling plan is listed in Table 1.

TABLE 1

Study Parameters from the anti-Cx43 Ab pH/Buffer Screening

| pH/buffer No. | Sample No. | Buffer System | pH | Time 0 | 2 W | Stored at 25 ± 2° C. 4 W (opt) | 2 W | Stored at 40 ± 2° C. 4 W (opt) |
|---|---|---|---|---|---|---|---|---|
| B1 | 2142-20180601 | 20 mM Acetate | 5.0 | x, y, z | x | x, z | x | x, z |
| B2 | 2142-20180602 | 20 mM Histidine/ Aspartic acid | 5.0 | x, y, z | x | x, z | x | x, z |
| B3 | 2142-20180603 | | 5.5 | x, y, z | x | x, z | x | x, z |
| B4 | 2142-20180604 | 20 mM Citrate | 5.5 | x, y, z | x | x, z | x | x, z |
| B5 | 2142-20180605 | | 6.0 | x, y, z | x | x, z | x | x, z |
| B6 | 2142-20180606 | 20 mM Histidine | 5.5 | x, y, z | x | x, z | x | x, z |
| B7 | 2142-20180607 | | 6.0 | x, y, z | x | x, z | x | x, z |
| B8 | 2142-20180608 | | 6.5 | x, y, z | x | x, z | x | x, z |
| B9 | 2142-20180609 | 20 mM Phosphate | 7.0 | x, y, z | x | x, z | x | x, z |

Notes:
x = Appearance; SEC-HPLC; cIEF; SDS-Caliper (R&NR);
y = DSC;
z = pH; Conc UV280;
(opt) = optional.

An ultra-filtration centrifugal device (30,000 MWCO PES, VIVASPIN 20) was used to perform buffer-exchange of anti-Cx43 Ab DS. Nine pH/buffer systems were used to screen for the optimal buffer system. Table 1 shows the detailed buffer systems. Multiple rounds of ultrafiltration were performed until the exchange rate exceeded 98%. Then the protein concentration was adjusted to 25 mg/mL with the corresponding pH/buffer systems. Each sample was filtered through a 0.22 μm filter (Millipore Express PES Membrane) and then distributed into 2R vials with 1 mL/vial filling volume. Vials were immediately stoppered, sealed and labeled after filling. All the filtration, filling and sealing operations were conducted in a bio-safety hood.

The appropriate number of vials for each pH/buffer system sample were placed in 25±2° C. and 40±2° C. stability chambers, respectively. Samples were drawn and analyzed at pre-determined time points.

Thermograms of anti-Cx43 Ab in different buffer systems are shown in FIG. 1. The Tm onset, the temperature at which mAbs start to unfold, was considered an indicator for the overall thermal stability.

As shown in Table 2, the B2 and B8 samples had lower Tm Onset than the others. This 20 indicated that the thermal stability of anti-Cx43 Ab was not significantly influenced by other pH/buffer systems except B2 and B8.

TABLE 2

DSC data from the anti-Cx43 Ab pH/Buffer screening study

| pH/buffer No. | pH/ Buffer | Tm Onset (° C.) | Tm1 (° C.) | Tm2 (° C.) |
|---|---|---|---|---|
| B1 | A5.0 | 59.8 | 65.6 | 73.0 |
| B2 | H-D5.0 | 52.3 | 62.6 | 72.4 |
| B3 | H-D5.5 | 57.9 | 65.3 | 72.9 |
| B4 | C5.5 | 58.9 | 66.4 | 72.5 |
| B5 | C6.0 | 57.6 | 72.6 | / |
| B6 | H5.5 | 57.0 | 64.0 | 72.1 |
| B7 | H6.0 | 60.0 | 67.3 | 73.2 |
| B8 | H6.5 | 55.2 | 69.5 | 73.5 |
| B9 | P7.0 | 62.4 | 72.4 | / |

Notes:
A5.0: 20 mM acetate/sodium acetate buffer at pH 5.0; H-D-5.0: 20 mM histidine/aspartic acid buffer at pH 5.0; H-D-5.5: 20 mM histidine/aspartic acid buffer at pH 5.5; C5.5: citric acid/sodium citrate buffer at pH 5.5; C6.0: citric acid/sodium citrate buffer at pH 6.0; H5.5: 20 mM histidine/histidine hydrochloride buffer at pH 5.5; H6.0: 20 mM histidine/histidine hydrochloride buffer at pH 6.0; H6.5: 20 mM histidine/histidine hydrochloride buffer at pH 6.5; P7.0: 20 mM dibasic sodium phosphate/sodium dihydrogen phosphate buffer at pH 7.0.

The appearance, protein concentration and pH results of anti-Cx43 Ab in different buffer systems are summarized in Table 3 and Table 4.

The concentration of 9 samples were about 25 mg/mL and the pH values were around the target pH. All the samples were colorless, slightly opalescent and free of visible particle at T0, while the opalescent level of the B4, B5 and B9 samples were deeper than the others. After 2 weeks of storage at 25±2° C. and 40±2° C., slightly visible particles were found in all samples due to the absence of PS80.

This data suggested that the anti-Cx43 Ab was relatively more stable in the B1, B2, B3, B6, B7 and B8 pH/buffer systems than other candidates.

TABLE 3

Protein concentration and pH results from the pH/Buffer screening study

| pH/buffer No. | pH/Buffer | Protein concentration mg/mL T0 | 25-4 W | 40-4 W | pH T0 | 25-4 W | 40-4 W |
|---|---|---|---|---|---|---|---|
| B1 | A5.0 | 24.6 | 24.9 | 25.0 | 5.1 | 5.2 | 5.1 |
| B2 | H-D5.0 | 24.8 | 25.0 | 24.8 | 5.1 | 5.2 | 5.2 |
| B3 | H-D5.5 | 25.0 | 25.0 | 25.3 | 5.5 | 5.6 | 5.6 |
| B4 | C5.5 | 25.3 | 25.4 | 25.3 | 5.5 | 5.4 | 5.4 |
| B5 | C6.0 | 25.9 | 25.8 | 25.8 | 5.9 | 5.8 | 6.0 |
| B6 | H5.5 | 26.0 | 26.1 | 26.1 | 5.5 | 5.7 | 5.6 |
| B7 | H6.0 | 25.2 | 25.4 | 25.3 | 6.0 | 6.1 | 6.1 |
| B8 | H6.5 | 24.9 | 25.2 | 25.1 | 6.5 | 6.5 | 6.5 |
| B9 | P7.0 | 25.6 | 25.7 | 25.7 | 7.0 | 6.9 | 6.9 |

TABLE 4

Appearance results from the pH/Buffer screening study

| pH/buffer No. | pH/Buffer | Appearance T0 | 25-2 W | 25-4 W | 40-2 W | 40-4 W |
|---|---|---|---|---|---|---|
| B1 | A5.0 | A* | B* | B | B | B |
| B2 | H-D5.0 | A | B | B | B | B |
| B3 | H-D5.5 | A | B | B | B | B |
| B4 | C5.5 | A | B | B | B | B |
| B5 | C6.0 | A | B | B | B | B |
| B6 | H5.5 | A | B | B | B | B |
| B7 | H6.0 | A | B | B | B | B |
| B8 | H6.5 | A | B | B | B | B |
| B9 | P7.0 | A | B | B | B | B |

Notes:
A = Colorless, slightly opalescent and free of visible particle;
B = Colorless, slightly opalescent and slightly visible particles.

Figure 2A:
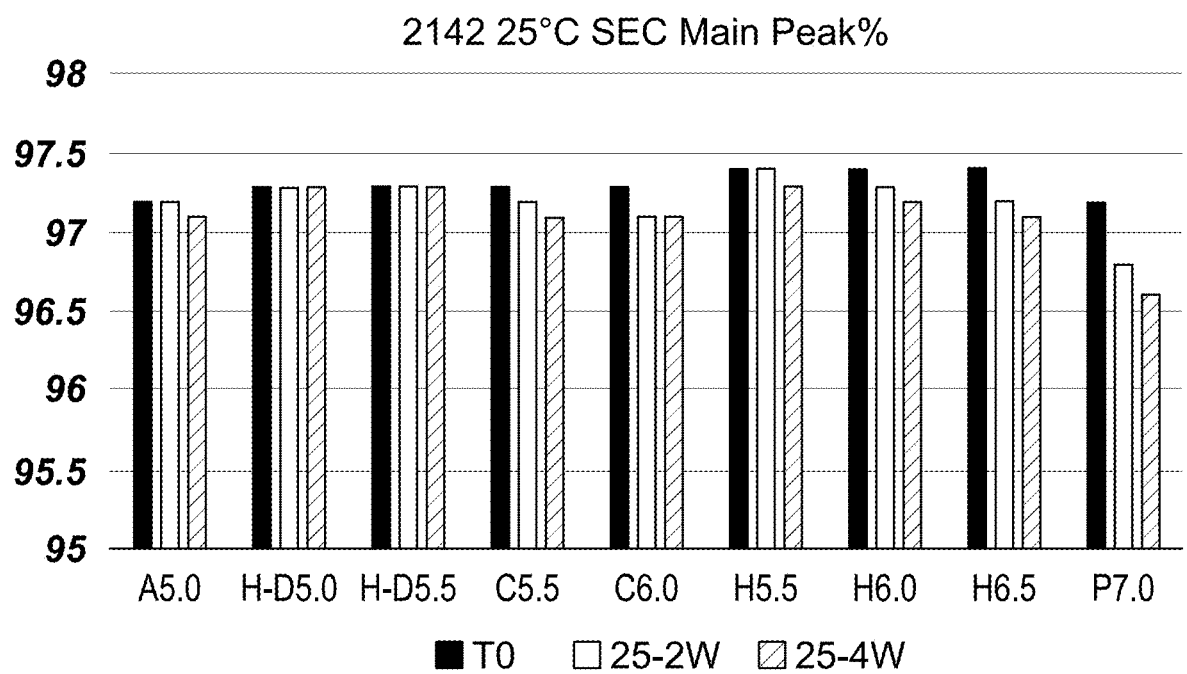
FIGS. 2A-2B: SEC-Main peak % comparison at 25±2° C.
Figure 2B:
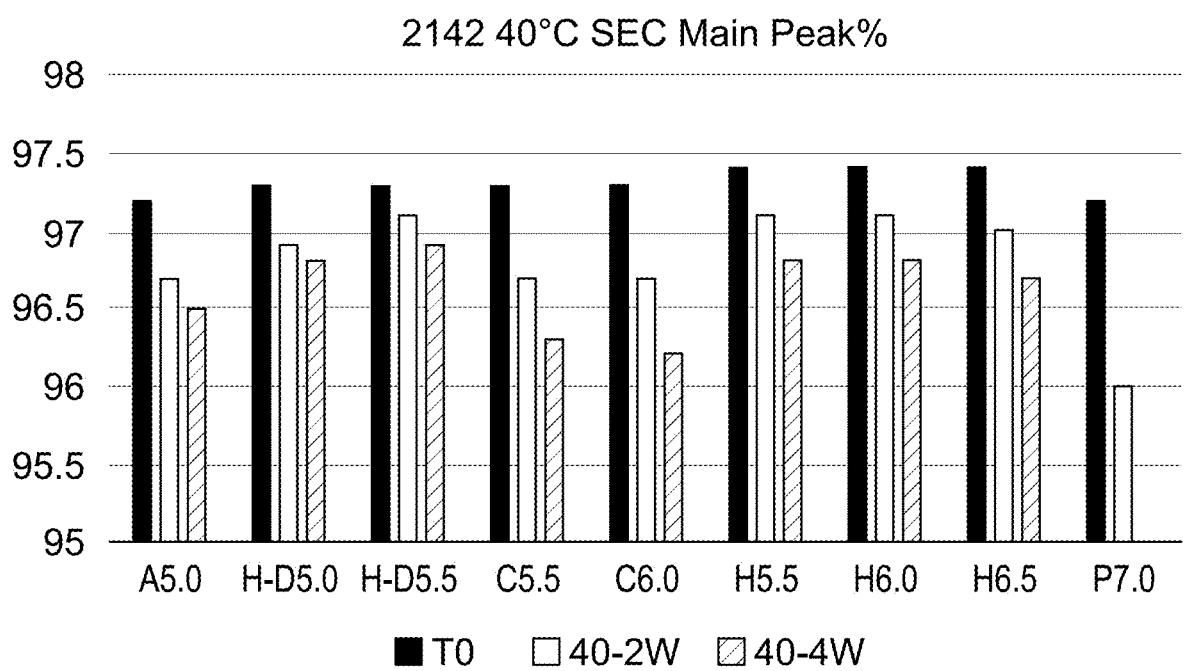

The SEC-HPLC results for all samples are shown in Table 5 and FIG. 2.

All samples had comparable SEC purity with the main peak around 970 at T0. After incubation at 25° C. for 4 weeks, the main peak purity of all samples displayed no obvious decrease. Slight decrease of the main peaks was observed after 2 weeks of storage at 40° C. After incubation at 40° C. for 4 weeks, the decline of the main peaks was in the range of 0.40%~2.4%. Differentiation between samples was not significant except for B9. The purity decline in the B9 sample was 2.4%.

The SEC data indicated that the anti-Cx43 Ab was relatively more stable in B2, B3 and B6.

TABLE 5

SEC-HPLC results from the pH/Buffer screening study

Figure 3A:
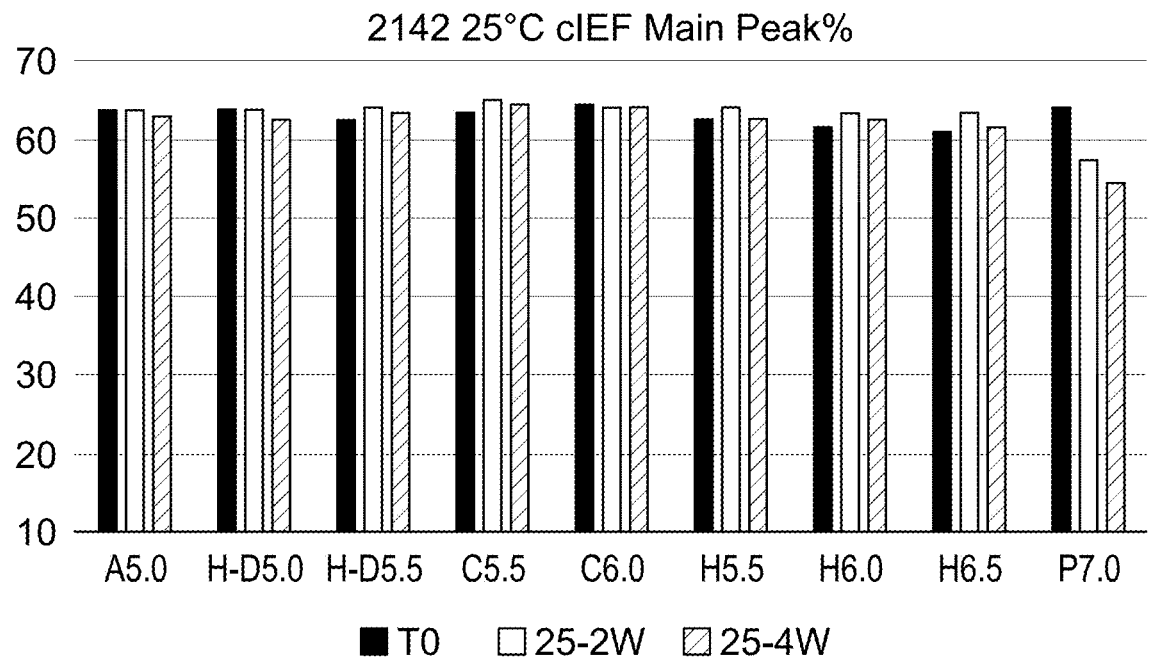
FIGS. 3A-3B: Comparison of cIEF main peak % at 25±2° C.
Figure 3B:
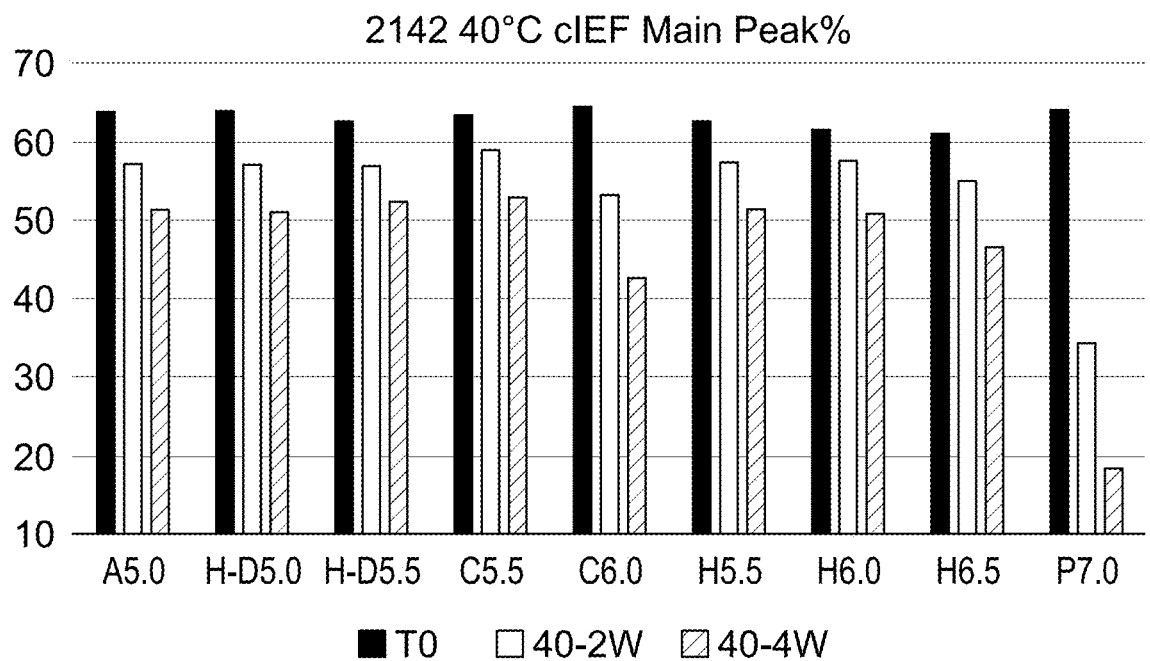

| Purity | pH/buffer No. | SEC-HPLC results T0 | 25-2 W | 25-4 W | 40-2 W | 40-4 W |
|---|---|---|---|---|---|---|
| Main peak % | B1 | 97.2 | 97.2 | 97.1 | 96.7 | 96.5 |
|  | B2 | 97.3 | 97.3 | 97.3 | 96.9 | 96.8 |
|  | B3 | 97.3 | 97.3 | 97.3 | 97.1 | 96.9 |
|  | B4 | 97.3 | 97.2 | 97.1 | 96.7 | 96.3 |
|  | B5 | 97.3 | 97.1 | 97.1 | 96.7 | 96.2 |
|  | B6 | 97.4 | 97.4 | 97.3 | 97.1 | 96.8 |
|  | B7 | 97.4 | 97.3 | 97.2 | 97.1 | 96.8 |
|  | B8 | 97.4 | 97.2 | 97.1 | 97.0 | 96.7 |
|  | B9 | 97.2 | 96.8 | 96.6 | 96.0 | 94.8 |
| HMW peak % | B1 | 2.8 | 2.8 | 2.9 | 3.2 | 3.5 |
|  | B2 | 2.7 | 2.7 | 2.7 | 3.0 | 3.2 |
|  | B3 | 2.7 | 2.7 | 2.7 | 2.9 | 3.1 |
|  | B4 | 2.7 | 2.8 | 2.9 | 3.3 | 3.7 |
|  | B5 | 2.7 | 2.9 | 2.9 | 3.3 | 3.7 |
|  | B6 | 2.6 | 2.7 | 2.7 | 3.0 | 3.2 |
|  | B7 | 2.6 | 2.7 | 2.8 | 2.9 | 3.1 |
|  | B8 | 2.6 | 2.8 | 2.9 | 3.0 | 3.3 |
|  | B9 | 2.8 | 3.3 | 3.4 | 4.0 | 5.1 |
| LMW peak % | B1 | ND | ND | ND | 0.1 | ND |
|  | B2 | ND | ND | ND | 0.1 | 0.1 |
|  | B3 | ND | ND | ND | ND | ND |
|  | B4 | ND | ND | ND | ND | ND |
|  | B5 | ND | ND | ND | ND | 0.1 |
|  | B6 | ND | ND | ND | ND | ND |
|  | B7 | ND | ND | ND | ND | ND |
|  | B8 | ND | ND | ND | ND | ND |
|  | B9 | ND | ND | ND | ND | ND | cIEF was used to determine the isoelectric point (pI) and charge variant distribution of anti-Cx43 Ab. The cIEF results for all samples are shown in Table 6 and FIG. 3.

The pI value of all samples was about 8.1 with insignificant changes under different conditions.

After storage at 25±2° C. for 4 weeks, the main peaks of all the samples declined slightly.

The main peak decline of the B9 sample was 9.7%, which was the greatest among all samples.

After storage at 40±2° C. for 4 weeks, the main peaks of all samples significantly declined, together with significantly increased acidic peaks. The main peaks of B5, B8 and B9 were decreased to 42.6%, 46.6% and 18.5%, respectively. In contrast, the main peak declines of B3, B4 were relatively milder than that of other samples.

The cIEF data indicated that the anti-Cx43 Ab was relatively more stable in B3 and B4.

TABLE 6 cIEF results from the pH/buffer screening study

| Purity | pH/buffer No. | cIEF results T0 | 25-2 W | 25-4 W | 40-2 W | 40-4 W |
|---|---|---|---|---|---|---|
| Main peak % | B1 | 63.7 | 63.8 | 62.8 | 57.1 | 51.4 |
|  | B2 | 63.7 | 63.9 | 62.4 | 57.0 | 51.0 |
|  | B3 | 62.5 | 64.0 | 63.4 | 56.9 | 52.3 |
|  | B4 | 63.6 | 65.2 | 64.5 | 59.1 | 52.9 |
|  | B5 | 64.4 | 64.1 | 64.1 | 53.2 | 42.6 |
|  | B6 | 62.6 | 64.0 | 62.4 | 57.0 | 51.3 |
|  | B7 | 61.7 | 63.5 | 62.4 | 57.7 | 50.6 |
|  | B8 | 61.0 | 63.5 | 61.7 | 55.0 | 46.6 |
|  | B9 | 64.2 | 57.6 | 54.5 | 34.4 | 18.5 |

TABLE 6-continued cIEF results from the pH/buffer screening study

| Purity | pH/buffer No. | cIEF results | | | |
|---|---|---|---|---|---|
| | | T0 | 25-2 W | 25-4 W | 40-2 W | 40-4 W |
| Acidic peak % | B1 | 22.3 | 21.5 | 21.9 | 25.0 | 30.8 |
| | B2 | 23.1 | 21.5 | 22.9 | 26.1 | 30.7 |
| | B3 | 23.7 | 21.8 | 22.0 | 26.8 | 32.3 |
| | B4 | 22.6 | 21.1 | 20.8 | 24.6 | 30.8 |
| | B5 | 22.7 | 22.4 | 22.2 | 31.9 | 43.2 |
| | B6 | 24.8 | 22.5 | 22.9 | 26.5 | 32.5 |
| | B7 | 25.4 | 22.9 | 23.4 | 27.6 | 35.4 |
| | B8 | 26.0 | 22.9 | 24.2 | 29.3 | 37.0 |
| | B9 | 23.0 | 28.7 | 31.7 | 49.9 | 63.7 |
| Basic peak % | B1 | 14.0 | 14.7 | 15.3 | 17.9 | 17.8 |
| | B2 | 13.2 | 14.6 | 14.8 | 16.9 | 18.3 |
| | B3 | 13.8 | 14.2 | 14.6 | 16.3 | 15.4 |
| | B4 | 13.8 | 13.8 | 14.7 | 16.3 | 16.3 |
| | B5 | 12.9 | 13.5 | 13.8 | 14.9 | 14.2 |
| | B6 | 12.5 | 13.6 | 14.7 | 16.1 | 16.2 |
| | B7 | 12.9 | 13.6 | 14.1 | 14.7 | 14.1 |
| | B8 | 13.0 | 13.5 | 14.1 | 15.7 | 16.4 |
| | B9 | 12.8 | 13.8 | 13.8 | 15.7 | 17.8 |

Figure 4A:
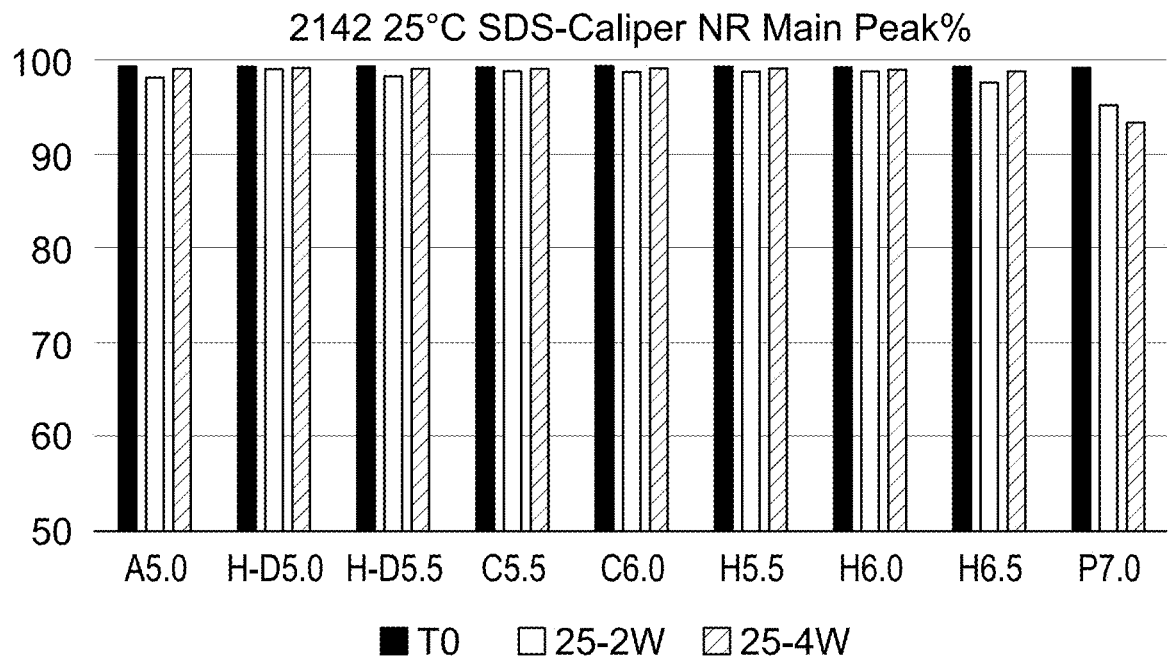
FIGS. 4A-4B: Non-reduced SDS-Caliper purity % comparison from the pH/Buffer screening study at 25±2° C.
Figure 4B:
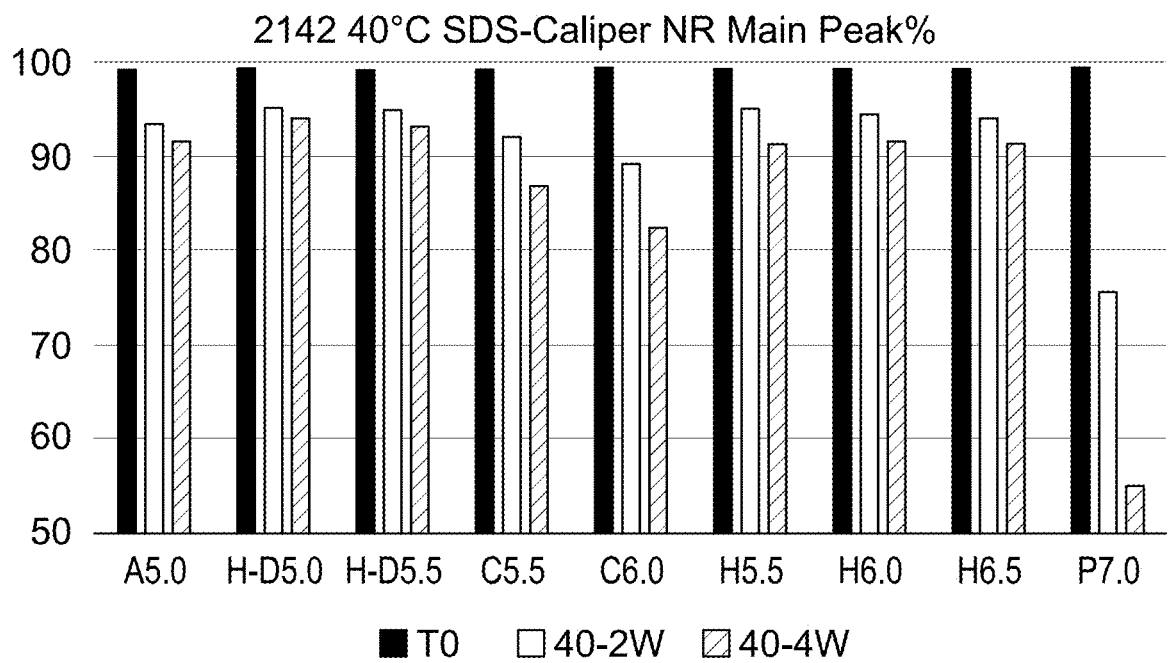
Figure 5A:
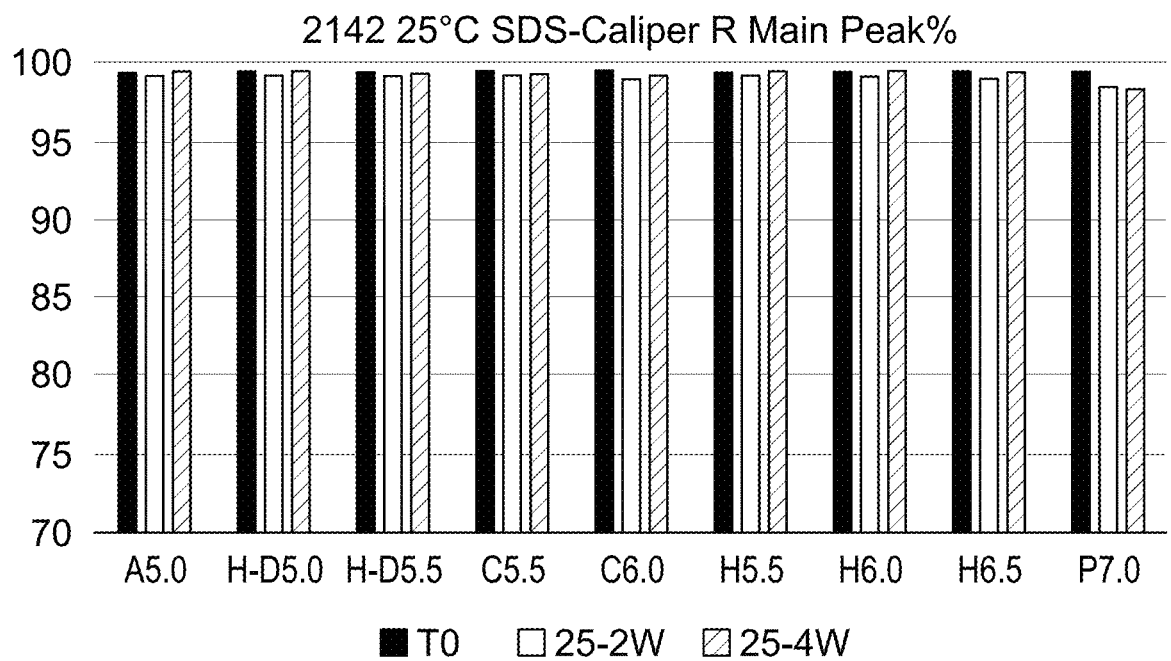
FIGS. 5A-5B: Reduced SDS-Caliper purity % comparison from the pH/Buffer screening study at 25±2° C.
Figure 5B:
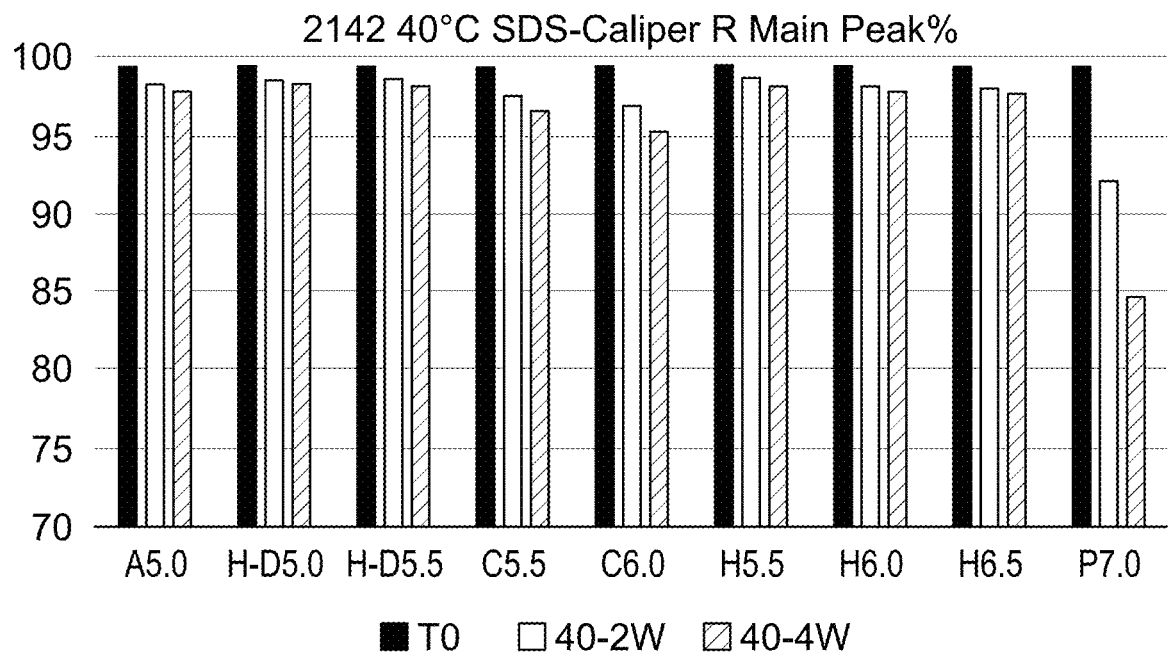

The SDS-Caliper results for all samples are shown in Table 7, FIG. 4 and FIG. 5.

There were no significant changes in non-reduced SDS-Caliper purity and reduced SDS-Caliper purity for all samples after storage at 25±2° C. for 4 weeks.

After 4 weeks of storage at 40±2° C., the non-reduced SDS-Caliper purity of B4, B5 and B9 declined to 86.9%, 82.5% and 55.2%, respectively, which were greater than other samples. The main peak declines of B2 and B3 were relatively milder than that of other samples. The reduced SDS-Caliper purity of all samples declined slightly except B4, B5 and B9.

The SDS-Caliper data indicated that the anti-Cx43 Ab was relatively more stable in B2, B3 and B6.

In this study, 9 samples in varying pH/buffer systems were designed and incubated at 25±2° C. and 40±2° C. On the basis of all the results, the performance of B6 (20 mM histidine/histidine hydrochloride buffer at pH 5.5) and B2 (20 mM histidine/aspartic acid buffer at pH 5.0) were better than other samples. In conclusion, 20 mM histidine/histidine hydrochloride buffer at pH 5.5 (B36) would be used as a lead pH/buffer system and 20 mM histidine/aspartic acid buffer at pH 5.0 (B32) would be used as a backup pH/buffer system for further studies.

Example 3: Excipients and PS80 Strength Screening

The aim of the excipients and PS80 strength screening study was to identify the most stabilizing excipients and evaluate the optimal strength of PS80 for the anti-Cx43 Ab in candidate buffer systems.

20 mM histidine/histidine hydrochloride buffer at pH 5.5 (B6) was chosen for a combinational study of the addition of sodium chloride, sorbitol, glycine, sucrose, PS80 and EDTA. 20 mM histidine/aspartic acid buffer system at pH 5.0 (B2) was used as a backup buffer for the excipients and PS80 strength screening study. Eight formulations were designed as listed in Table 8.

TABLE 7

SDS-Caliper results from the pH/Buffer screening study

| pH/buffer No. | Non-reduced SDS-Caliper Purity % | | | | | Reduced SDS-Caliper Purity % | | | | |
|---|---|---|---|---|---|---|---|---|---|---|
| | T0 | 25-2 W | 25-4 W | 40-2 W | 40-4 W | T0 | 25-2 W | 25-4 W | 40-2 W | 40-4 W |
| B1 | 99.4 | 98.4 | 99.1 | 93.4 | 91.8 | 99.5 | 99.1 | 99.4 | 98.3 | 97.9 |
| B2 | 99.4 | 99.1 | 99.1 | 95.1 | 94.1 | 99.5 | 99.2 | 99.4 | 98.6 | 98.4 |
| B3 | 99.5 | 98.3 | 99.1 | 95.0 | 93.2 | 99.5 | 99.1 | 99.3 | 98.6 | 98.2 |
| B4 | 99.4 | 98.8 | 99.2 | 92.1 | 86.9 | 99.4 | 99.1 | 99.3 | 97.5 | 96.6 |
| B5 | 99.4 | 98.8 | 99.0 | 89.4 | 82.5 | 99.4 | 99.0 | 99.2 | 96.9 | 95.4 |
| B6 | 99.4 | 98.8 | 99.2 | 95.2 | 91.4 | 99.4 | 99.1 | 99.4 | 98.6 | 98.2 |
| B7 | 99.5 | 98.8 | 99.2 | 94.6 | 91.7 | 99.4 | 99.1 | 99.4 | 98.2 | 97.9 |
| B8 | 99.4 | 97.9 | 99.1 | 94.0 | 91.4 | 99.4 | 99.0 | 99.4 | 98.1 | 97.7 |
| B9 | 99.5 | 95.3 | 93.6 | 75.6 | 55.2 | 99.4 | 98.5 | 98.4 | 92.1 | 84.8 |

TABLE 8

Formulation candidates list from the excipients and PS80 strength screening study

| Form. No. | Sample No. | pH/ Buffer | PS80 (w/v) | EDTA (w/v) | NaCl (mM) | Sorbitol (mM) | Glycine (mM) | Sucrose (w/v) |
|---|---|---|---|---|---|---|---|---|
| F1 | 2142-20180801 | H5.5 | 0.02% | / | 150 | / | / | / |
| F2 | 2142-20180802 | | | / | / | 245 | / | / |
| F3 | 2142-20180803 | | | / | / | / | 260 | / |
| F4 | 2142-20180804 | | | / | / | / | / | 8% |
| F5 | 2142-20180805 | | | 0.002% (0.068 mM) | / | / | / | 8% |
| F6 | 2142-20180806 | | 0.05% | / | / | / | / | 8% |
| F7 | 2142-20180807 | | / | / | / | / | / | 8% |
| F8 | 2142-20180808 | H-D-5.5 | 0.02% | 0.002% | / | / | / | 8% |

Notes:
H5.5: 20 mM histidine/histidine hydrochloride buffer at pH 5.5;
H-D-5.0: 20 mM histidine/aspartic acid buffer at pH 5.0.

Formulations were frozen/thawed (−40±5° C./RT) for 5 cycles, agitated at 300 rpm at 25° C. for 7 days, and stored at 2~8° C., 25±2° C. and 40±2° C. for 4 weeks, respectively. Samples were retrieved timely at each time point and kept at 2~8° C. before analysis. Testing items including appearance, pH, Conc_UV280, SEC-HPLC, cIEF, SDS-Caliper (R&NR) and MFI were performed for this study. Table 9 shows the sampling conditions for the excipients and PS80 strength screening study.

TABLE 9

Sampling and testing plan from the anti-Cx43 Ab excipients and PS80 strength screening

| Form. No. | T0 | −40 ± 5° C./ RT Freeze/ Thaw 5 C | 300 rpm Agitation 25° C. 7 D | 2~8° C. 4 W (8 W) | 25 ± 2° C. 2 W | 25 ± 2° C. 4 W | 40 ± 2° C. 2 W | 40 ± 2° C. 4 W |
|---|---|---|---|---|---|---|---|---|
| F1~F8 | x, y, z | x | x | x (x) | x | x | x | x |

Notes:
x = Appearance, pH, SEC-HPLC, cIEF, MFI, SDS-Caliper;
z = Conc_UV280, Osmolality;
( ) = optional.

anti-Cx43 Ab DS (Lot: 21425180507Y) formulated in 20 mM histidine/histidine hydrochloride buffer at pH 5.5 was generated from 50 L pool. The components of each final target formulation were calculated and prepared as described in Table 8. An ultra-filtration centrifugal device (30,000 MWCO PES, VIVASPIN 20) was used to perform buffer-exchange of anti-Cx43 Ab DS. Multiple rounds of ultrafiltration were performed until the exchange rate exceeded 98%. The protein concentration was then adjusted to 25 mg/mL using the corresponding formulation buffers. Each formulation was filtered through a 0.22 μm filter (Millipore Express PES Membrane) and then distributed into 6R vials with 4 mL/vial filling volume. Vials were immediately stoppered and sealed after filling. All the filtration, filling and sealing operations were conducted in a bio-safety hood.

The appropriate number of vials for each formulation were placed and tested as described in Table 9. Samples were drawn and analyzed at pre-determined time points.

The appearance, protein concentration, osmolality and pH value results from the freeze/thaw studies are summarized in Table 10.

The protein concentration and osmolality were all around the target value at T0.

The pH value of 8 samples were all around the target value after 5 freeze/thaw cycles (−40±5° C./RT). The samples were all colorless, slightly opalescent and free of visible particle at T0. After 5 freeze/thaw cycles (−40±5° C./RT), a large number of visible particles were found in the F7 sample due to the absence of PS80. The opalescent level of F1 samples got deeper after 5 freeze/thaw cycles (−40±5° C./RT).

This data suggested that anti-Cx43 Ab was relatively more stable in F2, F4, F5, F6 and F8.

TABLE 10

Protein concentration, pH, osmolality and appearance results from the freeze/thaw study

| No. | Protein concentration mg/mL T0 | Osmolality mOsm/kg T0 | pH T0 | pH FT-5 C | Appearance T0 | Appearance FT-5 C |
|---|---|---|---|---|---|---|
| F1 | 25.7 | 323 | 5.7 | 5.6 | A* | A |
| F2 | 25.5 | 301 | 5.7 | 5.5 | A | A |
| F3 | 25.6 | 298 | 5.7 | 5.5 | A | A |
| F4 | 25.8 | 327 | 5.6 | 5.4 | A | A |
| F5 | 25.7 | 320 | 5.6 | 5.4 | A | A |
| F6 | 25.7 | 316 | 5.6 | 5.5 | A | A |
| F7 | 25.7 | 324 | 5.6 | 5.4 | A | C |
| F8 | 24.1 | 302 | 5.6 | 5.5 | A | A |

Notes:
A = Colorless, slightly opalescent and free of visible particle;
C = Colorless, slightly opalescent and a large number of visible particles The MFI results of freeze/thaw are summarized in Table 11.

The particle counts in F7 were much higher than others at T0 and after 5 freeze/thaw cycles (−40±5° C./RT).

TABLE 11

MFI results from the freeze/thaw study

| Formulation No. | MFI (Counts/mL) | | | | | |
|---|---|---|---|---|---|---|
| | ECD ≥ 2 μm | | ECD ≥ 10 μm | | ECD ≥ 25 μm | |
| | T0 | FT-5 C | T0 | FT-5 C | T0 | FT-5 C |
| F1 | 635 | 4476 | 7 | 19 | 0 | 0 |
| F2 | 2040 | 3138 | 10 | 9 | 0 | 2 |
| F3 | 3266 | 8473 | 5 | 15 | 0 | 2 |
| F4 | 972 | 1886 | 10 | 5 | 0 | 0 |
| F5 | 3890 | 3006 | 40 | 17 | 0 | 4 |
| F6 | 1124 | 2813 | 5 | 9 | 0 | 2 |
| F7 | 4634 | 83512 | 266 | 859 | 32 | 22 |
| F8 | 3761 | 3992 | 15 | 12 | 0 | 0 |

Figure 6:
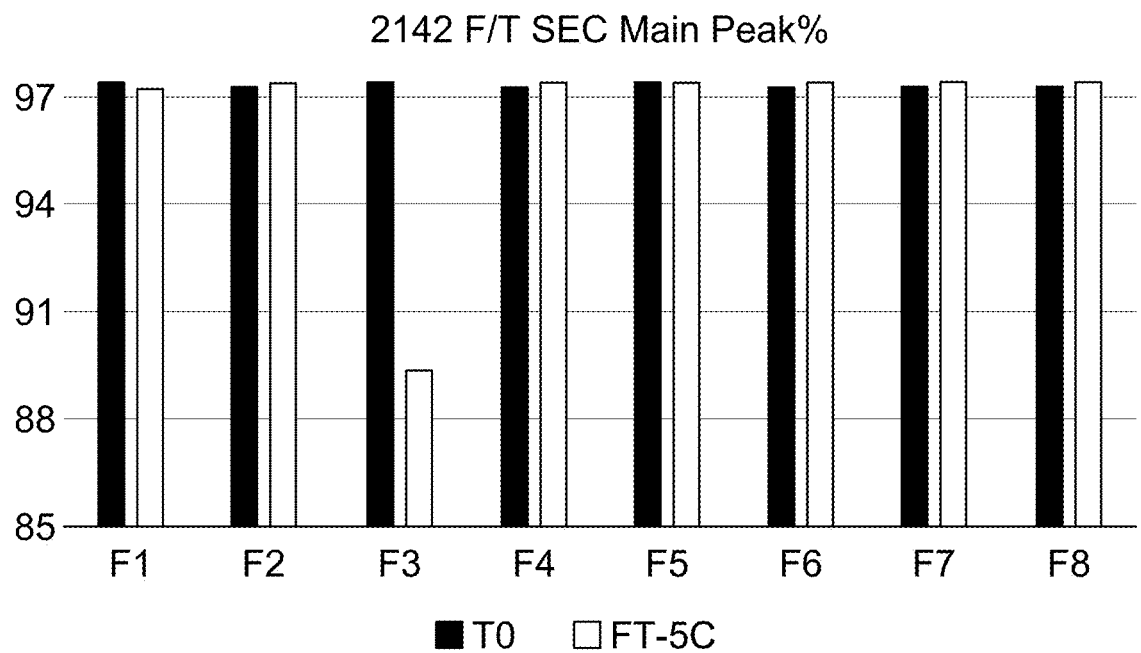
FIG. 6: SEC-HPLC main peak % comparison from the freeze/thaw study.

The SEC-HPLC results for all formulations are listed in Table 12 and FIG. 6.

At T0, all formulations had similar SEC purity with the main peak around 97.5%. After 5 freeze/thaw cycles (−40±5° C./RT), all formulations had comparable SEC main peak purity around 97.5% except the F3 sample. The main peak purity decline in the F3 sample showed a marginally higher decrease at 8.1%.

TABLE 12

SEC-HPLC results from the freeze/thaw study

| Formulation No. | SEC-HPLC results | | | | | |
|---|---|---|---|---|---|---|
| | Main peak % | | HMW % | | LMW % | |
| | T0 | FT-5 C | T0 | FT-5 C | T0 | FT-5 C |
| F1 | 97.5 | 97.3 | 2.6 | 2.7 | ND | ND |
| F2 | 97.4 | 97.5 | 2.6 | 2.5 | ND | ND |
| F3 | 97.5 | 89.4 | 2.5 | 10.6 | ND | ND |
| F4 | 97.4 | 97.5 | 2.6 | 2.5 | ND | ND |
| F5 | 97.5 | 97.5 | 2.6 | 2.6 | ND | ND |
| F6 | 97.4 | 97.5 | 2.6 | 2.5 | ND | ND |
| F7 | 97.4 | 97.5 | 2.6 | 2.5 | ND | ND |
| F8 | 97.4 | 97.5 | 2.6 | 2.5 | ND | ND |

Figure 7:
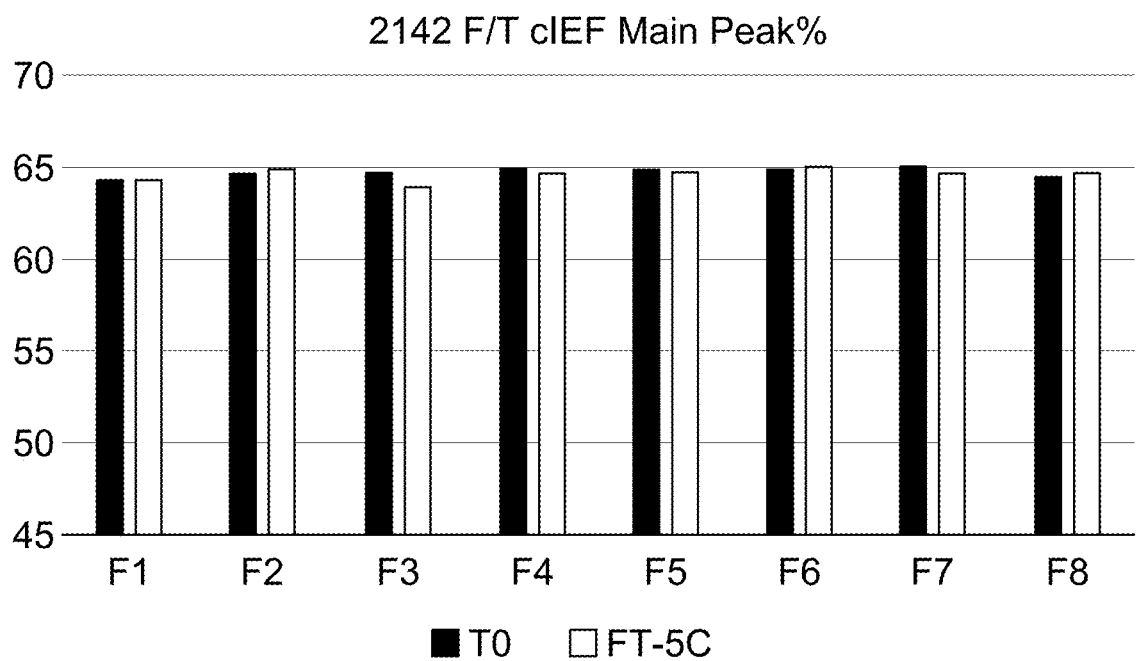
FIG. 7: Comparison of cIEF main peak % from the freeze/thaw study.

The cIEF results for all formulations are listed in Table 13 and FIG. 7.

The pI value of all samples was about 8.1 with insignificant changes after 5 freeze/thaw cycles (−40±5° C./RT).

Compared to T0, the proportion of main peak, acidic peak and basic peak also had no significant changes for all samples through 5 freeze/thaw cycles (−40±5° C./RT).

TABLE 13 cIEF results from the freeze/thaw study

| Formulation No. | cIEF results | | | | | |
|---|---|---|---|---|---|---|
| | Main peak % | | Acidic peak % | | Basic peak % | |
| | T0 | FT-5 C | T0 | FT-5 C | T0 | FT-5 C |
| F1 | 64.3 | 64.3 | 22.1 | 22.3 | 13.5 | 13.4 |
| F2 | 64.6 | 64.8 | 22.0 | 22.5 | 13.4 | 12.7 |
| F3 | 64.7 | 64.0 | 22.0 | 21.3 | 13.3 | 14.7 |
| F4 | 64.9 | 64.7 | 22.3 | 22.2 | 12.8 | 13.1 |
| F5 | 64.9 | 64.6 | 21.8 | 21.9 | 13.3 | 13.5 |
| F6 | 64.9 | 65.0 | 21.8 | 22.1 | 13.3 | 13.0 |
| F7 | 65.1 | 64.7 | 21.9 | 22.0 | 12.9 | 13.2 |
| F8 | 64.5 | 64.7 | 21.6 | 21.9 | 14.0 | 13.4 |

Figure 8A:
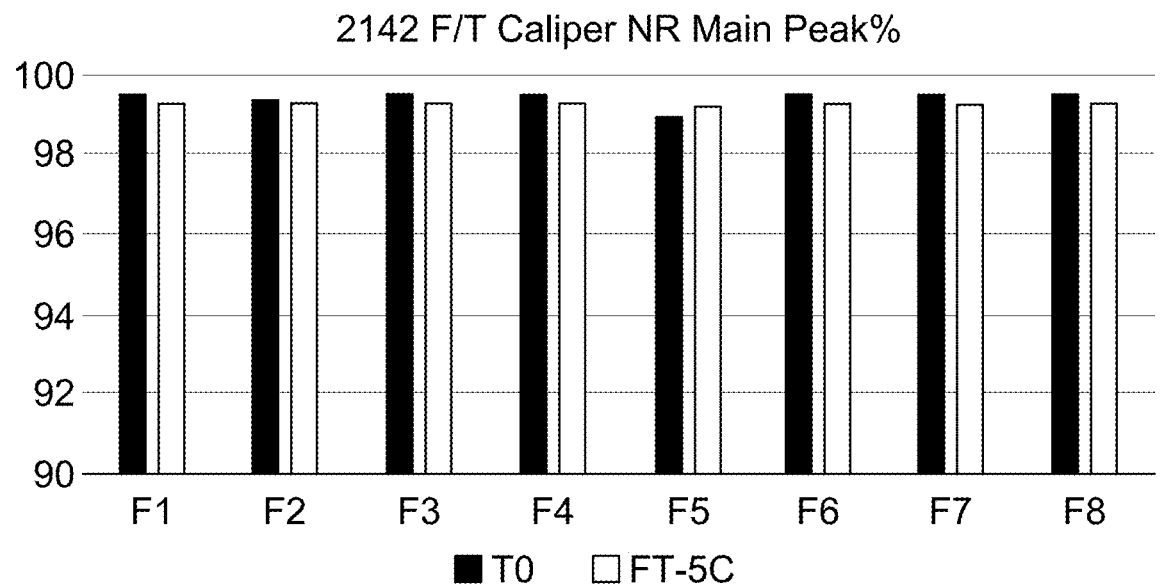
FIGS. 8A-8B: Purity % comparison from the freeze/thaw study in non-reduced SDS-Caliper (FIG. 8A) and reduced SDS-Caliper (FIG. 8B).
Figure 8B:
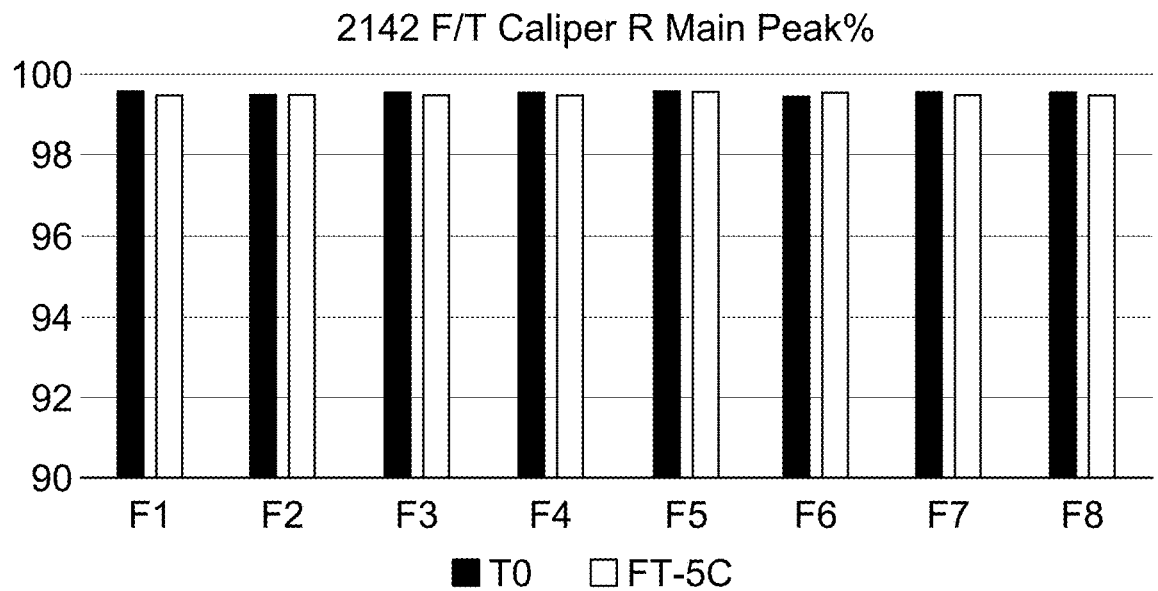

The SDS-Caliper data for all formulations are summarized in Table 14 and FIG. 8.

All formulations showed comparable purity in either non-reduced SDS-Caliper or reduced SDS-Caliper after 5 freeze/thaw cycles (−40±5° C./RT).

TABLE 14

SDS-Caliper results from the freeze/thaw study

| Formulation No. | SDS-Caliper Purity | | | |
|---|---|---|---|---|
| | Non-reduced SDS-Caliper Purity % | | Reduced SDS-Caliper Purity % | |
| | T0 | FT-5 C | T0 | FT-5 C |
| F1 | 99.5 | 99.3 | 99.6 | 99.5 |
| F2 | 99.4 | 99.3 | 99.5 | 99.5 |
| F3 | 99.5 | 99.3 | 99.6 | 99.5 |
| F4 | 99.5 | 99.3 | 99.6 | 99.5 |
| F5 | 99.0 | 99.2 | 99.6 | 99.6 |
| F6 | 99.5 | 99.3 | 99.5 | 99.6 |
| F7 | 99.5 | 99.3 | 99.6 | 99.5 |
| F8 | 99.5 | 99.3 | 99.6 | 99.5 |

The appearance, protein concentration, osmolality and pH value results of the agitation study are summarized in Table 15.

The protein concentration and osmolality were all around the target value at T0.

Except for F7, all formulations remained stable in pH value and appearance after agitation at 300 rpm at 25° C. for 7 days. A large number of visible particles were found in the F7 sample after agitation at 300 rpm at 25° C. for 7 days. The opalescent level of the F1 samples got deeper after agitation at 300 rpm at 25° C. for 7 days.

TABLE 15

Protein concentration, pH value, osmolality and appearance results from the agitation study

| No. | Protein concentration mg/mL | Osmolality mOsm/kg | pH | | Appearance | |
|---|---|---|---|---|---|---|
| | T0 | T0 | T0 | A-7 D | T0 | A-7 D |
| F1 | 25.7 | 323 | 5.7 | 5.5 | A* | A |
| F2 | 25.5 | 301 | 5.7 | 5.5 | A | A |
| F3 | 25.6 | 298 | 5.7 | 5.5 | A | A |
| F4 | 25.8 | 327 | 5.6 | 5.4 | A | A |
| F5 | 25.7 | 320 | 5.6 | 5.4 | A | A |
| F6 | 25.7 | 316 | 5.6 | 5.4 | A | A |
| F7 | 25.7 | 324 | 5.6 | 5.4 | A | C |
| F8 | 24.1 | 302 | 5.6 | 5.5 | A | A |

Notes:
A = Colorless, slightly opalescent and free of visible particle;
C = Colorless, slightly opalescent and a large number of visible particles.

The MFI data for all samples is listed in Table 16.

The particle counts of F7 were slightly higher than others at T0. After 7-day agitation at 300 rpm at 25° C., particle counts in F7 increased significantly due to the absence of PS80. Except for F7, all other samples had similar particulate count and no growth trend was found.

TABLE 16

MFI results from the agitation study

| Formulation No. | MFI (Counts/mL) | | | | | |
|---|---|---|---|---|---|---|
| | ECD ≥ 2 μm | | ECD ≥ 10 μm | | ECD ≥ 25 μm | |
| | T0 | A-7 D | T0 | A-7 D | T0 | A-7 D |
| F1 | 635 | 871 | 7 | 4 | 0 | 0 |
| F2 | 2040 | 3028 | 10 | 10 | 0 | 2 |
| F3 | 3266 | 2242 | 5 | 17 | 0 | 0 |
| F4 | 972 | 579 | 10 | 7 | 0 | 0 |
| F5 | 3890 | 1105 | 40 | 7 | 0 | 0 |
| F6 | 1124 | 697 | 5 | 7 | 0 | 0 |
| F7 | 4634 | 44532 | 266 | 9624 | 32 | 2349 |
| F8 | 3761 | 1033 | 15 | 10 | 0 | 0 |

Figure 9:
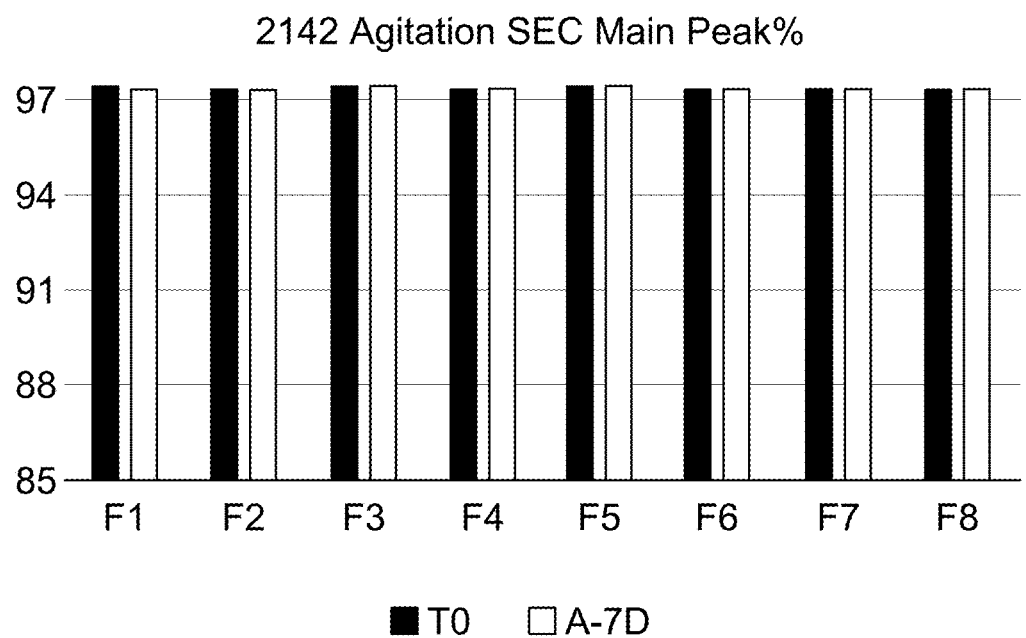
FIG. 9: SEC-HPLC main peak % comparison from the agitation study.

The SEC-HPLC results for all formulations are listed in Table 17 and FIG. 9.

After 7-day agitation at 300 rpm at 25° C., all formulations had similar SEC main peak purity of more than 97%.

TABLE 17

SEC-HPLC results from the agitation study

| Formulation No. | SEC-HPLC results | | | | | |
|---|---|---|---|---|---|---|
| | Main peak % | | HMW % | | LMW % | |
| | T0 | A-7 D | T0 | A-7 D | T0 | A-7 D |
| F1 | 97.5 | 97.4 | 2.6 | 2.6 | ND | ND |
| F2 | 97.4 | 97.4 | 2.6 | 2.6 | ND | ND |
| F3 | 97.5 | 97.5 | 2.5 | 2.5 | ND | ND |
| F4 | 97.4 | 97.4 | 2.6 | 2.6 | ND | ND |
| F5 | 97.5 | 97.5 | 2.6 | 2.6 | ND | ND |
| F6 | 97.4 | 97.4 | 2.6 | 2.6 | ND | ND |
| F7 | 97.4 | 97.4 | 2.6 | 2.6 | ND | ND |
| F8 | 97.4 | 97.4 | 2.6 | 2.6 | ND | ND |

Figure 10:
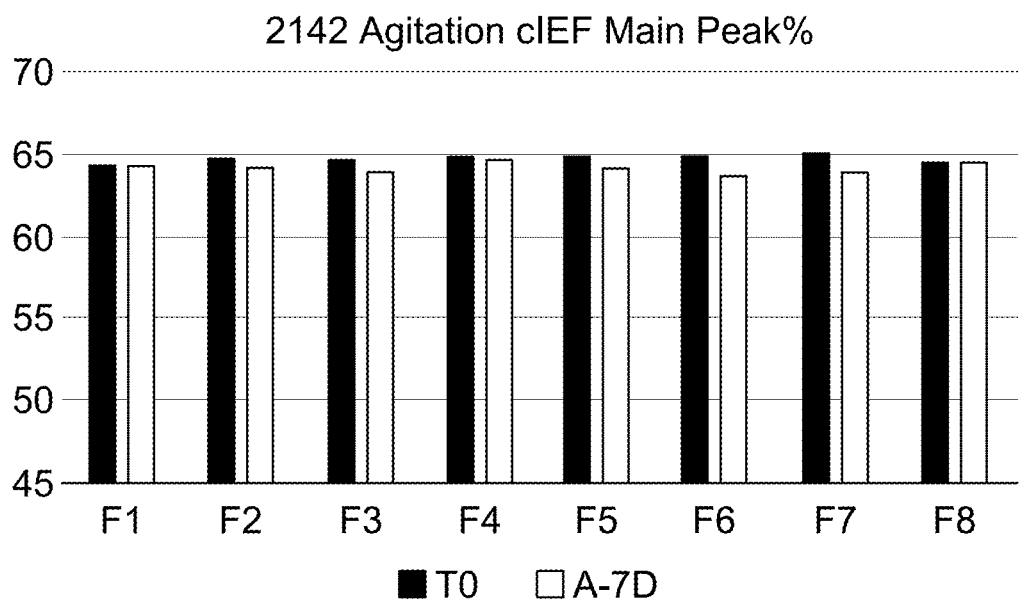
FIG. 10: Comparison of cIEF main peak % from the agitation study.

The cIEF results for all formulations are listed in Table 18 and FIG. 10.

The pI value of all samples was about 8.1 with insignificant changes after agitation at 300 rpm at 25° C. for 7 days.

After 7-day agitation at 300 rpm at 25° C., the main peak purity of all formulations remained stable.

TABLE 18 cIEF results from the agitation study

| Formulation No. | cIEF results | | | | | |
|---|---|---|---|---|---|---|
| | Main peak % | | Acidic peak % | | Basic peak % | |
| | T0 | A-7 D | T0 | A-7 D | T0 | A-7 D |
| F1 | 64.3 | 64.3 | 22.1 | 22.0 | 13.5 | 13.7 |
| F2 | 64.6 | 64.2 | 22.0 | 22.4 | 13.4 | 13.4 |
| F3 | 64.7 | 64.0 | 22.0 | 22.1 | 13.3 | 13.9 |
| F4 | 64.9 | 64.6 | 22.3 | 21.9 | 12.8 | 13.5 |
| F5 | 64.9 | 64.1 | 21.8 | 21.9 | 13.3 | 14.0 |
| F6 | 64.9 | 63.8 | 21.8 | 22.4 | 13.3 | 13.8 |
| F7 | 65.1 | 64.0 | 21.9 | 21.9 | 12.9 | 14.1 |
| F8 | 64.5 | 64.5 | 21.6 | 21.9 | 14.0 | 13.6 |

Figure 11A:
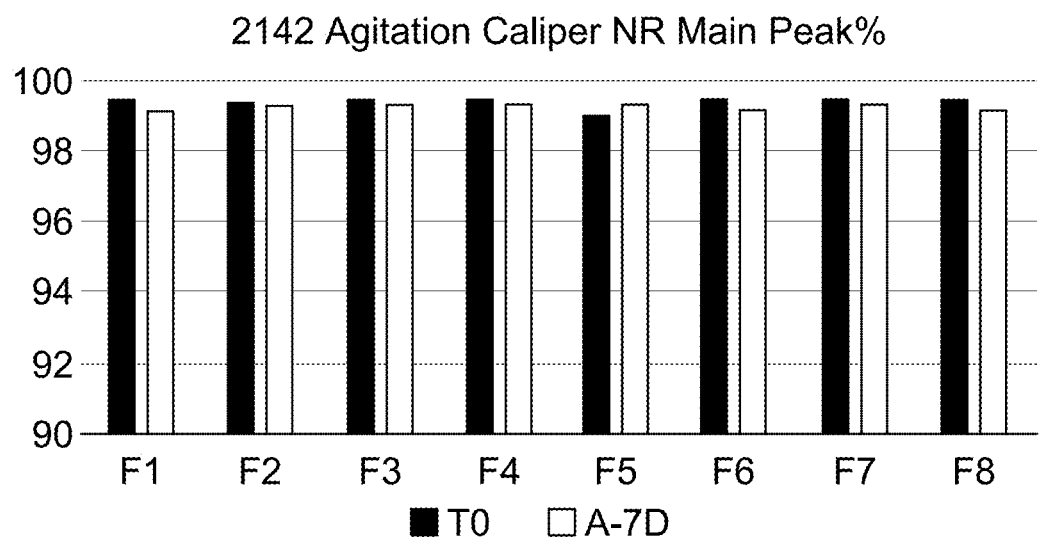
FIGS. 11A-11B: Purity % comparison from the agitation study in non-reduced SDS-Caliper (FIG. 11A) and reduced SDS-Caliper (FIG. 11B).
Figure 11B:
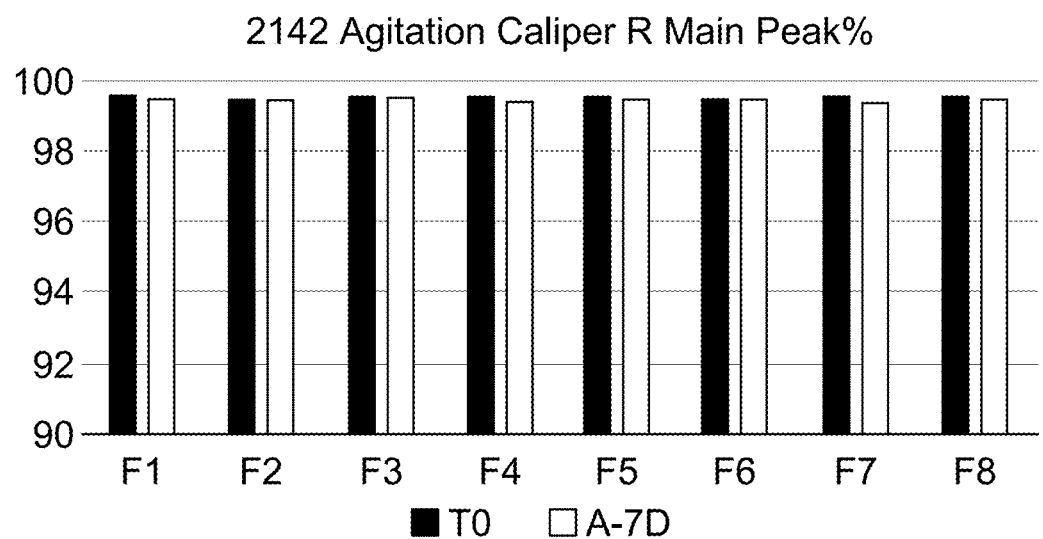

The SDS-Caliper results for all formulations are listed in Table 19 and FIG. 11.

All formulations showed comparable purity in either non-reduced SDS-Caliper or reduced SDS Caliper after 7-day agitation at 300 rpm at 25° C.

TABLE 19

SDS-Caliper results from the agitation study

| Formulation No. | SDS-Caliper Purity | | | |
|---|---|---|---|---|
| | Non-reduced SDS-Caliper Purity % | | Reduced SDS-Caliper Purity % | |
| | T0 | A-7 D | T0 | A-7 D |
| F1 | 99.5 | 99.2 | 99.6 | 99.5 |
| F2 | 99.4 | 99.3 | 99.5 | 99.5 |
| F3 | 99.5 | 99.3 | 99.6 | 99.6 |
| F4 | 99.5 | 99.3 | 99.6 | 99.4 |
| F5 | 99.0 | 99.3 | 99.6 | 99.5 |
| F6 | 99.5 | 99.2 | 99.5 | 99.5 |
| F7 | 99.5 | 99.3 | 99.6 | 99.4 |
| F8 | 99.5 | 99.2 | 99.6 | 99.5 |

The appearance, protein concentration, osmolality and pH value results for the accelerated stability study are summarized in Table 20 and Table 21.

The protein concentration and osmolality were all around the target value at T0.

After storage at 2~8° C., 25±2° C. or 40±2° C. for 4 weeks, the pH values remained unchanged for all the formulations while slightly visible particles were found in F7 due to the absence of PS80.

TABLE 20

Appearance results from the accelerated stability study

| Formulation No. | Appearance | | | | | |
|---|---|---|---|---|---|---|
| | T0 | 05-4 W | 25-2 W | 25-4 W | 40-2 W | 40-4 W |
| F1 | A* | A | A | A | A | A |
| F2 | A | A | A | A | A | A |
| F3 | A | A | A | A | A | A |
| F4 | A | A | A | A | A | A |
| F5 | A | A | A | A | A | A |
| F6 | A | A | A | A | A | A |
| F7 | A | B | B | B | B | B |
| F8 | A | A | A | A | A | A |

Notes:

A = Colorless, slightly opalescent and free of visible particle;

B = Colorless, slightly opalescent and slightly visible particles.

TABLE 21

Protein concentration, osmolality and pH results from the accelerated stability study

| No. | Conc. (mg/ml) T0 | Osmolality (mOsm/kg) T0 | pH T0 | 05-4 W | 25-2 W | 25-4 W | 40-2 W | 40-4 W |
|---|---|---|---|---|---|---|---|---|
| F1 | 25.7 | 323 | 5.7 | 5.6 | 5.6 | 5.6 | 5.5 | 5.6 |
| F2 | 25.5 | 301 | 5.7 | 5.5 | 5.5 | 5.5 | 5.5 | 5.5 |
| F3 | 25.6 | 298 | 5.7 | 5.6 | 5.6 | 5.6 | 5.6 | 5.6 |
| F4 | 25.8 | 327 | 5.6 | 5.5 | 5.5 | 5.4 | 5.5 | 5.5 |
| F5 | 25.7 | 320 | 5.6 | 5.5 | 5.5 | 5.5 | 5.5 | 5.5 |
| F6 | 25.7 | 316 | 5.6 | 5.5 | 5.5 | 5.5 | 5.5 | 5.5 |
| F7 | 25.7 | 324 | 5.6 | 5.5 | 5.5 | 5.5 | 5.5 | 5.5 |
| F8 | 24.1 | 302 | 5.6 | 5.6 | 5.5 | 5.6 | 5.4 | 5.6 |

The MFI data for all the samples are listed in Table 22.

After storage at 2~8° C. and 25±2° C. for 4 weeks, there was no obvious changes for sub-visible particle counts in all formulations.

After storage at 40±2° C. for 4 weeks, the increase of sub-visible particle counts (ECD≥10 μm and ECD≥25 μm) in F7 was much higher than that in other formulations and there was a slight growth trend of particle counts for F7.

TABLE 22

MFI results from the accelerated stability study

| Size distribution | No. | T0 | 05-4 W | 25-2 W | 25-4 W | 40-2 W | 40-4 W |
|---|---|---|---|---|---|---|---|
| ECD ≥ 2 μm | F1 | 635 | 1433 | 949 | 1448 | 1874 | 8868 |
| | F2 | 2040 | 1417 | 9376 | 1930 | 1248 | 1369 |
| | F3 | 3266 | 2541 | 1079 | 841 | 3733 | 1073 |
| | F4 | 972 | 689 | 1660 | 2003 | 902 | 687 |
| | F5 | 3890 | 1122 | 688 | 2525 | 931 | 626 |
| | F6 | 1124 | 1169 | 307 | 1479 | 989 | 563 |
| | F7 | 4634 | 4742 | 2191 | 4021 | 3104 | 3872 |
| | F8 | 3761 | 881 | 73 | 1825 | 1199 | 1104 |
| ECD ≥ 10 μm | F1 | 7 | 15 | 5 | 14 | 7 | 86 |
| | F2 | 10 | 12 | 17 | 15 | 4 | 12 |
| | F3 | 5 | 30 | 5 | 4 | 19 | 12 |
| | F4 | 10 | 9 | 5 | 5 | 2 | 0 |
| | F5 | 40 | 4 | 0 | 7 | 4 | 2 |
| | F6 | 5 | 14 | 9 | 7 | 14 | 6 |
| | F7 | 266 | 181 | 48 | 243 | 368 | 626 |
| | F8 | 15 | 5 | 5 | 9 | 27 | 5 |
| ECD ≥ 25 μm | F1 | 0 | 0 | 0 | 0 | 0 | 4 |
| | F2 | 0 | 0 | 2 | 2 | 0 | 5 |
| | F3 | 0 | 0 | 0 | 0 | 0 | 0 |
| | F4 | 0 | 0 | 0 | 0 | 0 | 0 |
| | F5 | 0 | 2 | 0 | 0 | 0 | 0 |
| | F6 | 0 | 5 | 0 | 2 | 7 | 0 |
| | F7 | 32 | 10 | 2 | 20 | 53 | 189 |
| | F8 | 0 | 0 | 2 | 0 | 4 | 0 |

Figure 12A:
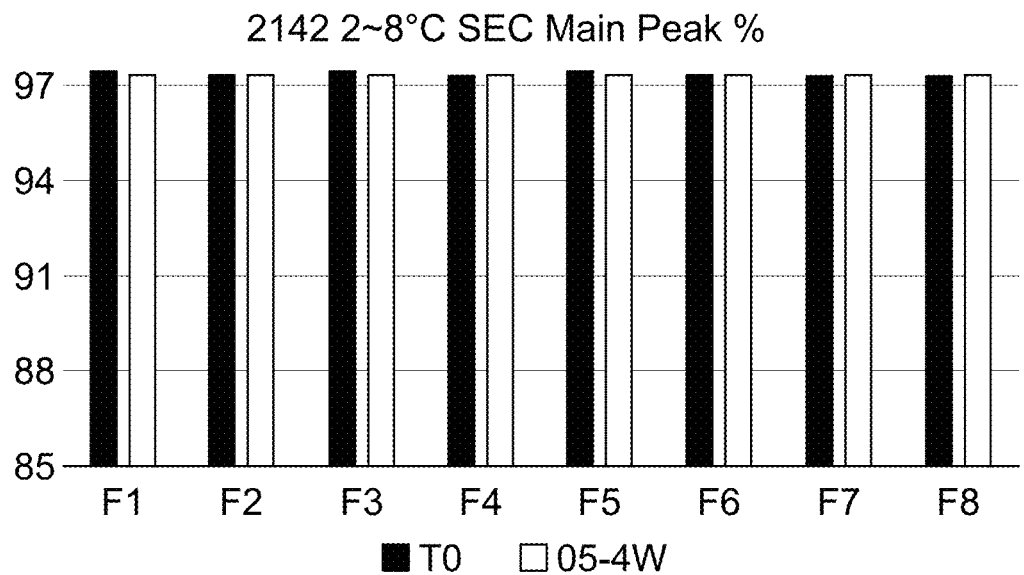
FIGS. 12A-12C: SEC-Main peak % comparison at 2-8° C.
Figure 12B:
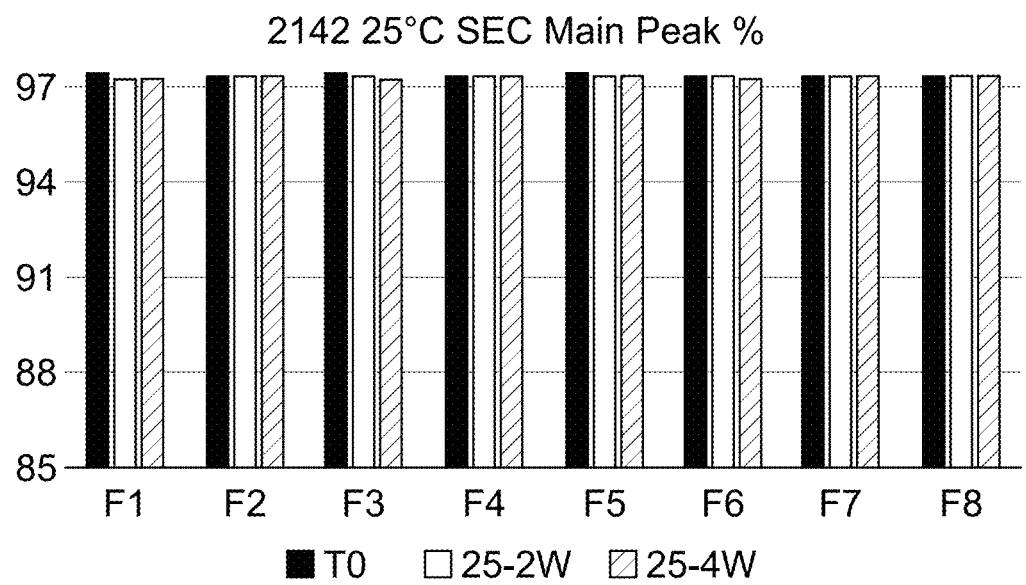
Figure 12C:
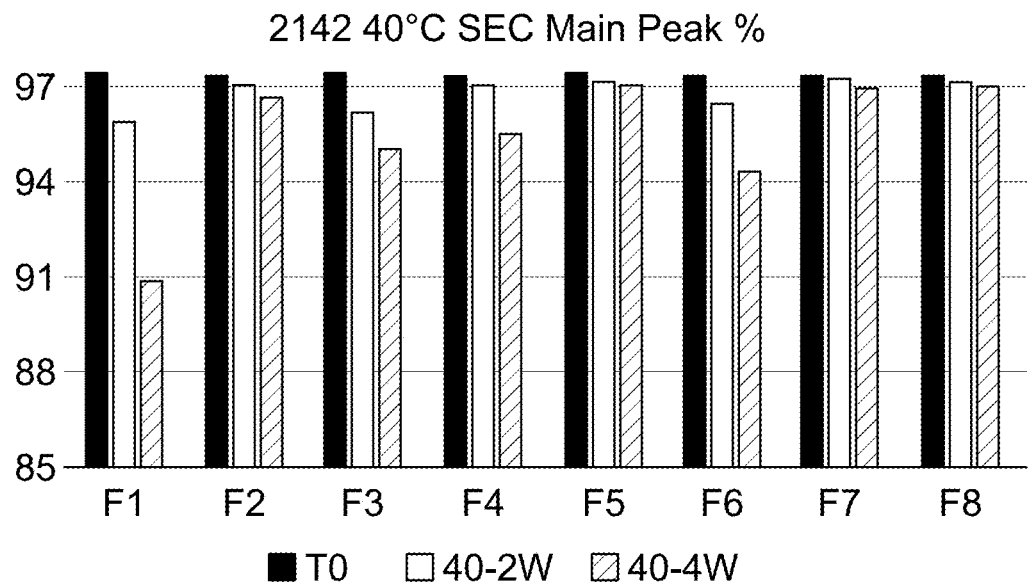

The SEC-HPLC data for all the samples are listed in Table 23 and FIG. 12.

After storage at 2~8° C. or 25±2° C. for 4 weeks, there was no obvious changes in main peak purity in all formulations.

Significant decrease of the main peak was observed after 2 weeks at 40±2° C. After storage at 40±2° C. for 4 weeks, decline of the main peak was in the range of 0.30%~6.6%. The decline of main peak purity in F1, F6 was 6.6 and 3.0%, respectively. In contrast, the main peak declines in F5 and F8 were relatively milder than for the other formulations.

TABLE 23

SEC-HPLC results from the accelerated stability study

| | Formulation No. | T0 | 05-4 W | 25-2 W | 25-4 W | 40-2 W | 40-4 W |
|---|---|---|---|---|---|---|---|
| Main peak % | F1 | 97.5 | 97.4 | 97.3 | 97.3 | 95.9 | 90.9 |
| | F2 | 97.4 | 97.4 | 97.4 | 97.4 | 97.1 | 96.7 |
| | F3 | 97.5 | 97.4 | 97.4 | 97.3 | 96.2 | 95.0 |
| | F4 | 97.4 | 97.4 | 97.4 | 97.4 | 97.1 | 95.5 |
| | F5 | 97.5 | 97.4 | 97.4 | 97.4 | 97.2 | 97.1 |
| | F6 | 97.4 | 97.4 | 97.4 | 97.3 | 96.5 | 94.4 |
| | F7 | 97.4 | 97.4 | 97.4 | 97.4 | 97.3 | 97.0 |
| | F8 | 97.4 | 97.4 | 97.4 | 97.4 | 97.2 | 97.1 |
| HMW % | F1 | 2.6 | 2.6 | 2.7 | 2.7 | 4.1 | 9.1 |
| | F2 | 2.6 | 2.6 | 2.6 | 2.6 | 2.9 | 3.3 |
| | F3 | 2.5 | 2.6 | 2.6 | 2.7 | 3.8 | 5.0 |
| | F4 | 2.6 | 2.6 | 2.6 | 2.7 | 2.9 | 4.5 |
| | F5 | 2.6 | 2.6 | 2.6 | 2.6 | 2.8 | 3.0 |
| | F6 | 2.6 | 2.6 | 2.6 | 2.7 | 3.5 | 5.7 |
| | F7 | 2.6 | 2.6 | 2.6 | 2.6 | 2.7 | 3.0 |
| | F8 | 2.6 | 2.6 | 2.6 | 2.6 | 2.8 | 2.9 |
| LMW % | F1 | ND | ND | ND | ND | ND | ND |
| | F2 | ND | ND | ND | ND | ND | ND |
| | F3 | ND | ND | ND | ND | ND | ND |
| | F4 | ND | ND | ND | ND | ND | ND |
| | F5 | ND | ND | ND | ND | ND | ND |
| | F6 | ND | ND | ND | ND | ND | ND |
| | F7 | ND | ND | ND | ND | ND | ND |
| | F8 | ND | ND | ND | ND | ND | ND |

Figure 13A:
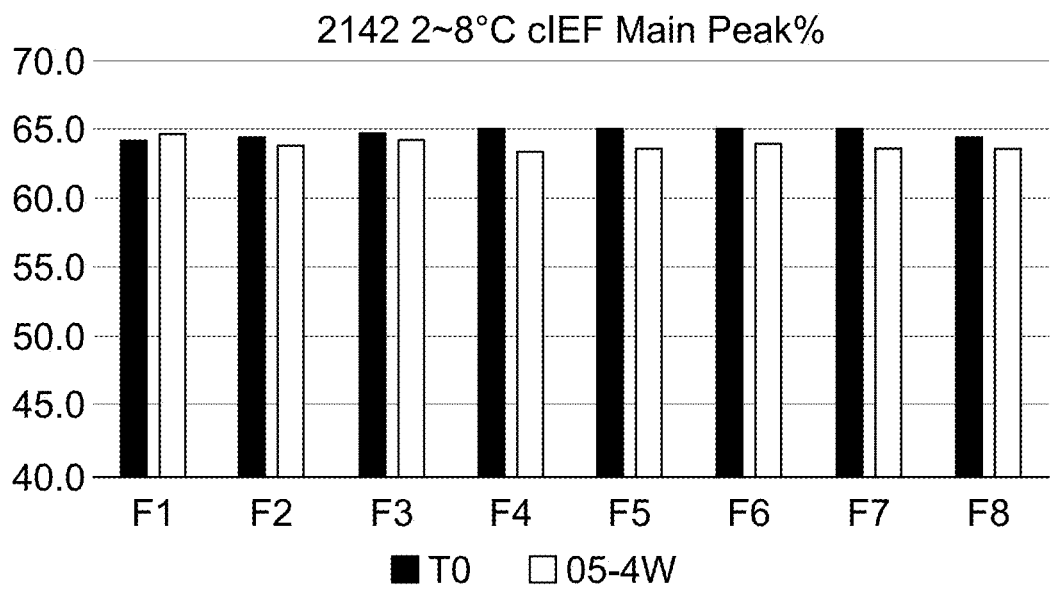
FIGS. 13A-13C: cIEF main peak % comparison at 2-8° C.
Figure 13B:
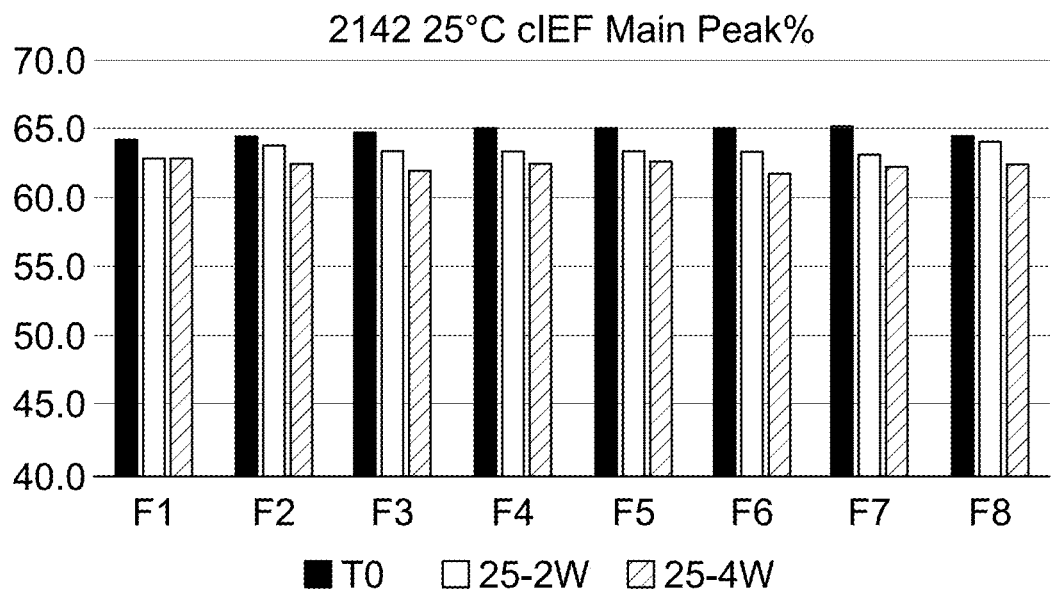
Figure 13C:
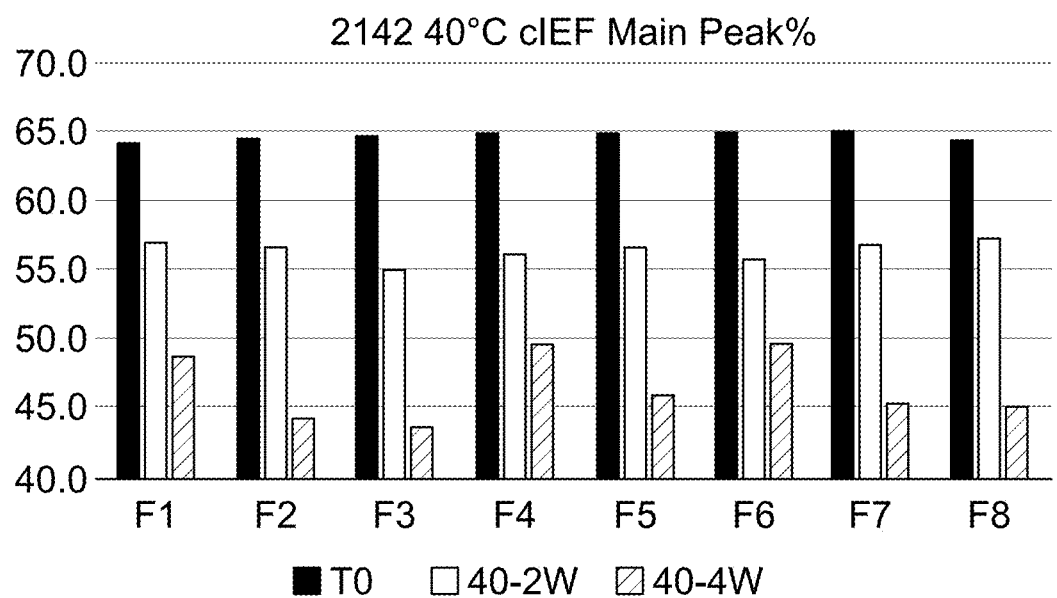

The cIEF data for all samples is listed in Table 24 and FIG. 13.

The pI value of all samples was about 8.1 with insignificant changes after storage at 2~8° C., 25±2° C. or 40±2° C.

After storage at 2~8° C. or 25±2° C. for 4 weeks, there was no significant changes in the main peak purity of all formulations.

After storage at 40±2° C. for 4 weeks, the main peak purity of all samples declined significantly, together with significantly increased acidic peak. There was no significant difference in main peak percentage of all samples and the decline of main peaks was in the range of 15.1%-21.1%.

TABLE 24 cIEF results from the accelerated stability study

| | Formulation No. | T0 | 05-4 W | 25-2 W | 25-4 W | 40-2 W | 40-4 W |
|---|---|---|---|---|---|---|---|
| Main peak % | F1 | 64.3 | 64.7 | 62.9 | 63.0 | 57.2 | 48.8 |
| | F2 | 64.6 | 63.8 | 63.9 | 62.6 | 56.6 | 44.3 |

TABLE 24-continued cIEF results from the accelerated stability study

| Formulation No. | | T0 | 05-4 W | 25-2 W | 25-4 W | 40-2 W | 40-4 W |
|---|---|---|---|---|---|---|---|
| | F3 | 64.7 | 64.3 | 63.4 | 62.0 | 55.2 | 43.6 |
| | F4 | 64.9 | 63.5 | 63.4 | 62.4 | 56.2 | 49.8 |
| | F5 | 64.9 | 63.7 | 63.3 | 62.8 | 56.6 | 45.9 |
| | F6 | 64.9 | 64.1 | 63.4 | 61.9 | 55.7 | 49.8 |
| | F7 | 65.1 | 63.7 | 63.2 | 62.2 | 56.8 | 45.5 |
| | F8 | 64.5 | 63.7 | 64.0 | 62.6 | 57.4 | 45.2 |
| Acidic peak % | F1 | 22.1 | 22.4 | 22.4 | 22.9 | 26.6 | 36.0 |
| | F2 | 22.0 | 23.1 | 22.2 | 23.3 | 27.3 | 40.0 |
| | F3 | 22.0 | 22.6 | 22.6 | 23.5 | 28.9 | 41.8 |
| | F4 | 22.3 | 23.3 | 22.4 | 23.1 | 26.6 | 34.9 |
| | F5 | 21.8 | 22.8 | 22.6 | 22.7 | 26.2 | 37.3 |
| | F6 | 21.8 | 22.8 | 22.7 | 23.6 | 28.1 | 35.3 |
| | F7 | 21.9 | 23.0 | 22.7 | 23.3 | 26.4 | 38.3 |
| | F8 | 21.6 | 23.2 | 21.4 | 23.2 | 26.2 | 39.0 |
| Basic peak % | F1 | 13.5 | 13.0 | 14.7 | 14.0 | 16.2 | 15.2 |
| | F2 | 13.4 | 13.1 | 14.0 | 14.1 | 16.1 | 15.8 |
| | F3 | 13.3 | 13.2 | 14.0 | 14.5 | 15.9 | 14.6 |
| | F4 | 12.8 | 13.2 | 14.2 | 14.4 | 17.2 | 15.4 |
| | F5 | 13.3 | 13.5 | 14.1 | 14.5 | 17.2 | 16.8 |
| | F6 | 13.3 | 13.1 | 14.0 | 14.5 | 16.2 | 14.9 |
| | F7 | 12.9 | 13.3 | 14.1 | 14.5 | 16.8 | 16.2 |
| | F8 | 14.0 | 13.1 | 14.6 | 14.2 | 16.4 | 15.8 |

Figure 14A:
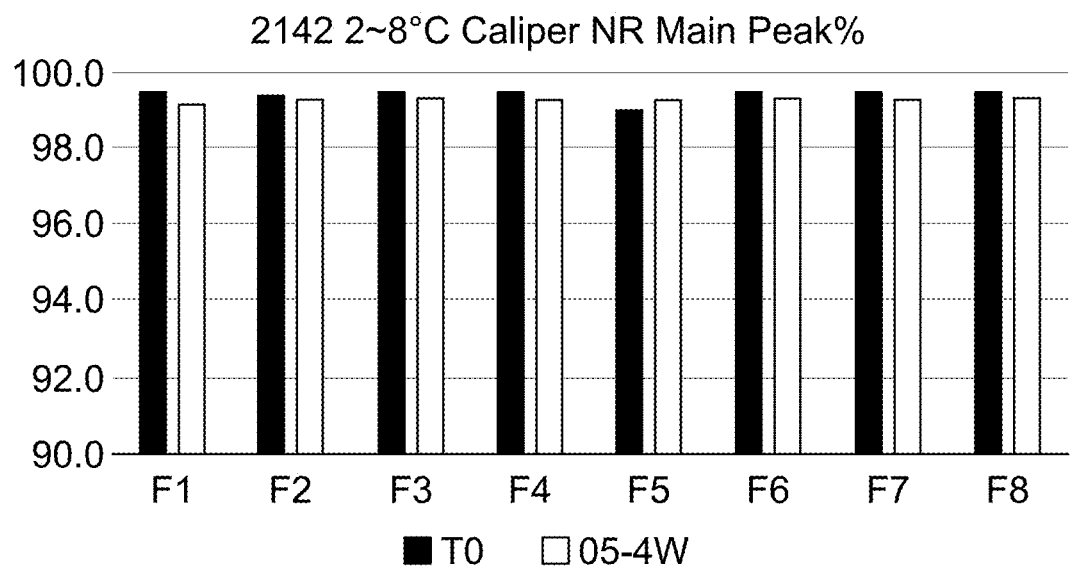
FIGS. 14A-14C: Non-reduced SDS-Caliper purity % comparison at 2-8° C.
Figure 14B:
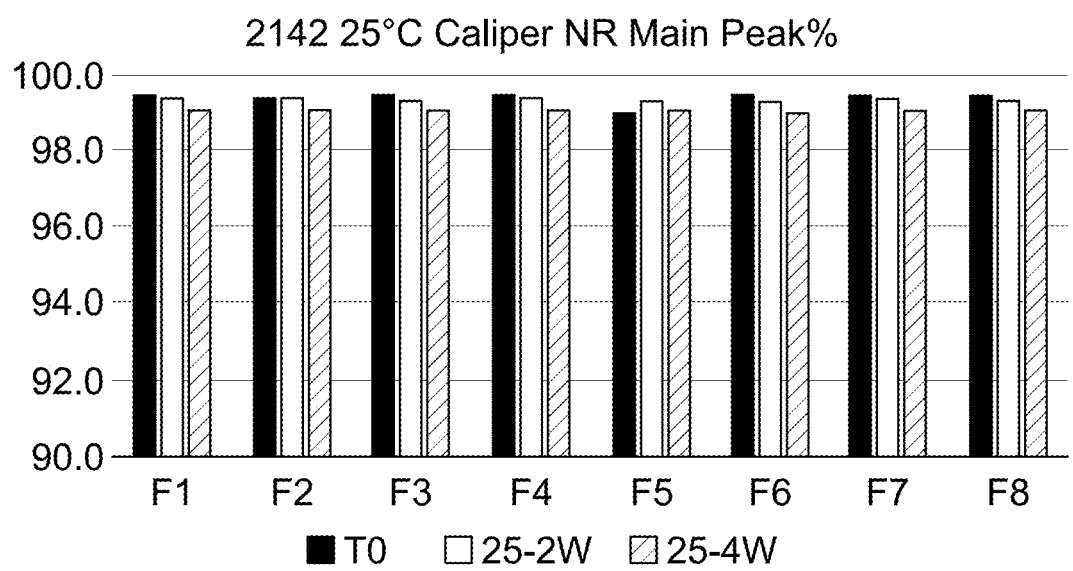
Figure 14C:
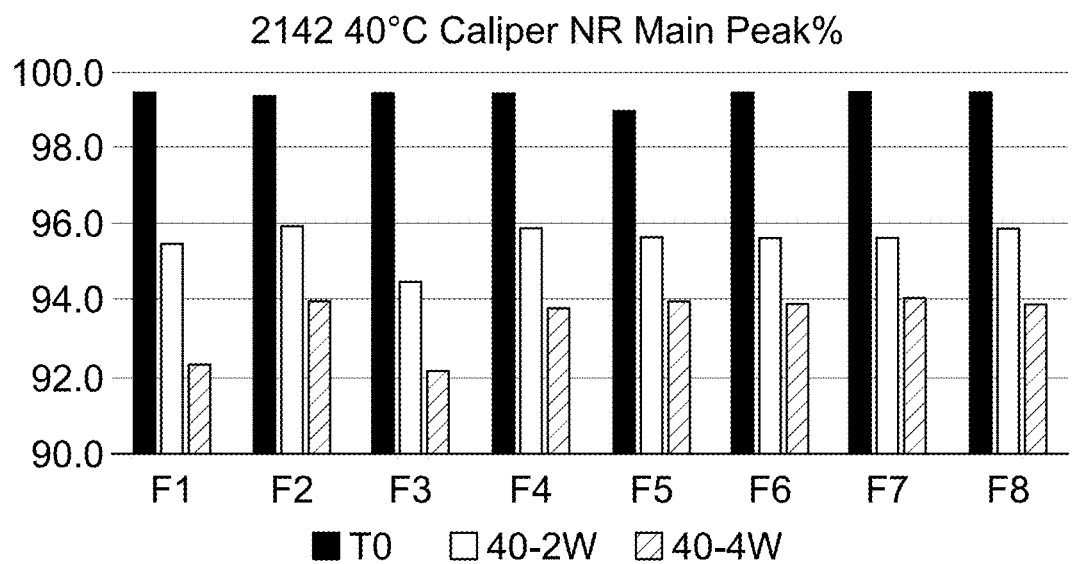
Figure 15A:
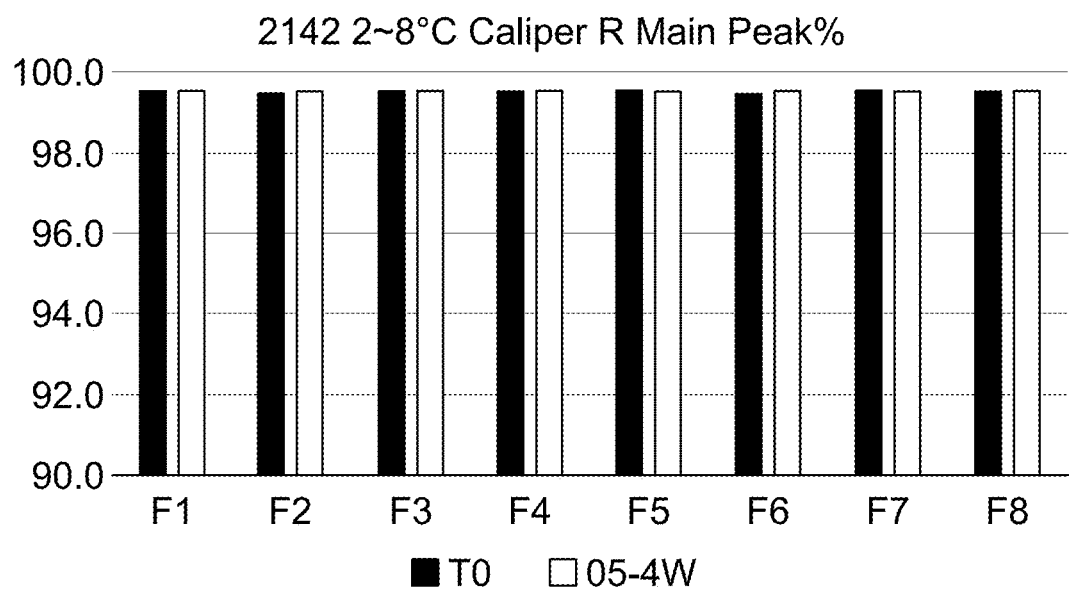
(FIG. 15A), 25±2° C.
Figure 15B:
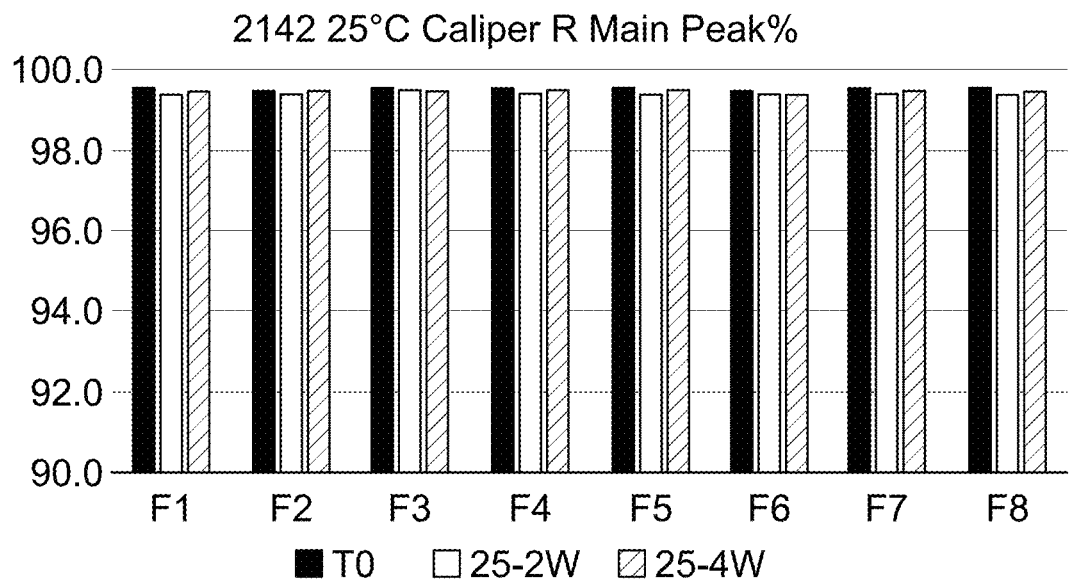
(FIG. 15B) and 10 40±2° C.
Figure 15C:
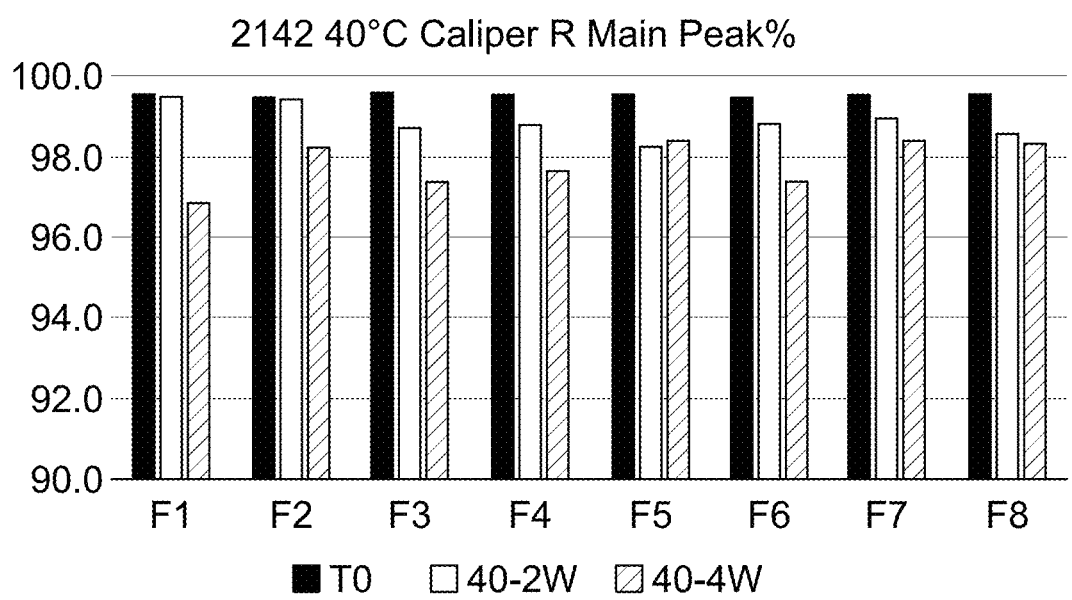
(FIG. 15C).

The SDS-Caliper data for all samples is listed in Table 25, FIG. 14 and FIG. 15.

After storage at 2~8° C. or 25±2° C. for 4 weeks, all formulations showed comparable purity in non-reduced SDS-Caliper and reduced SDS-Caliper.

After storage at 40±2° C. for 4 weeks, the purity of all formulations significantly declined in non-reduced SDS-Caliper and reduced SDS-Caliper. The decline of non-reduced purity in F1 and F3 was 7.2% and 7.3%, which were the greatest declines in all formulations. The decline of reduced purity in F1, F3 and F6 were 2.7%, 2.3% and 2.2%, respectively. The decline of non-reduced SDS-Caliper purity or reduced SDS-Caliper purity in F2, F5 and F7 were relatively lower than other formulations.

After 5 freeze/thaw cycles (−40±5° C./RT), anti-Cx43 Ab in all formulations had no significant difference in protein concentration, pH value, osmolality and purity (SDS-Caliper Reduced & Non-Reduced). Visible particles and sub-visible particle counts (MFI) in F7 (without PS80) were much higher than in other formulations. The SEC main peak of the F3 sample showed marginally higher decrease at 8.1%. The opalescent level of F1 samples got deeper after 5 freeze/thaw cycles (−40±5° C./RT).

After 7-day agitation at 300 rpm at 25° C., anti-Cx43 Ab in all formulations had no significant difference in protein concentration, pH value, osmolality and purity (SEC-HPLC, cIEF, SDS-Caliper Reduced & Non-Reduced). Visible particles and sub-visible particle counts (MFI) in F7 (without PS80) were much higher than other formulations. The opalescent level of F1 samples got deeper after agitation at 300 rpm at 25° C. for 7 days.

After storage at 2~8° C. for 4 weeks, anti-Cx43 Ab in all formulations had no significant difference in protein concentration, pH value, osmolality, sub-visible particles and purity (SEC-HPLC, cIEF, SDS-Caliper Reduced & Non-Reduced). Only slightly visible particles were found in F7 after storage at 2~8° C. for 4 weeks.

After storage at 25±2° C. for 4 weeks, anti-Cx43 Ab in all formulations had no significant difference in protein concentration, pH value, osmolality, sub-visible particles and purity (SEC-HPLC, SDS-Caliper Reduced & Non-Reduced). In addition, slightly visible particles were found in formulation F7 due to absence of PS80. The cIEF main peak of all samples declined slightly, but no significant difference was found in 8 formulations after storage at 25±2° C. for 4 weeks.

After storage at 40±2° C. for 4 weeks, anti-Cx43 Ab in all formulations had no significant difference in protein concentration, pH value and osmolality. Slightly visible particles were found in formulation F7 due to absence of PS80. The increase of sub-visible particle counts (ECD≥10 m and ECD≥25 m) in F7 was much higher than that in other formulations. The purity (SEC-HPLC, cIEF, SDS-Caliper

TABLE 25

SDS-Caliper results from the accelerated stability study

| Formulation | | No. | T0 | 05-4 W | 25-2 W | 25-4 W | 40-2 W | 40-4 W |
|---|---|---|---|---|---|---|---|---|
| Non-reduced SDS- | | F1 | 99.5 | 99.2 | 99.4 | 99.1 | 95.5 | 92.3 |
| Caliper Purity % | | F2 | 99.4 | 99.3 | 99.4 | 99.1 | 96.0 | 94.0 |
| | | F3 | 99.5 | 99.3 | 99.3 | 99.1 | 94.5 | 92.2 |
| | | F4 | 99.5 | 99.3 | 99.4 | 99.1 | 95.9 | 93.8 |
| | | F5 | 99.0 | 99.3 | 99.3 | 99.1 | 95.7 | 94.0 |
| | | F6 | 99.5 | 99.3 | 99.3 | 99.0 | 95.7 | 93.9 |
| | | F7 | 99.5 | 99.3 | 99.4 | 99.1 | 95.7 | 94.1 |
| | | F8 | 99.5 | 99.3 | 99.3 | 99.1 | 95.9 | 93.9 |
| Reduced SDS- | | F1 | 99.6 | 99.6 | 99.4 | 99.5 | 99.5 | 96.9 |
| Caliper Purity % | | F2 | 99.5 | 99.6 | 99.4 | 99.5 | 99.4 | 98.2 |
| | | F3 | 99.6 | 99.6 | 99.5 | 99.5 | 98.7 | 97.3 |
| | | F4 | 99.6 | 99.6 | 99.4 | 99.5 | 98.8 | 97.6 |
| | | F5 | 99.6 | 99.6 | 99.4 | 99.5 | 98.2 | 98.4 |
| | | F6 | 99.5 | 99.6 | 99.4 | 99.4 | 98.8 | 97.3 |
| | | F7 | 99.6 | 99.6 | 99.4 | 99.5 | 98.9 | 98.4 |
| | | F8 | 99.6 | 99.6 | 99.4 | 99.5 | 98.5 | 98.3 |

Reduced & Non-Reduced) of all samples significantly declined. The decline of the SEC main peak in F1 and F6 was much higher than in other formulations. The main peak declines of SEC in F5 and F8 were relatively milder than that in other formulations. There was no significant difference in cIEF main peak percentage of all samples and the decline of main peaks was in the range of 15.1%~21.1%. The decline in SDS-Caliper purity (non-reduced) in F1 and F3 were higher than other formulations. F1 showed higher decrease in SDS-Caliper purity (reduced) than others. The decline of non-reduced SDS-Caliper purity or reduced SDS-Caliper purity in F2, F5 and F7 were relatively lower than other formulations.

In summary, formulation development studies including pH/Buffer screening, excipients and PS80 strength screening were performed to determine the lead formulation.

In pH/buffer screening, histidine/histidine hydrochloride buffer system exhibited optimal capability of protein stabilizing.

In excipients and PS80 strength screening, sodium chloride, sorbitol, glycine and sucrose (F1, F2, F3 and F4) were chosen to investigate their stabilizing capability for anti-Cx43 Ab. The results suggested that the anti-Cx43 Ab was relatively more stable in histidine buffer with sucrose as excipient. The stability data of samples with different concentrations of PS80 (F4, F6 and F7) showed that F4 (with 0.02% PS80) provided better stabilization for the anti-Cx43 Ab than F6 and F7 (with 0% or 0.05% PS80, respectively). Based on the results of the EDTA study (F4 and F5), EDTA provided no additional stabilization of anti-Cx43 Ab.

Finally, 25 mg/mL anti-Cx43 Ab in 20 mM histidine/histidine hydrochloride at pH 5.5 with 8% sucrose and 0.02% (w/v) PS80 was considered as the lead formulation for the formulation confirmation study.

Example 4: Formulation Confirmation Study

The anti-Cx43 Ab formulation confirmation study was performed to confirm the stability of the selected formulation using final process DS. The conditions evaluated in the confirmation study include long storage conditions, accelerated conditions, stress conditions, freeze/thaw and agitation. The formulation selected from the formulation screening study was 25 mg/mL anti-Cx43 Ab in 20 mM histidine/histidine hydrochloride buffer at pH 5.5 with 8% (w/v) sucrose and 0.02% (w/v) PS80.

The lead formulation was evaluated in a formulation confirmation study. The mAb material ($1^{st}$ 15 L DS) was formulated as 25 mg/ml protein, 20 mM histidine/histidine hydrochloride buffer at pH 5.5 with 8% sucrose and 0.02% (w/v) PS80. The formulated DS was filtered using a 0.22 m PVDF filter, filled into 6 mL glass vials (6.0 mL/vial), stoppered and sealed in a bio-safety hood.

The appropriate number of vials were placed in 2~8° C. refrigerator, 25° C. and 40° C. stability chamber, respectively. Meanwhile, bottles were frozen in a −40° C. freezer and thawed at room temperature for 5 cycles or fixed to 100 rpm constant temperature shaker at 25° C. for 7 days, respectively. Samples were retrieved and analyzed at pre-determined time points.

Figure 16:
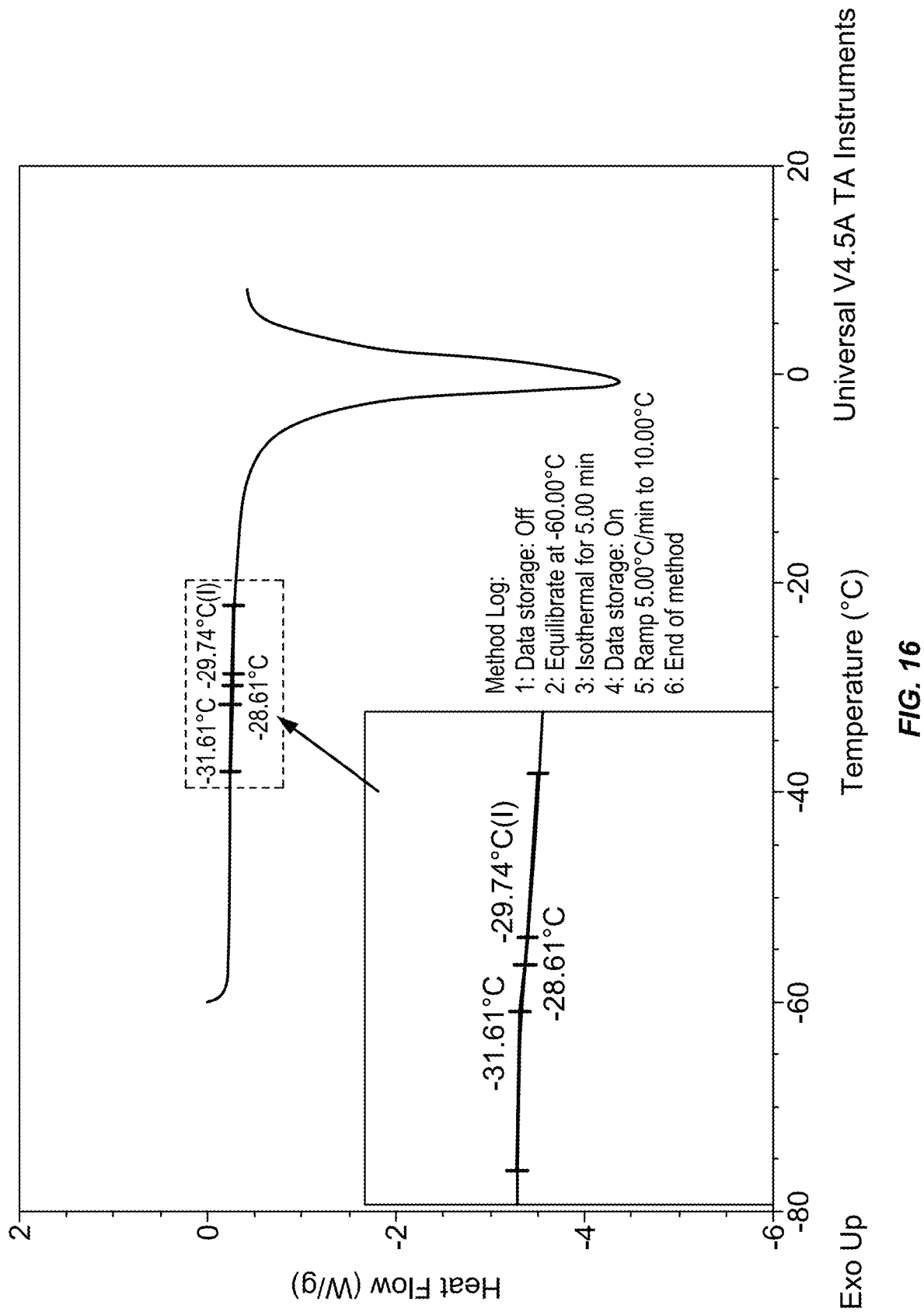
FIG. 16: MicroCal DSC thermogram overlay from the anti-Cx43 Ab formulation confirmation study.

The thermogram of anti-Cx43 Ab mAb in final formulation is shown in FIG. 16. The Tg' onset, the temperature at which the sample starts to glass translation, was considered as an indicator for the formation of glassy state. The Tg' onset of anti-Cx43 Ab was −31.61° C.

TABLE 27 mDSC data from the anti-Cx43 Ab formulation Confirmation study

| Sample ID | Tg' onset (° C.) | Tg' middle (° C.) | Tg' end (° C.) |
|---|---|---|---|
| 2142-20181201-T0 | −31.61° C. | −29.74° C. | −28.61° C. |

The appearance, protein concentration, pH and osmolality results of the freeze/thaw and agitation studies are summarized in Table 28.

There was no obvious change in the appearance, protein concentration, pH and osmolality after 5 freeze/thaw cycles (−40±5° C./RT) and 7-day agitation. All samples appeared colorless, slightly opalescent and free of visible particles. No obvious change was observed in protein concentration and all results were within the specification of 25.0±2.5 mg/mL. No obvious change was observed in pH and osmolality testing compared to T0.

TABLE 26

Study Parameters from the anti-Cx43 Ab Formulation Confirmation Study
DP (2142 150 mg/6 mL/vial; 6 R glass vial)

| | 2-8° C. | | 25° C. | | | 40° C. | | −40° C.~RT | Agitation 100 rpm |
|---|---|---|---|---|---|---|---|---|---|
| T0 | 1 M | 3 M | 1 M | 2 M | 3 M | 2 wks | 4 wks | FT-5C | 25-A-7D |
| x, y, z | x | x, z | x | x | x, z | x | x, z | x | x |

Notes:
x = Appearance, pH, Osmolality, Conc_UV280, SEC-HPLC, CEX, CE-SDS (R&NR), HIAC;
y = mDSC

TABLE 28

The appearance, protein concentration, pH and osmolality results from the freeze/thaw and agitation study

| Test Item | Sample ID | | |
|---|---|---|---|
| | 2142-20181201-T0 | 2142-20181201-FT-5 C | 2142-20181201-A-7 D |
| Appearance | A | A | A |
| Concentration (mg/mL) | 25.1 | 25.3 | 25.2 |
| pH | 5.6 | 5.5 | 5.6 |
| Osmolality (mOSm/kg) | 304 | 310 | 311 |

Notes:
A = Colorless, slightly opalescent and free of visible particles.

The particulate matter results of the freeze/thaw and agitation studies are summarized in Table 29. No growth trend of particle counts (ECD≥10 m and ECD≥25 m) was observed after 5 freeze/thaw cycles (−40±5° C./RT) and 7-day agitation at 25° C.

TABLE 29

HIAC data from the freeze/thaw and agitation study

| Test Item | | Sample ID | | |
|---|---|---|---|---|
| | | 2142-20181201-T0 | 2142-20181201-FT-5 C | 2142-20181201-A-7 D |
| HIAC | >=2 μm | 1814 | 518 | 687 |
| Concentration | >=10 μm | 49 | 10 | 9 |
| (#/ml) | >=25 μm | 1 | 0 | 1 |

The SEC-HPLC results of the freeze/thaw and agitation studies are summarized in Table 30. No obvious change was observed after 5 freeze/thaw cycles. A slight decline of SEC main peak purity (1.2%) was observed after 7 days of agitation (100 rpm) at 25° C.

TABLE 30

SEC data from the freeze/thaw and agitation study

| Test Item | Sample ID | | |
|---|---|---|---|
| | 2142-20181201-T0 | 2142-20181201-FT-5 C | 2142-20181201-A-7 D |
| Main Peak % | 99.4 | 99.2 | 98.2 |
| HMW Peak % | 0.6 | 0.8 | 1.7 |
| LMW Peak % | ND | ND | 0.1 |

The CE-SDS (NR&R) results of the freeze/thaw and agitation studies are summarized in Table 31. No obvious change in CE-SDS-NR and CE-SDS-R purity was observed after 5 freeze/thaw cycles. A slight decline of CE-SDS-NR purity (1.0%) and CE-SDS-R purity (2.1%) was observed after 7 days of agitation (100 rpm) at 25° C.

TABLE 31

CE-SDS data from the freeze/thaw and agitation study

| Test Item | Sample ID | | |
|---|---|---|---|
| | 2142-20181201-T0 | 2142-20181201-FT-5 C | 2142-20181201-A-7 D |
| CE-NR Purity % | 99.5 | 99.4 | 98.5 |
| CE-R purity % | 97.8 | 98.0 | 95.7 |

The CEX results of the freeze/thaw and agitation studies are summarized in Table 32. Compared to T0, there were no obvious changes in the proportion of main peak, acidic peak and basic peak after 5 freeze/thaw cycles (−40±5° C./RT). For samples agitated (100 rpm) at 25° C. for 7 days, a significant decrease of main peak (up to 17.9%) was observed.

TABLE 32

CEX data from the freeze/thaw and agitation study

| Test Item | 2142-20181201-T0 | 2142-20181201-FT-5 C | 2142-20181201-A-7 D |
|---|---|---|---|
| Main Peak % | 78.4 | 77.7 | 60.5 |
| Acidic Peak % | 13.5 | 13.5 | 16.3 |
| Basic Peak % | 8.1 | 8.8 | 23.2 |

The appearance, protein concentration, pH and osmolality results of different storage conditions are summarized in Table 33. All the samples were free of visible particles under different storage conditions except one sample held at 2~8° C. for 1 month, which appeared to contain some visible particles by accident. The sample color turned slightly yellow at 25° C.—1M/2M13M and 40° C.—2 W/4 W. Compared to T0, no obvious change was observed in protein concentration, pH and osmolality, which were all within the specification.

TABLE 33

Appearance, protein concentration, pH and osmolality results from the stability study

| | | 2142-20181201-05 | | | 2142-20181201-25 | | | 2142-20181201-40 | |
|---|---|---|---|---|---|---|---|---|---|
| Test Item | T0 | 1 M | 2 M | 3 M | 1 M | 2 M | 3 M | 2 W | 4 W |
| Appearance | A | C | A | A | B | B | B | A | B |
| Concentration (mg/mL) | 25.1 | 25.4 | 25.2 | 25.1 | 25.5 | 25.2 | 25.2 | 25.5 | 25.5 |
| pH | 5.6 | 5.6 | 5.6 | 5.6 | 5.6 | 5.6 | 5.6 | 5.6 | 5.5 |
| Osmolality (mOSm/kg) | 304 | 296 | 300 | 301 | 301 | 304 | 299 | 303 | 304 |

Notes:
A = Colorless slightly opalescent and free of visible particles;
B = Slightly yellow, slightly opalescent and free of visible particles;
C = Colorless, slightly opalescent and visible particles.

The HIAC results of samples under different storage conditions are summarized in Table 34. There was no obvious change in the sub-visible particle counts at 2~8° C., 25±2° C. and 40±2° C. for 2 weeks. The data generated at 2~8° C. for 1 month was for reference due to the generation of visible particles.

TABLE 34

HIAC data from the stability study

| | | | 2142-20181201-05 | | | 2142-20181201-25 | | | 2142-20181201-40 | |
|---|---|---|---|---|---|---|---|---|---|---|
| Test Item | | T0 | 1 M | 2 M | 3 M | 1 M | 2 M | 3 M | 2 W | 4 W |
| HIAC | >=2 μm | 1814 | 2620 | 409 | 1364 | 1397 | 519 | 1657 | 498 | 1288 |
| Concentration | >=10 μm | 49 | 86 | 14 | 24 | 31 | 30 | 33 | 12 | 33 |
| (#/ml) | >=25 μm | 1 | 2 | 1 | 0 | 1 | 0 | 0 | 1 | 0 |

The SEC-HPLC results of samples under different storage conditions are summarized in Table 35. For samples incubated at 2~8° C., a slight decline of main peak (drop of main peak was equal to 1.1%) was observed after 3 months of storage. For samples incubated at 25° C., a slight decline of main peak (drop of main peak was equal to 2.6%) was observed after 3 months of storage. For samples incubated at 40° C., a significant decrease of main peak (drop of main peak was equal to 5.1%) was observed after 4 weeks of storage.

TABLE 35

SEC data from the stability study

| | | Sample ID | | | | | | | |
|---|---|---|---|---|---|---|---|---|---|
| | | 2142-20181201-05 | | | 2142-20181201-25 | | | 2142-20181201-40 | |
| Test Item | T0 | 1 M | 2 M | 3 M | 1 M | 2 M | 3 M | 2 W | 4 W |
| Main peak % | 99.4 | 98.8 | 98.4 | 98.3 | 98.0 | 97.2 | 96.8 | 96.4 | 94.3 |
| HMW peak % | 0.6 | 1.1 | 1.6 | 1.6 | 1.9 | 2.7 | 3.1 | 3.4 | 5.2 |
| LMW peak % | ND | <0.1 | <0.1 | 0.1 | 0.2 | 0.1 | 0.2 | 0.2 | 0.5 |

The CE-SDS (NR&R) results of samples under different storage conditions are shown in Table 36. For samples incubated at 2~8° C., a CE-SDS purity decline (drop of CE_NR main peak was equal to 1.3% and drop of CE_R main peak was equal to 2.5%) was observed after 3 months of storage. For samples incubated at 25° C., a CE-SDS purity decline (drop of CE_NR main peak was equal to 6.1% and drop of CE_R main peak was equal to 8.0%) was observed after 3 months of storage. For samples incubated at 40° C., a CE-SDS purity decline (drop of CE_NR main peak was equal to 12.8% and drop of CE_R main peak was equal to 5.8%) was observed after 4 weeks of storage.

TABLE 36

CE-SDS data from the stability study

| | | Sample ID | | | | | | | |
|---|---|---|---|---|---|---|---|---|---|
| | | 2142-20181201-05 | | | 2142-20181201-25 | | | 2142-20181201-40 | |
| Test Item | T0 | 1 M | 2 M | 3 M | 1 M | 2 M | 3 M | 2 W | 4 W |
| CE-NR Purity % | 99.5 | 99.0 | 98.7 | 98.2 | 95.3 | 94.9 | 93.4 | 93.2 | 86.7 |
| CE-R purity % | 97.8 | 98.4 | 96.0 | 95.3 | 93.8 | 90.9 | 89.8 | 93.9 | 92.0 |

The CEX results of samples under different storage conditions are shown in Table 37. For samples incubated at 2~8° C., a decrease of main peak (drop of CEX main peak was equal to 20.4%) was observed after 3 months of storage. For samples incubated at 25° C., a decrease of main peak (drop of CEX main peak was equal to 20.0%) was observed after 3 months of storage. For samples incubated at 40° C., a decrease of main peak (drop of CEX main peak was equal to 30.6%) was observed after 4 weeks of storage.

TABLE 37

CEX data from the stability study

| | | Sample ID | | | | | | | |
|---|---|---|---|---|---|---|---|---|---|
| | | 2142-20181201-05 | | | 2142-20181201-25 | | | 2142-20181201-40 | |
| Test Item | T0 | 1 M | 2 M | 3 M | 1 M | 2 M | 3 M | 2 W | 4 W |
| Main peak % | 78.4 | 65.7 | 61.1 | 58.0 | 54.4 | 56.9 | 58.4 | 56.0 | 47.8 |
| Acidic peak % | 13.5 | 14.4 | 13.4 | 14.0 | 20.3 | 20.9 | 23.1 | 28.7 | 35.6 |
| Basic peak % | 8.1 | 19.8 | 25.6 | 27.9 | 25.2 | 22.3 | 18.5 | 15.2 | 16.6 |

After 5 freeze/thaw cycles (−40±5° C./RT), the anti-Cx43 Ab in the selected formulation had no significant change in appearance, protein concentration, pH value, osmolality and purity (SEC-HPLC, CEX-HPLC, CE-SDS Reduced & Non-Reduced).

After 7-day agitation at 25° C., the anti-Cx43 Ab in the selected formulation had no significant difference in appearance, protein concentration, pH value, osmolality. The purity (SEC-HPLC, CEX-HPLC, CE-SDS Reduced & Non-Reduced) of the selected formulation declined slightly.

After storage at 2~8° C. for 3 months, the anti-Cx43 Ab in the selected formulation had no significant change in appearance, protein concentration, pH value, osmolality and particle matter. The purity (SEC-HPLC, CEX-HPLC, CE-SDS Reduced & Non-Reduced) of the selected formulation declined slightly.

After storage at 25±2° C. for 3 months, the anti-Cx43 Ab in the selected formulation had no significant change in protein concentration, pH value, osmolality and particle matter. The color of the sample turned slightly yellow. The purity (SEC-HPLC, CEX-HPLC, CE-SDS Reduced & Non-Reduced) of the selected formulation declined after storage at 25±2° C. for 3 months.

After storage at 40±2° C. for 4 weeks, the anti-Cx43 Ab in the selected formulation had no significant change in protein concentration, pH value, osmolality and particle matter. The color of the sample turned slightly yellow. The purity (SEC-HPLC, CEX-HPLC, CE-SDS Reduced & Non-Reduced) of the selected formulation declined.

According to the confirmation study data, −20° C. was recommended as the DP storage condition.

In summary, 25 mg/mL protein in 20 mM histidine/histidine hydrochloride buffer at pH 5.5 with 8% sucrose and 0.02% (w/v) PS80 was considered as the formulation for the anti-Cx43 Ab. According to the confirmation study data, −20° C. was recommended as the DP storage condition.

MODIFICATIONS

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

---

The invention claimed is:

1. A pharmaceutical formulation comprising:
    an anti-Cx43 antibody or antigen binding fragment thereof;
    a buffer;
    a surfactant; and
    a stabilizer;
    wherein the pharmaceutical formulation has a pH of between about 5 and about 6;
    wherein the anti-Cx43 antibody or antigen binding fragment thereof comprises:
        a first, second and third heavy chain complementarity determining region (CDR) sequence having the amino acid sequence of SEQ ID NOs: 1, 2, and 3, respectively; and
        a first, second and third light chain CDR sequence having the amino acid sequence of SEQ ID NOs: 4, 5, and 6, respectively.

2. The pharmaceutical formulation of claim 1, wherein the anti-Cx43 antibody or antigen binding fragment thereof comprises a heavy chain variable domain having the amino acid sequence of SEQ ID NO: 7, and a light chain variable domain having the amino acid sequence of SEQ ID NO: 8.

3. The pharmaceutical formulation of claim 2, wherein the anti-Cx43 antibody or antigen binding fragment thereof comprises a heavy chain having an amino acid sequence selected from the group consisting of SEQ ID NOs: 11, 13, 15, and 17, and a light chain having the amino acid sequence of SEQ ID NO: 18.

4. The pharmaceutical formulation of claim 1, wherein the anti-Cx43 antibody or antigen binding fragment thereof binds to an epitope located within the amino acid sequence of FLSRPTEKTI (SEQ ID NO: 19).

5. The pharmaceutical formulation of claim 1, wherein the anti-Cx43 antibody or antigen binding fragment thereof is present at a concentration of between about 5 and about 50 mg/mL.

6. The pharmaceutical formulation of claim 5, wherein the antibody or antigen binding fragment thereof is present at a concentration of between about 15 to about 30 mg/mL.

7. The pharmaceutical formulation of claim 6, wherein the antibody or antigen binding fragment thereof is present at a concentration of 25 mg/mL.

8. The pharmaceutical formulation of claim 1, wherein the buffer is selected from acetate/sodium acetate, histidine/aspartic acid, citric acid/sodium citrate, dibasic sodium phosphate/sodium dihydrogen phosphate, and histidine/histidine hydrochloride.

9. The pharmaceutical formulation of claim 8, wherein the buffer is histidine/aspartic acid or histidine/histidine hydrochloride.

10. The pharmaceutical formulation of claim 9, wherein the buffer is histidine/histidine hydrochloride.

11. The pharmaceutical formulation of claim 1, wherein the surfactant is polysorbate 80 (PS80).

12. The pharmaceutical formulation of claim 1, wherein the stabilizer is selected from ethylenediaminetetraacetic acid (EDTA), sodium chloride, sorbitol, glycine, and sucrose.

13. The pharmaceutical formulation of claim 12, wherein the stabilizer is sucrose.

14. The pharmaceutical formulation of claim 1, wherein the pH is between about 5.4 to about 5.6.

15. The pharmaceutical formulation of claim 1, wherein the formulation is an aqueous formulation.

16. A pharmaceutical formulation comprising:
    about 25 mg/mL of an anti-Cx43 antibody or antigen binding fragment thereof;
    about 20 mM histidine/histidine hydrochloride buffer;
    about 0.02% w/v Polysorbate 80; and
    about 8% w/v sucrose;
    wherein the formulation has a pH of about 5.5;
    wherein the antibody or antigen binding fragment thereof comprises:
        a first, second and third heavy chain complementarity determining region (CDR) sequence having the amino acid sequence of SEQ ID NOs: 1, 2, and 3, respectively; and
        a first, second and third light chain CDR sequence having the amino acid sequence of SEQ ID NOs: 4, 5, and 6, respectively.

17. A pharmaceutical formulation comprising:
    about 25 mg/mL an anti-Cx43 antibody or antigen binding fragment thereof, comprising a heavy chain having an amino acid sequence selected from the group consisting of SEQ ID NOs: 11, 13, 15, and 17, and comprising a light chain having the amino acid sequence of SEQ ID NO: 18;
    about 20 mM histidine/aspartic acid buffer;
    about 0.02% w/v Polysorbate 80; and
    about 8% w/v sucrose,
    wherein the formulation has a pH of about 5.5.

18. A method for promoting opening of Cx43 hemichannels in osteocytes, comprising administering to a subject in need thereof a therapeutically effective amount of the pharmaceutical formulation of claim 1, optionally for the treatment of cancer, cancer metastasis, osteosarcoma, osteoporosis, or osteopenia.

19. A method for promoting opening of Cx43 hemichannels in osteocytes, comprising administering to a subject in need thereof a therapeutically effective amount of the pharmaceutical formulation of claim 16, optionally for the treatment of cancer, cancer metastasis, osteosarcoma, osteoporosis, or osteopenia.

20. A method for promoting opening of Cx43 hemichannels in osteocytes, comprising administering to a subject in need thereof a therapeutically effective amount of the pharmaceutical formulation of claim 17, optionally for the treatment of cancer, cancer metastasis, osteosarcoma, osteoporosis, or osteopenia.

\* \* \* \* \*

SEQUENCE LISTING

```
<160> NUMBER OF SEQ ID NOS: 39

<210> SEQ ID NO 1
<211> LENGTH: 8
<212> TYPE: PRT
<213> ORGANISM: Unknown
<220> FEATURE:
<223> OTHER INFORMATION: Synthetic

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: Unknown
<220> FEATURE:
<223> OTHER INFORMATION: Synthetic

<400> SEQUENCE: 2

Ile Asn Pro Ser Asn Ala Gly Thr
1               5

<210> SEQ ID NO 3
<211> LENGTH: 12
<212> TYPE: PRT
<213> ORGANISM: Unknown
<220> FEATURE:
<223> OTHER INFORMATION: Synthetic

<400> SEQUENCE: 3

Thr Arg Glu Gly Asn Pro Tyr Tyr Thr Met Asn Tyr
1               5                   10
```

```
<210> SEQ ID NO 4
<211> LENGTH: 11
<212> TYPE: PRT
<213> ORGANISM: Unknown
<220> FEATURE:
<223> OTHER INFORMATION: Synthetic

<400> SEQUENCE: 4

Gln Ser Leu Leu Glu Ser Asp Gly Lys Thr Tyr
1               5                   10

<210> SEQ ID NO 5
<211> LENGTH: 3
<212> TYPE: PRT
<213> ORGANISM: Unknown
<220> FEATURE:
<223> OTHER INFORMATION: Synthetic

<400> SEQUENCE: 5

Leu Val Ser
1

<210> SEQ ID NO 6
<211> LENGTH: 9
<212> TYPE: PRT
<213> ORGANISM: Unknown
<220> FEATURE:
<223> OTHER INFORMATION: Synthetic

<400> SEQUENCE: 6

Trp Gln Gly Thr His Phe Pro Trp Thr
1               5

<210> SEQ ID NO 7
<211> LENGTH: 119
<212> TYPE: PRT
<213> ORGANISM: Unknown
<220> FEATURE:
<223> OTHER INFORMATION: Synthetic

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser
        115

<210> SEQ ID NO 8
<211> LENGTH: 112
<212> TYPE: PRT
<213> ORGANISM: Unknown
<220> FEATURE:
```

<223> OTHER INFORMATION: Synthetic

<400> SEQUENCE: 8

```
Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gly Gly Thr Lys Val Glu Ile Lys
            100                 105                 110
```

<210> SEQ ID NO 9
<211> LENGTH: 449
<212> TYPE: PRT
<213> ORGANISM: Unknown
<220> FEATURE:
<223> OTHER INFORMATION: Synthetic

<400> SEQUENCE: 9

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
            290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys

<210> SEQ ID NO 10
<211> LENGTH: 446
<212> TYPE: PRT
<213> ORGANISM: Unknown
<220> FEATURE:
<223> OTHER INFORMATION: Synthetic

<400> SEQUENCE: 10

Glu Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
            20              25              30

Tyr Met Tyr Trp Val Arg Gln Ala Pro Gly Gln Gly Leu Glu Trp Ile
            35              40              45

Gly Gly Ile Asn Pro Ser Asn Gly Gly Thr Asn Phe Asn Glu Lys Phe
50              55              60

Lys Asn Arg Ala Thr Leu Thr Val Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Thr Arg Glu Gly Asn Pro Tyr Tyr Thr Met Asn Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
            130             135             140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 11
<211> LENGTH: 446
<212> TYPE: PRT
<213> ORGANISM: Unknown
<220> FEATURE:
<223> OTHER INFORMATION: Synthetic

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Ala Gly Thr Asn Phe Asn Glu Lys Phe
        50                  55                  60
```

```
Lys Asn Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 12
<211> LENGTH: 449
<212> TYPE: PRT
<213> ORGANISM: Unknown
<220> FEATURE:
<223> OTHER INFORMATION: Synthetic
```

<400> SEQUENCE: 12

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Tyr | Met | Tyr | Trp | Val | Arg | Gln | Ala | Pro | Gly | Gln | Gly | Leu | Glu | Trp | Ile |
| | | 35 | | | | | 40 | | | | | 45 | | | |
| Gly | Gly | Ile | Asn | Pro | Ser | Asn | Gly | Gly | Thr | Asn | Phe | Asn | Glu | Lys | Phe |
| | 50 | | | | | 55 | | | | | 60 | | | | |
| Lys | Asn | Arg | Ala | Thr | Leu | Thr | Val | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Thr | Arg | Glu | Gly | Asn | Pro | Tyr | Tyr | Thr | Met | Asn | Tyr | Trp | Gly | Gln | Gly |
| | | | | 100 | | | | | 105 | | | | | 110 | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | | 180 | | | | | 185 | | | | | 190 | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Ala | Ala | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | | 260 | | | | | 265 | | | | | 270 | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |
| Asp | Ser | Asp | Gly | Ser | Phe | Phe | Leu | Tyr | Ser | Lys | Leu | Thr | Val | Asp | Lys |

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 449
<212> TYPE: PRT
<213> ORGANISM: Unknown
<220> FEATURE:
<223> OTHER INFORMATION: Synthetic

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 446
<212> TYPE: PRT
<213> ORGANISM: Unknown
<220> FEATURE:
<223> OTHER INFORMATION: Synthetic

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

```
Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 15
<211> LENGTH: 446
<212> TYPE: PRT
<213> ORGANISM: Unknown
<220> FEATURE:
<223> OTHER INFORMATION: Synthetic

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445
```

<210> SEQ ID NO 16
<211> LENGTH: 446
<212> TYPE: PRT
<213> ORGANISM: Unknown
<220> FEATURE:
<223> OTHER INFORMATION: Synthetic

<400> SEQUENCE: 16

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60
```

Lys Asn Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 17
<211> LENGTH: 446
<212> TYPE: PRT
<213> ORGANISM: Unknown
<220> FEATURE:
<223> OTHER INFORMATION: Synthetic

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Ala Gly Thr Asn Phe Asn Glu Lys Phe
    50                  55                  60

Lys Asn Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp 405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 18
<211> LENGTH: 219
<212> TYPE: PRT
<213> ORGANISM: Unknown
<220> FEATURE:
<223> OTHER INFORMATION: Synthetic

<400> SEQUENCE: 18

Asp Val Val Met Thr Gln Ser Pro Leu Ser Leu Pro Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 19
<211> LENGTH: 10
<212> TYPE: PRT
<213> ORGANISM: Homo sapiens

<400> SEQUENCE: 19

Phe Leu Ser Arg Pro Thr Glu Lys Thr Ile
1               5                   10

<210> SEQ ID NO 20
<211> LENGTH: 10
<212> TYPE: PRT
<213> ORGANISM: Unknown
<220> FEATURE:
<223> OTHER INFORMATION: Synthetic

```
<400> SEQUENCE: 20

Phe Trp Ser Arg Pro Thr Glu Lys Thr Ile
1               5                   10

<210> SEQ ID NO 21
<211> LENGTH: 10
<212> TYPE: PRT
<213> ORGANISM: Unknown
<220> FEATURE:
<223> OTHER INFORMATION: Synthetic

<400> SEQUENCE: 21

Phe Leu Ser Arg Pro Thr Glu Lys Thr Cys
1               5                   10

<210> SEQ ID NO 22
<211> LENGTH: 10
<212> TYPE: PRT
<213> ORGANISM: Unknown
<220> FEATURE:
<223> OTHER INFORMATION: Synthetic

<400> SEQUENCE: 22

Phe Leu Gly Arg Pro Thr Glu Lys Thr Ile
1               5                   10

<210> SEQ ID NO 23
<211> LENGTH: 10
<212> TYPE: PRT
<213> ORGANISM: Unknown
<220> FEATURE:
<223> OTHER INFORMATION: Synthetic

<400> SEQUENCE: 23

Phe Leu Ser Arg Pro Thr Glu Lys Asp Ile
1               5                   10

<210> SEQ ID NO 24
<211> LENGTH: 10
<212> TYPE: PRT
<213> ORGANISM: Unknown
<220> FEATURE:
<223> OTHER INFORMATION: Synthetic

<400> SEQUENCE: 24

Phe Leu Ser Arg Pro Thr Glu Lys Tyr Ile
1               5                   10

<210> SEQ ID NO 25
<211> LENGTH: 10
<212> TYPE: PRT
<213> ORGANISM: Unknown
<220> FEATURE:
<223> OTHER INFORMATION: Synthetic

<400> SEQUENCE: 25

Phe Leu Ser Arg Trp Thr Glu Lys Thr Ile
1               5                   10

<210> SEQ ID NO 26
<211> LENGTH: 10
<212> TYPE: PRT
<213> ORGANISM: Unknown
<220> FEATURE:
<223> OTHER INFORMATION: Synthetic

<400> SEQUENCE: 26
```

Phe Leu Ser Arg Pro Ser Glu Lys Thr Ile
1               5                   10

<210> SEQ ID NO 27
<211> LENGTH: 10
<212> TYPE: PRT
<213> ORGANISM: Unknown
<220> FEATURE:
<223> OTHER INFORMATION: Synthetic

<400> SEQUENCE: 27

Phe Leu Asn Arg Pro Thr Glu Lys Thr Ile
1               5                   10

<210> SEQ ID NO 28
<211> LENGTH: 10
<212> TYPE: PRT
<213> ORGANISM: Unknown
<220> FEATURE:
<223> OTHER INFORMATION: Synthetic

<400> SEQUENCE: 28

Phe Leu Ser Arg Pro Phe Glu Lys Thr Ile
1               5                   10

<210> SEQ ID NO 29
<211> LENGTH: 10
<212> TYPE: PRT
<213> ORGANISM: Unknown
<220> FEATURE:
<223> OTHER INFORMATION: Sythetic

<400> SEQUENCE: 29

Phe Leu Ser Arg Pro Thr Glu Lys Thr Gly
1               5                   10

<210> SEQ ID NO 30
<211> LENGTH: 5
<212> TYPE: PRT
<213> ORGANISM: Unknown
<220> FEATURE:
<223> OTHER INFORMATION: Synthetic

<400> SEQUENCE: 30

Phe Leu Ser Arg Pro
1               5

<210> SEQ ID NO 31
<211> LENGTH: 5
<212> TYPE: PRT
<213> ORGANISM: Unknown
<220> FEATURE:
<223> OTHER INFORMATION: Synthetic

<400> SEQUENCE: 31

Leu Ser Arg Pro Thr
1               5

<210> SEQ ID NO 32
<211> LENGTH: 5
<212> TYPE: PRT
<213> ORGANISM: Unknown
<220> FEATURE:
<223> OTHER INFORMATION: Synthetic

<400> SEQUENCE: 32

```
Ser Arg Pro Thr Glu
1               5

<210> SEQ ID NO 33
<211> LENGTH: 5
<212> TYPE: PRT
<213> ORGANISM: Unknown
<220> FEATURE:
<223> OTHER INFORMATION: Synthetic

<400> SEQUENCE: 33

Arg Pro Thr Glu Lys
1               5

<210> SEQ ID NO 34
<211> LENGTH: 5
<212> TYPE: PRT
<213> ORGANISM: Unknown
<220> FEATURE:
<223> OTHER INFORMATION: Synthetic

<400> SEQUENCE: 34

Pro Thr Glu Lys Thr
1               5

<210> SEQ ID NO 35
<211> LENGTH: 5
<212> TYPE: PRT
<213> ORGANISM: Unknown
<220> FEATURE:
<223> OTHER INFORMATION: Synthetic

<400> SEQUENCE: 35

Thr Glu Lys Thr Ile
1               5

<210> SEQ ID NO 36
<211> LENGTH: 6
<212> TYPE: PRT
<213> ORGANISM: Unknown
<220> FEATURE:
<223> OTHER INFORMATION: Synthetic

<400> SEQUENCE: 36

Phe Leu Ser Arg Pro Thr
1               5

<210> SEQ ID NO 37
<211> LENGTH: 6
<212> TYPE: PRT
<213> ORGANISM: Unknown
<220> FEATURE:
<223> OTHER INFORMATION: Synthetic

<400> SEQUENCE: 37

Leu Ser Arg Pro Thr Glu
1               5

<210> SEQ ID NO 38
<211> LENGTH: 6
<212> TYPE: PRT
<213> ORGANISM: Unknown
<220> FEATURE:
<223> OTHER INFORMATION: Synthetic

<400> SEQUENCE: 38

Ser Arg Pro Thr Glu Lys
```

```
<210> SEQ ID NO 39
<211> LENGTH: 6
<212> TYPE: PRT
<213> ORGANISM: Unknown
<220> FEATURE:
<223> OTHER INFORMATION: Synthetic

<400> SEQUENCE: 39

Arg Pro Thr Glu Lys Thr
1               5
```